US010161939B2

(12) United States Patent
Rao et al.

(10) Patent No.: US 10,161,939 B2
(45) Date of Patent: Dec. 25, 2018

(54) METHOD OF ISOLATING CIRCULATING TUMOR CELLS

(71) Applicants: Duke University, Durham, NC (US); Janssen Diagnostics, LLC, Raritan, NJ (US)

(72) Inventors: Galla Chandra Rao, Princeton Junction, NJ (US); Mark C. Connelly, Doylestown, PA (US); Mariano A. Garcia-Blanco, Hillsborough, NC (US); Andrew J. Armstrong, Chapel Hill, NC (US); Rhonda L. Bitting, Durham, NC (US)

(73) Assignees: Duke University, Durham, NC (US); Janssen Diagnostics, LLC, Raritan, NJ (US)

( * ) Notice: Subject to any disclaimer, the term of this patent is extended or adjusted under 35 U.S.C. 154(b) by 0 days.

(21) Appl. No.: 14/765,071

(22) PCT Filed: May 31, 2013

(86) PCT No.: PCT/US2013/043745
§ 371 (c)(1),
(2) Date: Jul. 31, 2015

(87) PCT Pub. No.: WO2014/120265
PCT Pub. Date: Aug. 7, 2014

(65) Prior Publication Data
US 2016/0077097 A1    Mar. 17, 2016

Related U.S. Application Data

(60) Provisional application No. 61/760,042, filed on Feb. 2, 2013, provisional application No. 61/806,358, filed on Mar. 28, 2013.

(51) Int. Cl.
*G01N 33/574* (2006.01)
*G01N 33/543* (2006.01)
*G01N 33/569* (2006.01)

(52) U.S. Cl.
CPC . *G01N 33/57484* (2013.01); *G01N 33/54326* (2013.01); *G01N 33/56966* (2013.01); *G01N 33/57415* (2013.01); *G01N 33/57434* (2013.01); *G01N 33/57492* (2013.01); *G01N 2333/47* (2013.01); *G01N 2333/4703* (2013.01); *G01N 2333/4742* (2013.01); *G01N 2333/705* (2013.01); *G01N 2333/70503* (2013.01); *G01N 2333/70589* (2013.01); *G01N 2333/70596* (2013.01)

(58) Field of Classification Search
CPC .................................................. G01N 33/574
USPC ....................... 435/7.23, 7.1, 6.14
See application file for complete search history.

(56) References Cited

U.S. PATENT DOCUMENTS

| 5,352,803 | A | 10/1994 | Mattingly |
|---|---|---|---|
| 5,359,093 | A | 10/1994 | Adamczyk |
| 5,496,925 | A | 3/1996 | Mattingly |
| 5,573,904 | A | 11/1996 | Mattingly |
| 5,593,896 | A | 1/1997 | Adamczyk et al. |
| 6,197,523 | B1 | 3/2001 | Rimm et al. |
| 6,355,623 | B2 | 3/2002 | Seidman |
| 6,433,149 | B1 | 8/2002 | Blaschuk et al. |
| 6,566,063 | B1 | 5/2003 | Kaufmann et al. |
| 6,645,731 | B2 | 11/2003 | Terstappen et al. |
| 7,056,660 | B1 | 6/2006 | Giesieng |
| 2002/0146687 | A1 | 10/2002 | Blaschuk et al. |
| 2002/0169106 | A1 | 11/2002 | Blaschuk et al. |
| 2007/0026417 | A1 | 2/2007 | Fuchs et al. |
| 2009/0305963 | A1 | 12/2009 | Sukhatme et al. |
| 2013/0171642 | A1* | 7/2013 | Pestano ............ G01N 33/57434 435/6.11 |
| 2013/0209493 | A1 | 8/2013 | Garcia-Blanco |
| 2013/0255361 | A1* | 10/2013 | Juncker ................ C12M 1/12 73/61.59 |

FOREIGN PATENT DOCUMENTS

| WO | WO 2001/058956 | 8/2001 |
|---|---|---|
| WO | WO 2005/043121 | 5/2005 |
| WO | WO 2008/073603 | 6/2008 |
| WO | WO 2009/036968 | 3/2009 |
| WO | 2010/111388 | 9/2010 |
| WO | WO 2011/093927 | 8/2011 |

OTHER PUBLICATIONS

Scatena et al. (Biochimica et Biophysica Acta, 2013, 1835: 129-143, available online Dec. 7, 2012).*
United States Patent Office Final Action for U.S. Appl. No. 13/575,638 dated Jul. 14, 2016 (20 pages).
Acloque, H., et al. "Epithelial-mesenchymal transitions: the importance of changing cell state in development and disease" J. Clin. Invest. 2009, 119, 1438-1449.
Armstrong et al., "Circulating Tumor Cells from Patients with Advanced Prostate and Breast Cancer Displays Both Epithelial and Mesenchymal Markers" Molecular Cancer Research, 9(8) Aug. 2011, 11 pages.

(Continued)

*Primary Examiner* — Yan Xiao
(74) *Attorney, Agent, or Firm* — Michael Best & Friedrich LLP

(57) ABSTRACT

Provided are methods for detecting or isolating circulating tumor cells (CTCs) in a subject. The methods may include detecting the expression of at least one epithelial mesenchymal transition (EMT) biomarker. Further provided are kits for detecting or isolating CTCs. The kits may include antibodies to at least one EMT biomarker. Further provided are methods of predicting the responsiveness of a subject to a cancer drug, methods of targeting delivery of a cancer drug in a subject, methods of providing a cancer prognosis to a subject, and methods for following the progress of cancer in a subject.

11 Claims, 23 Drawing Sheets
Specification includes a Sequence Listing.

(56) References Cited

OTHER PUBLICATIONS

Hay, E.D., et al. "Transformations Between Epithelium and Mesenchyme: Normal, Pathological, and Experimentally Induced" Am. J. Kidney Dis. 1995, 26, 678-690.
Masuda, N., et al., "Analysis of chemical modification of RNA from formalin-fixed samples and optimization of molcular biology applications for such samples" Nucleic Acids Res 1999, 27, 4436.
Oltean et al., "Alternative inclusion of fibroblast growth factor receptor 2 exon IIIc in Dunning prostate tumors reveals unexpected epithelial mesenchymal plasticity" Proc Natl Acad Sci USA 2006, 103, 14116-14121.
Aktas et al., "Stem cell and epithelial-mesenchymal transition markers are frequently overexpressed in circulating tumor cells of metastatic breast cancer patients" Breast Cancer Research, Current Science, London, GB, vol. 11, No. 4, Jul. 9, 2009, p. R46.
Tomaskovic-Crook et al., "Epithelial to mesenchymal transition and breast cancer" Breast Cancer Research : BCR 2009, vol. 11, No. 6, 2009, p. 213.
Pollack V. et al., "Oncostatin M-induced effects on EMT in human proximal tubular cells: differential role of ERK signaling" American Journal of Physiology: Renal, Fluid and Electrolytephysiology, American Physiological Society, US, vol. 293, No. 5, Nov. 1, 2007, pp. F1714-F1726.
Wu, C., et al., "Simultaneous targeting of multiple disease mediators by a dual-variable-domain immunoglobulin," Nature Biotechnology, 25(11):1290-1297 (2007).
Polak and Van Noorden, Introduction to Immunocytochemistry, 3nd ed., Springer Verlag, N.Y. (2003).
Haugland, Handbook of Fluorescent Probes and Research Chemicals (1996).
Adamczyk et al., "Chemiluminescent acridinium-9-carboxamide boronic acid probes: Application to a homogeneous glycated hemoglobin assay," Bioorg. Med. Chem. Lett. 16: 1324-1328 (2006).
Adamczyk et al., "Chemiluminescence quenching of pteroic acid-N-sulfonylacridinium-9-carboxamide conjugates by folate binding protein," Bioorg. Med. Chem. Lett. 4: 2313-2317 (2004).
Adamczyk et al., "Intrinsic factor-mediated modulation of cyanocobalamin-N-sulfonyl-acridinium-9-carboxamide chemiluminescence," Biorg. Med. Chem. Lett. 14: 3917-3921 (2004).
Adamczyk et al., "Regiodependent Luminescence Quenching of Biotinylated N-Sulfonyl-acridinium-9-carboxamides by Avidin," Org. Lett. 5: 3779-3782 (2003).
Allard et al. "Tumor Cells Circulate in the Peripheral Blood of All Major Carcinomas but not in Healthy Subjects or Patients With Nonmalignant Diseases," (2004) Clin Cancer Res 10:6897-6904.
Pusztaszeri et al. "Immunohistochemical Expression of Endothelial Markers CD31, CD34, von Willebrand Factor, and Fli-1 in Normal Human Tissues," (2006) J Histochem Cytochem 54:385-395.
Attard et al. "Characterization of ERG, AR and PTEN Gene Status in Circulating Tumor Cells from Patients with Castration-Resistant Prostate Cancer," (2009) Cancer Res 69:2912-2918.
Bitting et al., "Development of a method to isolate circulating tumor cells using mesenchymal-based capture," Methods 64 (2013) 129-136.

Schneider et al., "Cadherin-11 contributes to pulmonary fibrosis: potential role in TGF-production and epithelial to mesenchymal transition," The FASEB Journal, vol. 26, Feb. 2012, 503-512.
Huang et al., "Cadherin-11 Increases Migration and Invasion of Prostate Cancer Cells and Enhances their Interaction with Osteoblasts," Cancer Res 2010;70:4580-4589.
Bitting et al., "Evaluation of clinical phenotype, survival, and circulating tumor cell (CTC) enumeration in men with metastatic castration-resistant prostate cancer (mCRPC)." ASCO Meeting Abstracts Jun 17, 2013:5031.
Bitting et al., "Isolation of circulating tumor cells using a novel EMT-based capture method." ASCO Meeting Abstracts May 30, 2012:10533.
PCT/US2010/050223 International Search Report and Written Opinion dated Jan. 13, 2011 (8 pages).
European Patent Office Search Report for Application No. 10844915.8 dated Jun. 6, 2013 (12 pages).
Inernational Search Report and Written Opinion for Application No. PCT/US13/43745 dated Oct. 24, 2013 (18 pages).
European Patent Office Action for Application No. 10844915.8 dated Mar. 7, 2014 (4 pages).
United States Patent Office Action for U.S. Appl. No. 13/575,638 dated Dec. 19, 2014 (19 pages).
United States Patent Office Final Action for U.S. Appl. No. 13/575,638 dated Aug. 21, 2015 (13 pages).
Chu et al., "Cadherin-11 Promotes the Metastasis of Prostate Cancer Cells to Bone," Mol. Cancer Res. Aug. 2008; 1259-1267.
Jérôme Doyen et al., "Circulating tumor cells in prostate cancer: a potential surrogate marker of survival" Critical Review in Oncology/Hematology, Dec. 31, 2012, pp. 241-256.
European Patent Office Action for Application No. 16152292.5 dated Apr. 8, 2016 (9 pages).
United States Patent Office Final Action for U.S. Appl. No. 13/575,638 dated Feb. 8, 2016 (18 pages).
Chinese Patent Office Action and Search Report for Application No. 201380075303.3 dated Mar. 31, 2016 (20 pages—including translation).
Great Britain Examination Report for Application No. 1514789.5 dated Feb. 17, 2017 (3 pages).
Chinese Patent Office Action for Application No. 201380075303.3 dated Jan. 1, 2017 (22 pages—including translation).
Great Britain Search and Examination Report for Application No. 1706134.2 dated May 4, 2017 (4 pages).
Great Britain Examination Report for Application No. 1514789.5 dated May 4, 2017 (3 pages).
Chinese Patent Office Action for Application No. 201380075303.3 dated Jan. 3, 2018 (11 pages, English translation included).
Nadri et al., "An efficient method tor isolation of murine bone marrow mesenchymal stem cells", Int. J. Dev. Biol., 2007, vol. 51, p. 723-729.
Vodyanik et al., "A Mesoderm-Derived Precursor tor Mesenchymal Stem and Endothelial Cells", Cell Stem Cell, 2010, vol. 7, p. 718-729.
Zeisberg et al., "Discovery of Endothelialto Mesenchymal Transition as a Source tor Carcinoma-Associated Fibroblasts", Cancer Res., 2007, vol. 67, No. 21, p. 10123-8.
Chinese Patent Office Action for Application No. 201380075303.3 dated Jul. 19, 2017 (19 pages—including translation).

\* cited by examiner

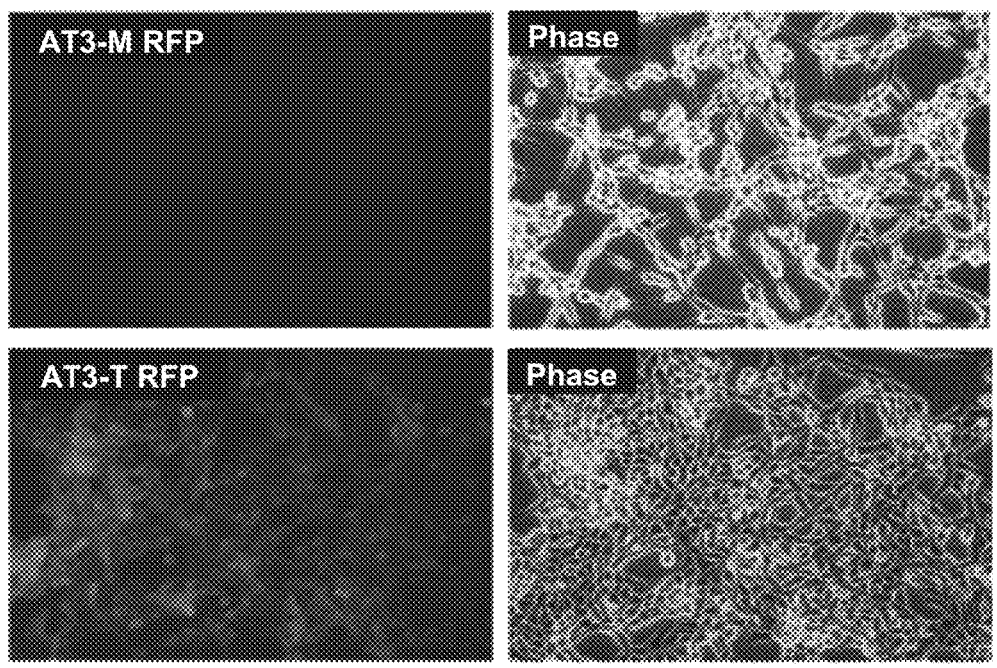
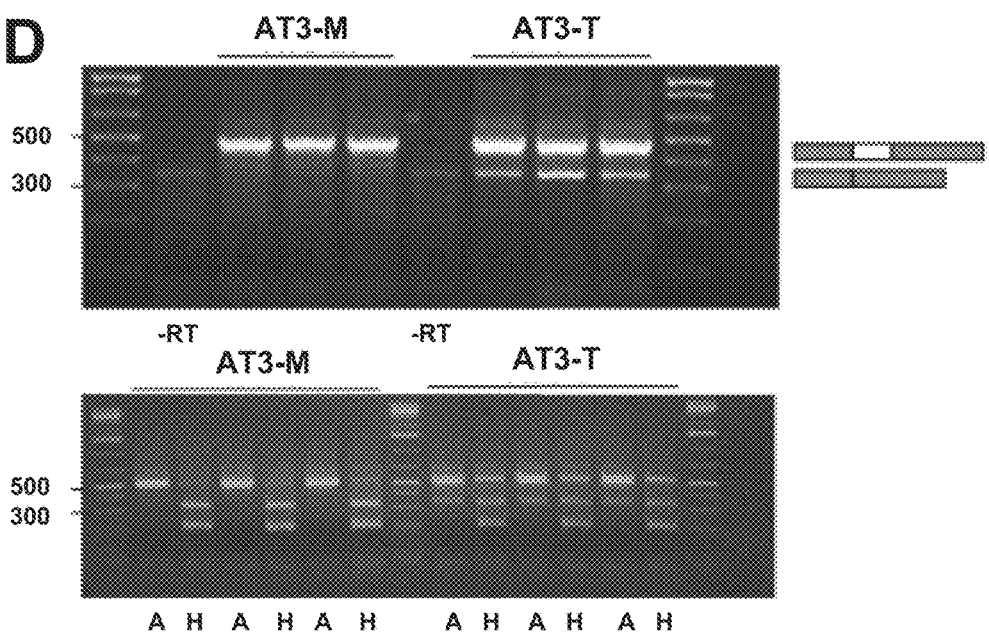
FIGURE 1, CONTINUED

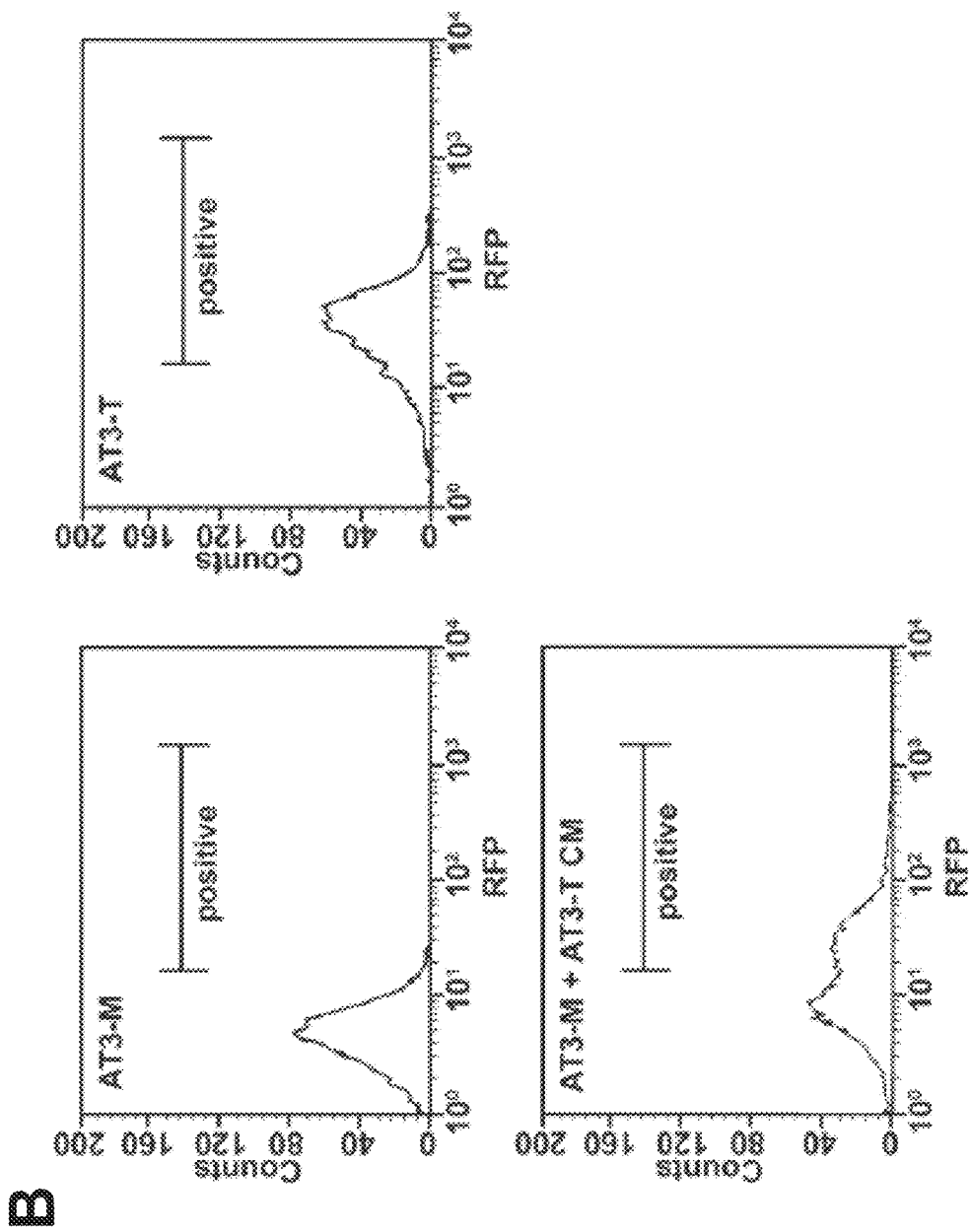
FIGURE 2, CONTINUED

SEQUENCE LISTING

<160> NUMBER OF SEQ ID NOS: 24

<210> SEQ ID NO 1
<211> LENGTH: 4321
<212> TYPE: DNA
<213> ORGANISM: Mus musculus

<400> SEQUENCE: 1

```
cacacacaca cgcacacaca cacacacaca cacttctcgg cgcgcacgac gcccgccctt    60
ctccccgccc cctccccagc tccttgatct cccgtctgtt ttattactcc tggtgcgagt   120
ccggcggact ccgaggcccg ctatttgtta ccaactcgct ctcattggcg gggaggagag   180
cagcggagaa gggggtgggg aggggagggg aagggaaggg gtggccactg ccggagccga   240
ctccgcgctg ctgttggtgc cgctgccgct tctgctgcct ctgctgccgc cgccgccgcc   300
tccggctcct cgctcggccc ctctccgcct ccatgtgccg gatagcggga gcgccgcgga   360
ccctgctgcc gcttctggcg gccttgcttc aggcgtctgt ggaggcttct ggtgaaattg   420
cattatgcaa gactggattt cctgaagatg tttacagcgc agtcttaccg aaggatgtgc   480
acgaaggaca gccccttctc aatgtgaaat tcagcaactg caatagaaaa aggaaagttc   540
agtatgaaag cagcgagcca gcagatttca aggtggacga ggacggcacg gtgtatgctg   600
tgagaagctt ccctctcact gcagagcagg caaagttcct gatatatgcc caagacaaag   660
```

```
aaacccagga aaagtggcag gtagctgtaa acctgagccg ggagccaacc ctgactgagg      720
agcctatgaa ggaaccacat gaaattgaag aaatagtatt ccctagacaa cttgccaagc      780
acagtggagc tctacaaagg cagaagagag actgggtcat cccgccaatc aacttgccag      840
aaaactccag aggacccttt cctcaagagc ttgtcagaat caggtctgat agagataaaa      900
acctttccct gagatacagc gtcactgggc caggagctga ccagcctcca acgggcatct      960
tcattatcaa ccccatctca ggacagctgt cagtcacaaa gcctctggat cgagagctga     1020
tagcccggtt tcacttgaga gcacatgcag tggacatcaa tggcaatcaa gtggagaacc     1080
ccattgacat tgtcatcaat gttattgaca tgaatgataa cagacctgag tttctgcacc     1140
aggtttggaa tgggtctgtt ccagagggat caaagcctgg gacgtatgtg atgacggtca     1200
ctgccattga tgcggatgat ccaaatgccc tgaatggaat gctgcggtac aggatcctgt     1260
cccaggcgcc cagcacacct tcacccaaca tgtttacaat caacaatgag actggggaca     1320
tcatcactgt ggcagctggt ctggatcgag agaaagtgca acagtatacg ttaataattc     1380
aagccacaga catggaaggc aatcccactt atggcctttc aaacacagcc acagccgtca     1440
tcacggtgac agatgtcaat gacaatcctc cagagtttac tgccatgact ttctacggag     1500
aagtccctga aacagggtg gacgtcattg tagccaacct aactgtcacg gacaaagatc     1560
agccccacac gccggcctgg aatgcggcat acagaatcag tggtggagac cctacaggaa     1620
ggtttgccat cctgacagac cccaacagca atgatgggct agtcacagtg gtaaaaccaa     1680
ttgactttga aacgaatagg atgtttgtcc ttactgttgc tgcagaaaac caagtgccat     1740
tagctaaagg cattcagcac ccacctcagt cgacagccac tgtgtctgtg acagttattg     1800
atgtcaatga aaatccttat tttgccccaa atcctaaaat cattcgccaa gaggaaggcc     1860
tccacgcagg taccatgctg accacgctca ctgctcagga ccccgatcga tatatgcaac     1920
agaatatcag atacacaaaa ttgtctgatc ctgccaactg gctgaaaata accccgtga      1980 atgggcagat cactactatt gccgtttggg acagagaatc gccaaatgta aaaaacaaca     2040
tctataatgc taccttcctt gcttctgaca atggaatccc gcctatgagt gggacaggaa     2100
cactgcaaat ctatttactt gatatcaatg acaacgcccc tcaggtgtta cctcaagagg     2160
cggagacctg tgaaactcca gaacccaact caattaacat cacagcactt gattatgaca     2220
tagacccaaa cgccgggccg ttcgcgtttg atcttccctt atctccagtg actattaaaa     2280
gaaactggac catcaaccgg cttaatggtg attttgctca gctcaattta aagataaaat     2340
ttttggaagc tggtatctat gaagttccca tcattatcac agattcaggg aatccccca      2400 agtccaacat ttccatcctg cgtgtgaaag tttgtcagtg tgactccaat ggagactgca     2460
cggacgtgga caggatcgtg ggtgcagggc ttggcacggg cgccatcatc gctatccttc     2520
tgtgtatcat catcctgctg atccttgttc tcatgtttgt ggtatggatg aaacggcggg     2580
ataaagagcg ccaagccaag cagcttttaa ttgacccaga agatgatgta agagataata     2640
tattgaaata tgatgaagaa ggtggaggag aagaagacca ggactatgac ttgagccagc     2700
tccagcaacc agatactgtg gagcctgatg ccatcaagcc cgtgggaatc agacggctag     2760
acgagaggcc tatccatgct gagccacagt acccagtccg atccgcagcc ccacaccctg     2820
gggatattgg ggacttcatt aatgagggcc ttaaagctgc tgacaacgac cccacggcgc     2880
caccgtatga ctccctctta gtctttgact acgagggcag cggctccacg gctggctcct     2940
tgagctccct caactcctcc agtagcggtg gggaccagga ctatgactac ctgaatgact     3000 ggggacccg cttcaagaaa ctggcggaca tgtacggcgg tggtgacgac tgaacggcag     3060
```

```
gacggacttg gcttttggac aagtatgaac agtttcacct gatattccca aaaaaaagca    3120
tacagaagct aggctttaac tctgtagtcc actagcaccg tgcttgctgg aggctttggc    3180
gtaggctgcg aaccagtttg ggctcccagg gaatatcagt gatccaatac tgtctggaaa    3240
acaccgagct cagctacact tgaattttac agtaaagaag cactgggatt tatgtgcctt    3300
tttgtacctt tttcagattg gaattagttt tctgtttaag gctttaatgg tactgatttc    3360
tgaaatgata aggaaaagac aaaatatttt gtggcgggag cagaaagtta atgtgatac    3420 gcttcaaccc acttttgtta caatgcattt gcttttgtta agatacagaa cgaaacaacc    3480
agattaaaaa aaattaactc atggagtgat tttgttacct ttggggtggg gggatgaga    3540 ccacaagata ggaaaatgta cattacttct agttttagac tttagatttt ttttttttcac  3600 taaaatctta aaacttacgc agctggttgc agataaaggg agttttcata tcaccaattt    3660
gtagcaaaat gaattttttc ataaactaga atgttagaca cattttggtc ttaatccatg    3720
tacacttttt tattttctgt attttttcca cctcgctgta aaatggtgt gtgtacataa     3780 tgtttatcag catagactat ggaggagtgc agagaactcg gaacatgtgt atgtattatt    3840
tggactttgg attcaggttt tttgcatgtt aatatctttc gttatgggta aagtatttac    3900
aaaacaaagt gacatttgat tcaactgttg agctgtagtt agaatactca attttttaatt   3960 ttttaatttt ttttaaattt ttttattttc ttttttgtttg tttcgttttg gggagggta     4020 aaagttctta gcacaatgtt ttacataatt tgtaccaaaa aaattacaca caaaaaaaaa    4080
aaaaagaaaa gaaagaaaaa gtgaaagggg tggcctgttt cttgcagcac tagcaagtgt    4140 gtgttttttaa aaaacaaaac aaacaaacaa aaaataaat aaaaagagga aaagaaaaa    4200 aaaaaaagct tttaaactgg agagacttct gaaacagctt tgcgtctgtg ttgtgtacca    4260
gaatacaaac aatacacctc tgaccccagc gttctgaata aaaagctaat tttggatctg    4320
g                                                                   4321
```

<210> SEQ ID NO 2
<211> LENGTH: 906
<212> TYPE: PRT
<213> ORGANISM: Mus musculus

<400> SEQUENCE: 2

```
Met Cys Arg Ile Ala Gly Ala Pro Arg Thr Leu Leu Pro Leu Leu Ala
1               5                   10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Pro Lys Asp
        35                  40                  45

Val His Glu Gly Gln Pro Leu Leu Asn Val Lys Phe Ser Asn Cys Asn
    50                  55                  60

Arg Lys Arg Lys Val Gln Tyr Glu Ser Ser Glu Pro Ala Asp Phe Lys
65                  70                  75                  80

Val Asp Glu Asp Gly Thr Val Tyr Ala Val Arg Ser Phe Pro Leu Thr
                85                  90                  95

Ala Glu Gln Ala Lys Phe Leu Ile Tyr Ala Gln Asp Lys Glu Thr Gln
            100                 105                 110

Glu Lys Trp Gln Val Ala Val Asn Leu Ser Arg Glu Pro Thr Leu Thr
        115                 120                 125

Glu Glu Pro Met Lys Glu Pro His Glu Ile Glu Glu Ile Val Phe Pro
    130                 135                 140
```

```
Arg Gln Leu Ala Lys His Ser Gly Ala Leu Arg Gln Lys Arg Asp
145                 150                 155                 160

Trp Val Ile Pro Pro Ile Asn Leu Pro Glu Asn Ser Arg Gly Pro Phe
            165                 170                 175

Pro Gln Glu Leu Val Arg Ile Arg Ser Asp Arg Asp Lys Asn Leu Ser
        180                 185                 190

Leu Arg Tyr Ser Val Thr Gly Pro Gly Ala Asp Gln Pro Pro Thr Gly
    195                 200                 205

Ile Phe Ile Ile Asn Pro Ser Gly Gln Leu Ser Val Thr Lys Pro
210                 215                 220

Leu Asp Arg Glu Leu Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
            260                 265                 270

Asn Gly Ser Val Pro Glu Gly Ser Lys Pro Gly Thr Tyr Val Met Thr
        275                 280                 285

Val Thr Ala Ile Asp Ala Asp Pro Asn Ala Leu Asn Gly Met Leu
    290                 295                 300

Arg Tyr Arg Ile Leu Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                325                 330                 335

Leu Asp Arg Glu Lys Val Gln Gln Tyr Thr Leu Ile Ile Gln Ala Thr
            340                 345                 350

Asp Met Glu Gly Asn Pro Thr Tyr Gly Leu Ser Asn Thr Ala Thr Ala
        355                 360                 365

Val Ile Thr Val Thr Asp Val Asn Asp Asn Pro Pro Glu Phe Thr Ala
    370                 375                 380

Met Thr Phe Tyr Gly Glu Val Pro Glu Asn Arg Val Asp Val Ile Val
385                 390                 395                 400

Ala Asn Leu Thr Val Thr Asp Lys Asp Gln Pro His Thr Pro Ala Trp
                405                 410                 415

Asn Ala Ala Tyr Arg Ile Ser Gly Gly Asp Pro Thr Gly Arg Phe Ala
            420                 425                 430

Ile Leu Thr Asp Pro Asn Ser Asn Asp Gly Leu Val Thr Val Val Lys
        435                 440                 445

Pro Ile Asp Phe Glu Thr Asn Arg Met Phe Val Leu Thr Val Ala Ala
    450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                485                 490                 495

Phe Ala Pro Asn Pro Lys Ile Ile Arg Gln Glu Glu Gly Leu His Ala
            500                 505                 510

Gly Thr Met Leu Thr Thr Leu Thr Ala Gln Asp Pro Asp Arg Tyr Met
        515                 520                 525

Gln Gln Asn Ile Arg Tyr Thr Lys Leu Ser Asp Pro Ala Asn Trp Leu
    530                 535                 540

Lys Ile Asp Pro Val Asn Gly Gln Ile Thr Thr Ile Ala Val Leu Asp
545                 550                 555                 560
```

```
Arg Glu Ser Pro Asn Val Lys Asn Asn Ile Tyr Asn Ala Thr Phe Leu
            565                 570                 575
Ala Ser Asp Asn Gly Ile Pro Pro Met Ser Gly Thr Gly Thr Leu Gln
        580                 585                 590
Ile Tyr Leu Leu Asp Ile Asn Asp Asn Ala Pro Gln Val Leu Pro Gln
    595                 600                 605
Glu Ala Glu Thr Cys Glu Thr Pro Glu Pro Asn Ser Ile Asn Ile Thr
610                 615                 620
Ala Leu Asp Tyr Asp Ile Asp Pro Asn Ala Gly Pro Phe Ala Phe Asp
625                 630                 635                 640
Leu Pro Leu Ser Pro Val Thr Ile Lys Arg Asn Trp Thr Ile Asn Arg
                645                 650                 655
Leu Asn Gly Asp Phe Ala Gln Leu Asn Leu Lys Ile Lys Phe Leu Glu
            660                 665                 670
Ala Gly Ile Tyr Glu Val Pro Ile Ile Ile Thr Asp Ser Gly Asn Pro
        675                 680                 685
Pro Lys Ser Asn Ile Ser Ile Leu Arg Val Lys Val Cys Gln Cys Asp
    690                 695                 700
Ser Asn Gly Asp Cys Thr Asp Val Asp Arg Ile Val Gly Ala Gly Leu
705                 710                 715                 720
Gly Thr Gly Ala Ile Ile Ala Ile Leu Leu Cys Ile Ile Ile Leu Leu
                725                 730                 735
Ile Leu Val Leu Met Phe Val Val Trp Met Lys Arg Arg Asp Lys Glu
            740                 745                 750
Arg Gln Ala Lys Gln Leu Leu Ile Asp Pro Glu Asp Asp Val Arg Asp
        755                 760                 765
Asn Ile Leu Lys Tyr Asp Glu Glu Gly Gly Gly Glu Glu Asp Gln Asp
    770                 775                 780
Tyr Asp Leu Ser Gln Leu Gln Gln Pro Asp Thr Val Glu Pro Asp Ala
785                 790                 795                 800
Ile Lys Pro Val Gly Ile Arg Arg Leu Asp Glu Arg Pro Ile His Ala
                805                 810                 815
Glu Pro Gln Tyr Pro Val Arg Ser Ala Ala Pro His Pro Gly Asp Ile
            820                 825                 830
Gly Asp Phe Ile Asn Glu Gly Leu Lys Ala Ala Asp Asn Asp Pro Thr
        835                 840                 845
Ala Pro Pro Tyr Asp Ser Leu Leu Val Phe Asp Tyr Glu Gly Ser Gly
    850                 855                 860
Ser Thr Ala Gly Ser Leu Ser Ser Leu Asn Ser Ser Ser Ser Gly Gly
865                 870                 875                 880
Asp Gln Asp Tyr Asp Tyr Leu Asn Asp Trp Gly Pro Arg Phe Lys Lys
                885                 890                 895
Leu Ala Asp Met Tyr Gly Gly Gly Asp Asp
            900                 905
```

<210> SEQ ID NO 3
<211> LENGTH: 3237
<212> TYPE: DNA
<213> ORGANISM: Xenopus laevis

<400> SEQUENCE: 3

```
tcggcacgag ctggagtgta caggactttt aagatgctgc tgggtgtctg cactgtgtcc      60
atgtgaatgt ggcatttttα ttttgaattc cctccggaga caagatttca tcaagagttt     120
cctttggata ttaagtcaaa gtgcaagcaa tggagattct ctataagaag gcaataatct     180
```

```
gggggattta ctaaaattaa acaaacagat tgacattcgc tggatttatc aagcaatttt        240
gcatttacaa cactaccaaa aatgaagaaa gacttttgct tacacggttt acttttatgt        300
ttgggaattg cgtattgtag tcatgccaca tctttaagaa aaacaataa actaaggcaa         360 tcattccatg gtcaccatga aaaaggcaaa gaagggcaag ttttacatag gtcaaagaga        420
ggatgggttt ggaatcaatt ttttgtaata aagaataca ccggaccaga tcctgtactc         480
gttggacggc ttcactcaga tgttgactct ggagattgga agataaaata catactctca        540
ggagagggtg ctgggaccat ttttgtcatt gatgacaaat cagggaatat ccatgcaacc        600
aagaccctgg atcgagaaga aagggctcag tataccttaa tggctcaggc agttgacaga        660
gaaacaaata aaccactgga accaccatca gagtttatcg ttaaagttca agacataaat        720
gataatcccc cggagttctt gcatgaaaac taccacgcaa atgtgcctga gatgtccaat        780
gtgggtacat cagtaattca gtaacagcc tctgatgcag atgatccaac atatggaaac         840
agcgctaagc ttgtgtatag tattctcgaa gggcagccat attttcagt cgaagcacaa         900 tcaggaatca ttaggactgc ccttccaaac atggacagag aagccaagga agaataccat        960
gttgttattc aagcaaagga tatgggagga catatgggag gactctcagg gacaactaaa        1020
gtgacaataa cgctgacaga tgtcaatgac aatccaccaa agtttccaca aagtgcgtac        1080
cccatgtctg tgtcagaagc tgctgtccca ggggaagagg ttggcagaat aaaagctaaa        1140
gatccagaca ttggagaaaa tggcttaata aagtaccgta ttcttgaagg agatgggca         1200 gagatgtttg aaatcacagc tgattatgta actcaggaag gcgttgtaaa gctaaaaaag        1260
gtggtggatt atgaaaccaa gaagttctac agtatgaagg ttgaagctgt caacgttcat        1320
attgatccca gattccttag ccggggacca ttcaaagaca ctgctactgt taagatctca        1380
gtagaggatt tgatgaacc gcctattttc ttagaaagaa gttacatttt ggaagtatat        1440
gaaaatgctc catcggatac tgtggtcgga agagtgcacg ctaaagaccc agatgctgct        1500
aacagcccaa ttaggtattc aatcgatcgc cacactgacc ttgacagatt cttcagcatc        1560
aacccagagg atggtgtcat caaaaccaca aagggtttgg atagagagga agcccttgg         1620 cacaacatct cagtcattgc aactgaagtc cacaatcgaa ttcatgaaac tagagttcca        1680
gtagctatta aagtcttgga taagaatgac aatgctccgg aatttgcaaa gccctatgaa        1740
gcttttgtct gtgaaaatgc tccaatcaat caggagtttt tgaccatcac tgcagtagat        1800
aaagatgata cagccaatgg acttcgtttt ctctttagtt tcccccaga aattgtacat         1860 ccaaatccaa atttcaccat aatagacaaa cgagataaca cagcaagcat ccgtgttggc        1920
cgtggagttt tcagccgaca gaaacaagac ttgtatttgg ttcctattgt tataagtgat        1980
gggggaagcc caccgatgag cagcaccaat acccttctg tccgaatctg cagttgcaat         2040
agtgatggat cccaactatc ttgtaatgct gaaccccat cccttaacgc tggactcagt         2100
actggagcac tgattgcaat ccttgcttgc attgtaattt tattagtgat gtgggttttg        2160
tttgtgactc tgaggagaga gaagaaggaa cctctaattg tctttgaaga ggaagatatc        2220
cgggaaaata taattacata tgatgatgaa ggtggtggag aggaagacac cgaagcattt        2280
gacattgcaa cactgcagaa tcctgatggg attaatggat ttatgccacg gaaagatatc        2340
aaacccgaat ttcaatataa ccccagagat attggaataa gaccagcacc aaacagtgtt        2400
gacgttgatg acttcattaa cacaaggata catgaggccg ataatgaccc tgcagctccg        2460
ccttatgact ccattcagat ctatggatac gaagggagag ttctgtggc tggctctctt        2520 agttcattag agtcagcctc tacagattca gatttggact atgattatct acaaaactgg        2580
```

```
ggacctcgat ttaagaaact agcaaattta tatgggtcca agacacttg tgaagatgat      2640 tcttaacaaa taagttctga atttggcctt atgaactgca taatgtactg aaatatccag      2700
agtaaacatt aacaggtatt ttttttaaagg aaaacatgaa aaaggcttct ttaaccttcc     2760
aaggtttaca aacaggattc cttccaaaac aagaactgtt aaatggtggt ggatactgtg     2820
aaaaccctat ggcctgtgta gaagttgtgt attcattttt ttttttgttt tttgtttttt     2880
ttccaagaaa ccacttgtaa aatgcagcct atttaaggga atggaaatgc aggaaaaacg     2940
caacaaaaaa ggggaatctt tacagtatta aacataacca tcaaatcttc tcaaacaaag     3000
cttccacaca aaaaaaaaaa aagataacag ttttgagctg taatttcgcc ttaaactatg     3060
gacactttat atgtagtgca tttttaaact tgaaaaaaat atatatataa tatccagcca     3120
gcttcaatcc atataatgta tgtacagtaa aatgtacaat tattctgtct cttgagcatc     3180
agacttgtta ctgctgattc ttgtaaatct tttttgctta taatcccctc gtgccga        3237
```

<210> SEQ ID NO 4
<211> LENGTH: 794
<212> TYPE: PRT
<213> ORGANISM: Xenopus laevis

<400> SEQUENCE: 4

```
Met Lys Lys Asp Phe Cys Leu His Gly Leu Leu Leu Cys Leu Gly Ile
1               5                   10                  15

Ala Tyr Cys Ser His Ala Thr Ser Leu Arg Lys Asn Asn Lys Leu Arg
            20                  25                  30

Gln Ser Phe His Gly His His Glu Lys Gly Lys Glu Gly Gln Val Leu
        35                  40                  45

His Arg Ser Lys Arg Gly Trp Val Trp Asn Gln Phe Phe Val Ile Glu
    50                  55                  60

Glu Tyr Thr Gly Pro Asp Pro Val Leu Val Gly Arg Leu His Ser Asp
65                  70                  75                  80

Val Asp Ser Gly Asp Trp Lys Ile Lys Tyr Ile Leu Ser Gly Glu Gly
                85                  90                  95

Ala Gly Thr Ile Phe Val Ile Asp Asp Lys Ser Gly Asn Ile His Ala
            100                 105                 110

Thr Lys Thr Leu Asp Arg Glu Glu Arg Ala Gln Tyr Thr Leu Met Ala
        115                 120                 125

Gln Ala Val Asp Arg Glu Thr Asn Lys Pro Leu Glu Pro Pro Ser Glu
    130                 135                 140

Phe Ile Val Lys Val Gln Asp Ile Asn Asp Asn Pro Pro Glu Phe Leu
145                 150                 155                 160

His Glu Asn Tyr His Ala Asn Val Pro Glu Met Ser Asn Val Gly Thr
                165                 170                 175

Ser Val Ile Gln Val Thr Ala Ser Asp Ala Asp Asp Pro Thr Tyr Gly
            180                 185                 190

Asn Ser Ala Lys Leu Val Tyr Ser Ile Leu Glu Gly Gln Pro Tyr Phe
        195                 200                 205

Ser Val Glu Ala Gln Ser Gly Ile Ile Arg Thr Ala Leu Pro Asn Met
    210                 215                 220

Asp Arg Glu Ala Lys Glu Glu Tyr His Val Val Ile Gln Ala Lys Asp
225                 230                 235                 240

Met Gly Gly His Met Gly Gly Leu Ser Gly Thr Thr Lys Val Thr Ile
                245                 250                 255
```

-continued

```
Thr Leu Thr Asp Val Asn Asp Asn Pro Pro Lys Phe Pro Gln Ser Ala
            260                 265                 270

Tyr Pro Met Ser Val Ser Glu Ala Ala Val Pro Gly Glu Glu Val Gly
        275                 280                 285

Arg Ile Lys Ala Lys Asp Pro Asp Ile Gly Glu Asn Gly Leu Ile Lys
    290                 295                 300

Tyr Arg Ile Leu Glu Gly Asp Gly Ala Glu Met Phe Glu Ile Thr Ala
305                 310                 315                 320

Asp Tyr Val Thr Gln Glu Gly Val Val Lys Leu Lys Lys Val Val Asp
                325                 330                 335

Tyr Glu Thr Lys Lys Phe Tyr Ser Met Lys Val Glu Ala Val Asn Val
            340                 345                 350

His Ile Asp Pro Arg Phe Leu Ser Arg Gly Pro Phe Lys Asp Thr Ala
        355                 360                 365

Thr Val Lys Ile Ser Val Glu Asp Phe Asp Glu Pro Pro Ile Phe Leu
    370                 375                 380

Glu Arg Ser Tyr Ile Leu Glu Val Tyr Glu Asn Ala Pro Ser Asp Thr
385                 390                 395                 400

Val Val Gly Arg Val His Ala Lys Asp Pro Asp Ala Ala Asn Ser Pro
                405                 410                 415

Ile Arg Tyr Ser Ile Asp Arg His Thr Asp Leu Asp Arg Phe Phe Ser
            420                 425                 430

Ile Asn Pro Glu Asp Gly Val Ile Lys Thr Thr Lys Gly Leu Asp Arg
        435                 440                 445

Glu Glu Ser Pro Trp His Asn Ile Ser Val Ile Ala Thr Glu Val His
    450                 455                 460

Asn Arg Ile His Glu Thr Arg Val Pro Val Ala Ile Lys Val Leu Asp
465                 470                 475                 480

Lys Asn Asp Asn Ala Pro Glu Phe Ala Lys Pro Tyr Glu Ala Phe Val
                485                 490                 495

Cys Glu Asn Ala Pro Ile Asn Gln Glu Phe Leu Thr Ile Thr Ala Val
            500                 505                 510

Asp Lys Asp Asp Thr Ala Asn Gly Leu Arg Phe Leu Phe Ser Phe Pro
        515                 520                 525

Pro Glu Ile Val His Pro Asn Pro Asn Phe Thr Ile Ile Asp Lys Arg
    530                 535                 540

Asp Asn Thr Ala Ser Ile Arg Val Gly Arg Gly Val Phe Ser Arg Gln
545                 550                 555                 560

Lys Gln Asp Leu Tyr Leu Val Pro Ile Val Ile Ser Asp Gly Gly Ser
                565                 570                 575

Pro Pro Met Ser Ser Thr Asn Thr Leu Ser Val Arg Ile Cys Ser Cys
            580                 585                 590

Asn Ser Asp Gly Ser Gln Leu Ser Cys Asn Ala Glu Pro Gln Ser Leu
        595                 600                 605

Asn Ala Gly Leu Ser Thr Gly Ala Leu Ile Ala Ile Leu Ala Cys Ile
    610                 615                 620

Val Ile Leu Leu Val Ile Val Val Leu Phe Val Thr Leu Arg Arg Glu
625                 630                 635                 640

Lys Lys Glu Pro Leu Ile Val Phe Glu Glu Asp Ile Arg Glu Asn
                645                 650                 655

Ile Ile Thr Tyr Asp Asp Glu Gly Gly Gly Glu Glu Asp Thr Glu Ala
            660                 665                 670

Phe Asp Ile Ala Thr Leu Gln Asn Pro Asp Gly Ile Asn Gly Phe Met
```

```
                675                 680                 685
Pro Arg Lys Asp Ile Lys Pro Glu Phe Gln Tyr Asn Pro Arg Asp Ile
            690                 695                 700
Gly Ile Arg Pro Ala Pro Asn Ser Val Asp Val Asp Phe Ile Asn
705                 710                 715                 720
Thr Arg Ile His Glu Ala Asp Asn Asp Pro Ala Pro Pro Tyr Asp
                725                 730                 735
Ser Ile Gln Ile Tyr Gly Tyr Glu Gly Arg Gly Ser Val Ala Gly Ser
            740                 745                 750
Leu Ser Ser Leu Glu Ser Ala Ser Thr Asp Ser Asp Leu Asp Tyr Asp
                755                 760                 765
Tyr Leu Gln Asn Trp Gly Pro Arg Phe Lys Lys Leu Ala Asn Leu Tyr
    770                 775                 780
Gly Ser Lys Asp Thr Cys Glu Asp Asp Ser
785                 790

<210> SEQ ID NO 5
<211> LENGTH: 3701
<212> TYPE: DNA
<213> ORGANISM: Mus musculus

<400> SEQUENCE: 5
```

| | | | | | |
|---|---|---|---|---|---|
| gtccaatcag | tgcgctcaga | ctcagagccc | taggctcctg | ctctttaaat | taccgagcct | 60 |
| tgtggagacc | ccggcacctg | gccttaagct | cagccctgag | gatggtactt | tgagtgaatg | 120 |
| accaccttgg | agaccgttct | tctgtttccc | ttgttaccag | ccaggaggca | gaagagtcca | 180 |
| ccggtccagg | aaagacccat | ttcccttgag | tttccagaaa | gtacctcatg | cttgagagat | 240 |
| caggccaaca | actatggctc | tcgtcttcag | tgccctgctg | ttactggggc | tgtgtggaaa | 300 |
| gatctcttca | gaaggtcagc | ctgcattcca | taacactcct | ggggctatga | attatgaatt | 360 |
| gcctaccacc | aaatatgaga | cccaagatac | cttcaatgct | gggattgttg | gccctctcta | 420 |
| caaaatggtg | cacatcttcc | tcaacgtggt | ccagccgaat | gacttccctc | tagatttgat | 480 |
| caaaaaactc | atacagaaca | gaactttga | catctcagtt | gattccaagg | agccagaaat | 540 |
| catagtcttg | gctctgaaga | ttgccctcta | tgagatcgga | gtcctatct | gcgccatcct | 600 |
| gggactgctg | ttcattatcc | tcatgcctct | ggtgggctgc | ttcttttgta | tgtgccgttg | 660 |
| ctgcaacaaa | tgcggcggag | agatgcacca | gcggcagaag | cagaatgcgc | catgcaggag | 720 |
| gaagtgcttg | ggcctctccc | tcctggtgat | ttgtctgctc | atgagccttg | gcattatata | 780 |
| tggctttgtg | gctaaccagc | agaccaggac | tcggatcaaa | gggacccaga | actggcaaa | 840 |
| gagcaatttc | agagactttc | aaacactcct | gactgaaaca | ccaaagcaaa | ttgactatgt | 900 |
| agtggagcag | taccaccaaca | ccaagaacaa | ggcattctca | gacctggatg | catcggctc | 960 |
| cgtgctggga | ggcagaataa | aggaccaact | aaaacccaaa | gtaactcctg | tcctcgaaga | 1020 |
| gattaaggcc | atggcgacag | ccatcaaaca | gaccaaggat | gccctgcaga | acatgagcag | 1080 |
| cagcctgaaa | agtctccaag | atgcagccac | ccagctcaat | accaacctga | gctctgtgag | 1140 |
| aaacagcatc | gagaattcgc | tcagcagcag | tgactgtacc | tcagatccag | ccagcaagat | 1200 |
| ctgcgatagc | atcagaccaa | gcctaagcag | tctggggagc | agcctcaatt | caagtcagct | 1260 |
| cccatcagtg | gatagagaac | tcaacactgt | tactgaagtc | gacaaaactg | atctggagag | 1320 |
| cctcgtcaaa | agggggtata | cgacaattga | tgaaatacc | aatacaatac | aaaaccaaac | 1380 |
| tgtggatgtc | atcaaagacg | tcaaaaatac | cttggactcc | attagctcca | acattaagga | 1440 |

```
catgagccaa agtattccta ttgaggatat gctgttacag gtctcccatt accttaataa    1500
cagcaacaga tacttaaacc aggagctgcc caagctggaa gaatatgact cgtactggtg    1560
gctgggtggc ttgattgtct gctttctgct gactctcatt gtgaccttct ttttcctggg    1620
cttgctgtgt ggtgtgtttg gctatgacaa gcatgccacc ccaactagaa gaggctgtgt    1680
gtccaacact ggaggcatct tcctcatggc tggggttgga ttcggcttcc ttttttgctg    1740
gatattgatg atccttgtgg ttcttacgtt tgttgttggt gcaaatgtgg aaaagttgct    1800
ctgcgaacct tatgaaaaca gaaaattatt acaggttttg gacactccct atctgctcaa    1860
ggaacaatgg caattttatc tttctggcat gctattcaat aacccagaca ttaacatgac    1920 cttttgagcaa gtctacaggg attgcaaaag aggtcgaggt atatatgctg cttttcagct    1980
tgagaatgtc gtcaacgtca gtgatcattt caacattgac cagatttctg aaaacataaa    2040
tacggagttg gaaaacctga atgtgaacat tgatagcatt gaactgttgg ataacacagg    2100
aaggaagagc ctcgaggact ttgcacattc tgggatagat acaatcgatt attccacata    2160
cttgaaggag actgagaaat cccctactga agtgaatctg ctgacatttg cctctaccct    2220
ggaagcaaaa gcaaaccagt tgcctgaagg aaagctgaaa caggccttct tactggatgt    2280
acagaatata gagccatcc accagcatct cctccctcct gtgcagcaat cactgaaatt    2340
tgtgagggtg aggaatacgt taagacaaag tgtctggacc ctccagcaaa caagcaacaa    2400
gttgccggag aaagtgaaga gatccttgc ctctttggac tctgttcagc atttcctcac    2460
caataacgtt tccctcatcg ttatcgggga aacgaagaag tttgggaaaa caatactagg    2520
ctactttgaa cattatctgc actgggtctt ttatgccatc acagagaaga tgacatcctg    2580
caaacccatg gccaccgcga tggactctgc tgttaatggc attctgtgtg gctatgttgc    2640
ggaccctctg aatttgttct ggttcggcat agggaaagcc acggtgctct acttccggc    2700 tgtaatcatt gctatcaagc tggccaagta ctatcgcagg atggattcag aggatgtata    2760
cgacgacccg tctcgatact gacaactgga gttgaagctg cttgaacaac aagatagtca    2820
acatggaaag catcacagat tttggatagt ttctgagtct tctagaacgt tccaagtgca    2880
gaagaaacct ggtggagact caggcgggca ctaggaacat ggcatcagtg gtcttagggt    2940
agcactttgt caggaatgaa cagtcatcat ggttataatc cacatatcca ttgcaactca    3000
tgaatgattc tctcctgttt tgttttaac ttttctttt acactgattt tctatttaga      3060
cactaaaaca tataggggtg cttattcccc ctggatacat ttacctgtga accagctatt    3120
ccggtgtcat agctgggtac ctaacttact tccatatgtg aagtgtgcta acacaaaacc    3180
agtttacaga agagatgtat tttgtgtata gtaaactgta tatataccct tttaccacag    3240
tcagtttttt aaacaaatga atactctaga tttttcttct aaatgaggtt actgttgggg    3300
tggttgtgac ctagtgatgc tgtagaaagg agtctgcatt cactaaaagt gtgtcaacct    3360
agagcaggca atgcccttcc ttgtggattt ctgtctgctc gttttggagc tacctgcggt    3420
ttagaaatag aattcaagaa caatcacgga gtttcccact tgatgccact gccaaagtca    3480
gaacaaggga tcttgagaga aggaactgtc gctcagctgg gagcggaatc attatcgcaa    3540
tcacaggtcc tggttcacag tttagtggca ctctctggtt tgtaagaatg ggcattacgt    3600
tcagtgtcat ctggtcatct gtgatgtgtg tcatcagcct gtcctgatgt tgagatttaa    3660
aataaagcat gaatgaacag aaaaaaaaaa aaaaaaaaaa a                        3701
```

<210> SEQ ID NO 6
<211> LENGTH: 842

```
<212> TYPE: PRT
<213> ORGANISM: Mus musculus

<400> SEQUENCE: 6

Met Ala Leu Val Phe Ser Ala Leu Leu Leu Gly Leu Cys Gly Lys
1               5                   10                  15

Ile Ser Ser Glu Gly Gln Pro Ala Phe His Asn Thr Pro Gly Ala Met
            20                  25                  30

Asn Tyr Glu Leu Pro Thr Thr Lys Tyr Glu Thr Gln Asp Thr Phe Asn
            35                  40                  45

Ala Gly Ile Val Gly Pro Leu Tyr Lys Met Val His Ile Phe Leu Asn
        50                  55                  60

Val Val Gln Pro Asn Asp Phe Pro Leu Asp Leu Ile Lys Lys Leu Ile
65                  70                  75                  80

Gln Asn Lys Asn Phe Asp Ile Ser Val Asp Ser Lys Glu Pro Glu Ile
                85                  90                  95

Ile Val Leu Ala Leu Lys Ile Ala Leu Tyr Glu Ile Gly Val Leu Ile
            100                 105                 110

Cys Ala Ile Leu Gly Leu Leu Phe Ile Ile Leu Met Pro Leu Val Gly
        115                 120                 125

Cys Phe Phe Cys Met Cys Arg Cys Cys Asn Lys Cys Gly Gly Glu Met
130                 135                 140

His Gln Arg Gln Lys Gln Asn Ala Pro Cys Arg Arg Lys Cys Leu Gly
145                 150                 155                 160

Leu Ser Leu Leu Val Ile Cys Leu Leu Met Ser Leu Gly Ile Ile Tyr
                165                 170                 175

Gly Phe Val Ala Asn Gln Gln Thr Arg Thr Arg Ile Lys Gly Thr Gln
            180                 185                 190

Lys Leu Ala Lys Ser Asn Phe Arg Asp Phe Gln Thr Leu Leu Thr Glu
        195                 200                 205

Thr Pro Lys Gln Ile Asp Tyr Val Val Glu Gln Tyr Thr Asn Thr Lys
210                 215                 220

Asn Lys Ala Phe Ser Asp Leu Asp Gly Ile Gly Ser Val Leu Gly Gly
225                 230                 235                 240

Arg Ile Lys Asp Gln Leu Lys Pro Lys Val Thr Pro Val Leu Glu Glu
                245                 250                 255

Ile Lys Ala Met Ala Thr Ala Ile Lys Gln Thr Lys Asp Ala Leu Gln
            260                 265                 270

Asn Met Ser Ser Ser Leu Lys Ser Leu Gln Asp Ala Ala Thr Gln Leu
        275                 280                 285

Asn Thr Asn Leu Ser Ser Val Arg Asn Ser Ile Glu Asn Ser Leu Ser
290                 295                 300

Ser Ser Asp Cys Thr Ser Asp Pro Ala Ser Lys Ile Cys Asp Ser Ile
305                 310                 315                 320

Arg Pro Ser Leu Ser Ser Leu Gly Ser Ser Leu Asn Ser Ser Gln Leu
                325                 330                 335

Pro Ser Val Asp Arg Glu Leu Asn Thr Val Thr Glu Val Asp Lys Thr
            340                 345                 350

Asp Leu Glu Ser Leu Val Lys Arg Gly Tyr Thr Thr Ile Asp Glu Ile
        355                 360                 365

Pro Asn Thr Ile Gln Asn Gln Thr Val Asp Val Ile Lys Asp Val Lys
370                 375                 380

Asn Thr Leu Asp Ser Ile Ser Ser Asn Ile Lys Asp Met Ser Gln Ser
385                 390                 395                 400
```

```
Ile Pro Ile Glu Asp Met Leu Leu Gln Val Ser His Tyr Leu Asn Asn
            405                 410                 415

Ser Asn Arg Tyr Leu Asn Gln Glu Leu Pro Lys Leu Glu Glu Tyr Asp
            420                 425                 430

Ser Tyr Trp Trp Leu Gly Gly Leu Ile Val Cys Phe Leu Leu Thr Leu
            435                 440                 445

Ile Val Thr Phe Phe Phe Leu Gly Leu Leu Cys Gly Val Phe Gly Tyr
        450                 455                 460

Asp Lys His Ala Thr Pro Thr Arg Arg Gly Cys Val Ser Asn Thr Gly
465                 470                 475                 480

Gly Ile Phe Leu Met Ala Gly Val Gly Phe Gly Phe Leu Phe Cys Trp
                485                 490                 495

Ile Leu Met Ile Leu Val Val Leu Thr Phe Val Val Gly Ala Asn Val
                500                 505                 510

Glu Lys Leu Leu Cys Glu Pro Tyr Glu Asn Lys Lys Leu Leu Gln Val
        515                 520                 525

Leu Asp Thr Pro Tyr Leu Leu Lys Glu Gln Trp Gln Phe Tyr Leu Ser
    530                 535                 540

Gly Met Leu Phe Asn Asn Pro Asp Ile Asn Met Thr Phe Glu Gln Val
545                 550                 555                 560

Tyr Arg Asp Cys Lys Arg Gly Arg Gly Ile Tyr Ala Ala Phe Gln Leu
                565                 570                 575

Glu Asn Val Val Asn Val Ser Asp His Phe Asn Ile Asp Gln Ile Ser
            580                 585                 590

Glu Asn Ile Asn Thr Glu Leu Glu Asn Leu Asn Val Asn Ile Asp Ser
            595                 600                 605

Ile Glu Leu Leu Asp Asn Thr Gly Arg Lys Ser Leu Glu Asp Phe Ala
    610                 615                 620

His Ser Gly Ile Asp Thr Ile Asp Tyr Ser Thr Tyr Leu Lys Glu Thr
625                 630                 635                 640

Glu Lys Ser Pro Thr Glu Val Asn Leu Leu Thr Phe Ala Ser Thr Leu
                645                 650                 655

Glu Ala Lys Ala Asn Gln Leu Pro Glu Gly Lys Leu Lys Gln Ala Phe
            660                 665                 670

Leu Leu Asp Val Gln Asn Ile Arg Ala Ile His Gln His Leu Leu Pro
            675                 680                 685

Pro Val Gln Gln Ser Leu Lys Phe Val Arg Val Arg Asn Thr Leu Arg
    690                 695                 700

Gln Ser Val Trp Thr Leu Gln Gln Thr Ser Asn Lys Leu Pro Glu Lys
705                 710                 715                 720

Val Lys Lys Ile Leu Ala Ser Leu Asp Ser Val Gln His Phe Leu Thr
                725                 730                 735

Asn Asn Val Ser Leu Ile Val Ile Gly Glu Thr Lys Lys Phe Gly Lys
            740                 745                 750

Thr Ile Leu Gly Tyr Phe Glu His Tyr Leu His Trp Val Phe Tyr Ala
        755                 760                 765

Ile Thr Glu Lys Met Thr Ser Cys Lys Pro Met Ala Thr Ala Met Asp
    770                 775                 780

Ser Ala Val Asn Gly Ile Leu Cys Gly Tyr Val Ala Asp Pro Leu Asn
785                 790                 795                 800

Leu Phe Trp Phe Gly Ile Gly Lys Ala Thr Val Leu Leu Leu Pro Ala
                805                 810                 815
```

```
Val Ile Ile Ala Ile Lys Leu Ala Lys Tyr Tyr Arg Arg Met Asp Ser
            820                 825                 830

Glu Asp Val Tyr Asp Asp Pro Ser Arg Tyr
        835                 840

<210> SEQ ID NO 7
<211> LENGTH: 3306
<212> TYPE: DNA
<213> ORGANISM: Mus musculus

<400> SEQUENCE: 7
gaattcccgc gcggccgcca gagctccggc ccgggggctg cctgtgtgtt cctggcccgg      60
cgtggcgact gctctccggg ctggcggggg ccggcgtga gcccgggcct cagcgttcct     120
gagcgctgcg agtgttcact actcgccagc aaagtttgga gtaggcaacg caagctccag     180
tcctttcttc tgctgctgcc cagatccgag agcagctccg gtgtatgtct agctgttctg     240
cgatcccggc gcgcgtgaag cctcggaacc ttggcgccgg ctgctaccca aggaatcgtt     300 ctcttttttgg agttttcctc cgagatcatc gcctgctcca tcccgatcca ctctgggctc     360
cggcgcagca ccgagcgcag aggagcgctg ccattcaagt ggcagccaca gcagcagcag     420
cagcagcagt gggagcagga acagcagtaa aacagcaac agcagcacag ccgcctcaga     480
gctttgctcc tgagcccctg tgggctgaag gcattgcagg tagcccatgg tctcagaaga     540
agtgtgcaga tgggattacc gtccacgtgg agatatggaa aggaccagg gattggcact     600 gtgaccatgg tcagctgggg gcgcttcatc tgcctggtct tggtcaccat ggcaaccttg     660
tccctggccc ggccctcctt cagtttagtt gaggatacca ctttagaacc agaagagcca     720
ccaaccaaat accaaatctc ccaaccagaa gcgtacgtgg ttgccccgg gaatcgcta      780 gagttgcagt gcatgttgaa agatgccgcc gtgatcagtt ggactaagga tggggtgcac     840
ttggggccca acaataggac agtgcttatt ggggagtatc tccagataaa aggtgccaca     900
cctagagact ccgccctcta tgcttgtact gcagctagga cggtagacag tgaaacttgg     960
atcttcatgg tgaatgtcac agatgccatc tcatctggag atgatgagga cgacacagat    1020
agctccgaag acgttgtcag tgagaacagg agcaaccaga gagcaccgta ctggaccaac    1080
accgagaaga tggagaagcg gctccacgct tgtcctgccg ccaacactgt gaagttccgc    1140
tgtccggctg gggggaatcc aacgtccaca atgaggtggt taaaaaacgg gaaggagttt    1200
aagcaggagc atcgcattgg aggctataag gtacgaaacc agcactggag ccttattatg    1260
gaaagtgtgg tcccgtcaga caaaggcaac tacacctgcc tggtggagaa tgaatacggg    1320
tccatcaacc acacctacca cctggatgtc gttgaacgtt caccacaccg tcccatcctc    1380
caagctggac tgcctgcaaa tgcctccacg gtggtcggag gggatgtgga gtttgtctgc    1440
aaggtttaca gcgatgccca gccccacatc cagtggatca agcacgtgga aaagaacggc    1500
agtaaaaacg ggcctgatgg gctgccctac ctcaaggttc tgaaagctgc cggtgttaac    1560
accacggaca aagagattga ggttctctat attcggaatg taacttttga ggatgctggg    1620
gaatatacgt gcttggcggg taattctatc gggatatcct ttcactctgc atggttgaca    1680
gttctgccag cgcctgtgag agagaaggag atcacggctt ccccagatta tctgagaata    1740
gctatttact gcataggggt cttcttaatc gcctgcatgg tggtgacagt catcttttgc    1800
cgaatgaaga ccacgaccaa gaagccagac ttcagcagcc agccagctgt gcacaagctg    1860
accaagcgca tccccctgcg gagacaggta acagttcgg ccgagtccag ctcctccatg    1920
aactccaaca ccccgctggt gaggataaca acgcgtctgt cctcaacagc ggacacccg     1980
```

```
atgctagcag gggtctccga gtatgagttg ccagaggatc caaagtggga attccccaga   2040
gataagctga cgctgggcaa acccctgggg gaaggttgct tcgggcaagt agtcatggct   2100
gaagcagtgg gaatcgataa agacaaaccc aaggaggcgg tcaccgtggc agtgaagatg   2160
ttgaaagatg atgccacaga gaaggacctg tctgatctgg tatcagagat ggagatgatg   2220
aagatgattg ggaaacataa gaacattatc aacctcctgg gggcctgcac gcaggatgga   2280
cctctctacg tcatagttga atatgcatcg aaaggcaacc tccgggaata cctccgagcc   2340
cggaggccac ctggcatgga gtactcctat gacattaacc gtgtccccga ggagcagatg   2400
accttcaagg acttggtgtc ctgcacctac cagctggcta gaggcatgga gtacttggct   2460
tcccaaaaat gtatccatcg agatttggct gccagaaacg tgttggtaac agaaaacaat   2520
gtgatgaaga tagcagactt tggcctggcc agggatatca acaacataga ctactataaa   2580
aagaccacaa atgggcgact tccagtcaag tggatggctc ctgaagccct ttttgataga   2640
gtttacactc atcagagcga tgtctggtcc ttcggggtgt taatgtggga gatctttact   2700 ttaggggct caccctaccc agggattccc gtggaggaac ttttttaagct gctcaaagag   2760 ggacacagga tggacaagcc caccaactgc accaatgaac tgtacatgat gatgagggat   2820
tgctggcatg ctgtaccctc acagagaccc acattcaagc agttggtcga agacttggat   2880
cgaattctga ctctcacaac caatgaggaa tacttggatc tcacccagcc tctcgaacag   2940
tattctccta gttaccccga cacaagtagc tcttgttctt caggggacga ttctgtgttt   3000
tctccagacc ccatgcctta tgaaccctgt ctgcctcagt atccacacat aaacggcagt   3060
gttaaaacat gagtgaatgt gtcttcctgt ccccaaacag gacagcacca ggaacctact   3120
tacactgagc agagaggctg tgctccagag cctgtgacac gcctccactt gtatatatgg   3180
atcagaggag taaatagtgg gaagcatatt tgtcacgtgt gtaaagattt atacagttgg   3240
aacatgtact acaggaagga gactgttctg atagtgacag ccgccaccat gccacctttg   3300
accaca                                                            3306
```

<210> SEQ ID NO 8
<211> LENGTH: 821
<212> TYPE: PRT
<213> ORGANISM: Mus musculus

<400> SEQUENCE: 8

```
Met Val Ser Trp Gly Arg Phe Ile Cys Leu Val Leu Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Ala Tyr Val Val Ala Pro Gly Glu Ser Leu Glu Leu Gln Cys Met Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ala Arg Thr
            100                 105                 110

Val Asp Ser Glu Thr Trp Ile Phe Met Val Asn Val Thr Asp Ala Ile
        115                 120                 125
```

Ser Ser Gly Asp Asp Glu Asp Thr Asp Ser Ser Glu Asp Val Val
130                 135                 140

Ser Glu Asn Arg Ser Asn Gln Arg Ala Pro Tyr Trp Thr Asn Thr Glu
145                 150                 155                 160

Lys Met Glu Lys Arg Leu His Ala Cys Pro Ala Ala Asn Thr Val Lys
            165                 170                 175

Phe Arg Cys Pro Ala Gly Asn Pro Thr Ser Thr Met Arg Trp Leu
        180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
210                 215                 220

Asp Lys Gly Asn Tyr Thr Cys Leu Val Glu Asn Glu Tyr Gly Ser Ile
225                 230                 235                 240

Asn His Thr Tyr His Leu Asp Val Val Glu Arg Ser Pro His Arg Pro
            245                 250                 255

Ile Leu Gln Ala Gly Leu Pro Ala Asn Ala Ser Thr Val Val Gly Gly
        260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Asn Gly Pro Asp
        290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
            325                 330                 335

Ala Gly Glu Tyr Thr Cys Leu Ala Gly Asn Ser Ile Gly Ile Ser Phe
        340                 345                 350

His Ser Ala Trp Leu Thr Val Leu Pro Ala Pro Val Arg Glu Lys Glu
        355                 360                 365

Ile Thr Ala Ser Pro Asp Tyr Leu Glu Ile Ala Ile Tyr Cys Ile Gly
        370                 375                 380

Val Phe Leu Ile Ala Cys Met Val Val Thr Val Ile Phe Cys Arg Met
385                 390                 395                 400

Lys Thr Thr Thr Lys Lys Pro Asp Phe Ser Ser Gln Pro Ala Val His
            405                 410                 415

Lys Leu Thr Lys Arg Ile Pro Leu Arg Arg Gln Val Thr Val Ser Ala
        420                 425                 430

Glu Ser Ser Ser Ser Met Asn Ser Asn Thr Pro Leu Val Arg Ile Thr
        435                 440                 445

Thr Arg Leu Ser Ser Thr Ala Asp Thr Pro Met Leu Ala Gly Val Ser
450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
            485                 490                 495

Met Ala Glu Ala Val Gly Ile Asp Lys Asp Lys Pro Lys Glu Ala Val
        500                 505                 510

Thr Val Ala Val Lys Met Leu Lys Asp Asp Ala Thr Glu Lys Asp Leu
        515                 520                 525

Ser Asp Leu Val Ser Glu Met Glu Met Met Lys Met Ile Gly Lys His
530                 535                 540

Lys Asn Ile Ile Asn Leu Leu Gly Ala Cys Thr Gln Asp Gly Pro Leu

-continued

```
            545                 550                 555                 560
        Tyr Val Ile Val Glu Tyr Ala Ser Lys Gly Asn Leu Arg Glu Tyr Leu
                        565                 570                 575
        Arg Ala Arg Arg Pro Pro Gly Met Glu Tyr Ser Tyr Asp Ile Asn Arg
                        580                 585                 590
        Val Pro Glu Glu Gln Met Thr Phe Lys Asp Leu Val Ser Cys Thr Tyr
                        595                 600                 605
        Gln Leu Ala Arg Gly Met Glu Tyr Leu Ala Ser Gln Lys Cys Ile His
                        610                 615                 620
        Arg Asp Leu Ala Ala Arg Asn Val Leu Val Thr Glu Asn Asn Val Met
        625                 630                 635                 640
        Lys Ile Ala Asp Phe Gly Leu Ala Arg Asp Ile Asn Asn Ile Asp Tyr
                        645                 650                 655
        Tyr Lys Lys Thr Thr Asn Gly Arg Leu Pro Val Lys Trp Met Ala Pro
                        660                 665                 670
        Glu Ala Leu Phe Asp Arg Val Tyr Thr His Gln Ser Asp Val Trp Ser
                        675                 680                 685
        Phe Gly Val Leu Met Trp Glu Ile Phe Thr Leu Gly Gly Ser Pro Tyr
                        690                 695                 700
        Pro Gly Ile Pro Val Glu Glu Leu Phe Lys Leu Leu Lys Glu Gly His
        705                 710                 715                 720
        Arg Met Asp Lys Pro Thr Asn Cys Thr Asn Glu Leu Tyr Met Met Met
                        725                 730                 735
        Arg Asp Cys Trp His Ala Val Pro Ser Gln Arg Pro Thr Phe Lys Gln
                        740                 745                 750
        Leu Val Glu Asp Leu Asp Arg Ile Leu Thr Leu Thr Thr Asn Glu Glu
                        755                 760                 765
        Tyr Leu Asp Leu Thr Gln Pro Leu Glu Gln Tyr Ser Pro Ser Tyr Pro
                        770                 775                 780
        Asp Thr Ser Ser Ser Cys Ser Ser Gly Asp Asp Ser Val Phe Ser Pro
        785                 790                 795                 800
        Asp Pro Met Pro Tyr Glu Pro Cys Leu Pro Gln Tyr Pro His Ile Asn
                        805                 810                 815
        Gly Ser Val Lys Thr
                        820

<210> SEQ ID NO 9
<211> LENGTH: 3037
<212> TYPE: DNA
<213> ORGANISM: Mus musculus

<400> SEQUENCE: 9
ggcgagggga gagagccggg agaggcgagc ggcggcgcgg caggcgcgga acgggcgcac      60
ggacgatcga acgcgcggcc gccagagctc cggcgcgggg gctgcctgtg tgttcctggc     120
ccggcgtggc gactgctctc cgggctggcg ggggccgggc gtgagcccgg gcctcagcgt     180
tcctgagcgc tgcgagtgtt cactactcgc cagcaaagtt tggagtaggc aacgccaagc     240
tccagtcctt tcttctgctg ctgcccagat ccgagagcag ctccggtgtc atgtcctagc     300
tgttctgcga tccccggcgc gcgtgaagcc tcggaacctt cgcgccggct gctacccaag     360
gaatcgttct cttttttggag ttttcctccg agatcatcgc ctgctccatc ccgatccact     420
ctgggctccg gcgcagaccg agcgcagagg agcgctgcca ttcaagtggc agccacagca     480
gcagcagcag cagcagtggg agcaggaaca gcagtaacaa cagcaacagc agcacagccg     540
```

|  |  |  |  |  |  |
|---|---|---|---|---|---|
| cctcagagct | ttggctcctg | agcccctgt | gggctgaagg | cattgcaggt | agcccatggt | 600 |
| ctcagaagaa | gtgtgcagat | gggattaccg | tccacgtgga | gatatggaag | aggaccaggg | 660 |
| attggcactg | tgaccatggt | cagctggggg | cgcttcatct | gcctggtctt | ggtcaccatg | 720 |
| gcaaccttgt | ccctggcccg | gccctccttc | agtttagttg | aggataccac | tttagaacca | 780 |
| gaaggagcac | cgtactggac | caacaccgag | aagatggaga | agcggctcca | cgctgtccct | 840 |
| gccgccaaca | ctgtgaagtt | ccgctgtccg | gctgggggga | atccaacgcc | acaatgagg | 900 |
| tggttaaaaa | acgggaagga | gtttaagcag | gagcatcgca | ttggaggcta | aaggtacga | 960 |
| aaccagcact | ggagccttat | tatggaaagt | gtggtcccgt | cagacaaagg | caactacacc | 1020 |
| tgcctggtgg | agaatgaata | cgggtccatc | aaccacacct | accacctcga | tgtcgttgaa | 1080 |
| cggtcaccac | accggcccat | cctccaagct | ggactgcctg | caaatgcctc | cacggtggtc | 1140 |
| ggaggggatg | tggagtttgt | ctgcaaggtt | tacagcgatg | cccagcccca | catccagtgg | 1200 |
| atcaagcacg | tggaaaagaa | cggcagtaaa | tacgggcctg | atgggctgcc | ctacctcaag | 1260 |
| gtcctgaagc | actcggggat | aaatagctcc | aatgcagaag | tgctggctct | gttcaatgtg | 1320 |
| acggagatgg | atgctgggga | atatatatgt | aaggtctcca | attatatagg | gcaggccaac | 1380 |
| cagtctgcct | ggctcactgt | cctgcccaaa | cagcaagcgc | ctgtgagaga | aaggagatc | 1440 |
| acggcttccc | cagattatct | ggagatagct | atttactgca | taggggtctt | cttaatcgcc | 1500 |
| tgcatggtgg | tgacagtcat | cttttgccga | atgaagacca | cgaccaagaa | gccagacttc | 1560 |
| agcagccagc | cagctgtgca | caagctgacc | aagcgcatcc | ccctgcggag | acaggtaaca | 1620 |
| gtttcggccg | agtccagctc | ctccatgaac | tccaacaccc | cgctggtgag | gataacaacg | 1680 |
| cgtctgtcct | caacagcgga | caccccgatg | ctagcagggg | tctccgagta | tgagttgcca | 1740 |
| gaggatccaa | agtgggaatt | ccccagagat | aagctgacgc | tggcaaaacc | cctgggggaa | 1800 |
| ggttgcttcg | ggcaagtagt | catggctgaa | gcagtgggaa | tcgataaaga | caaacccaag | 1860 |
| gaggcggtca | ccgtggcagt | gaagatgttg | aaagatgatg | ccacagagaa | ggacctgtct | 1920 |
| gatctggtat | cagagatgga | gatgatgaag | atgattggga | aacataagaa | cattatcaac | 1980 |
| ctcctggggg | cctgcacgca | ggatggacct | ctctacgtca | tagttgaata | tgcatcgaaa | 2040 |
| ggcaacctcc | gggaatacct | ccgagcccgg | aggccacctg | gcatggagta | ctcctatgac | 2100 |
| attaaccgtg | tccccgagga | gcagatgacc | ttcaaggact | tggtgtcctg | cacctaccag | 2160 |
| ctggctagag | gcatggagta | cttggcttcc | caaaaatgta | tccatcgaga | tttggctgcc | 2220 |
| agaaacgtgt | tggtaacaga | aaacaatgtg | atgaagatag | cagactttgg | cctggccagg | 2280 |
| gatatcaaca | acatagacta | ctataaaaag | accacaaatg | ggcgacttcc | agtcaagtgg | 2340 |
| atggctcctg | aagcccttt | tgatagagtt | tacactcatc | agagcgatgt | ctggtccttc | 2400 |
| ggggtgttaa | tgtgggagat | ctttacttta | gggggctcac | cctacccagg | gattcccgtg | 2460 |
| gaggaacttt | ttaagctgct | caaagaggga | cacaggatgg | acaagccac | caactgcacc | 2520 |
| aatgaactgt | acatgatgat | gagggattgc | tggcatgctg | taccctcaca | gagacccaca | 2580 |
| ttcaagcagt | tggtcgaaga | cttggatcga | attctgactc | tcacaaccaa | tgaggaatac | 2640 |
| ttggatctca | cccagcctct | cgaacagtat | tctcctagtt | accccgacac | aaggagctct | 2700 |
| tgttcttcag | gggacgattc | tgtgttttct | ccagacccca | tgccttatga | accctgtctg | 2760 |
| cctcagtatc | cacacataaa | cggcagtgtt | aaaacatgag | tgaatgtgtc | ttcctgtccc | 2820 |
| caaacaggac | agcaccagga | acctacttac | actgagcaga | gaggctgtct | cagagcctgt | 2880 |
| gacacgcctc | cacttgtata | tatggatcag | aggagtaaat | agtgggaagc | atattgtcac | 2940 | gtgtgtaaag atttatacag ttcggaaaca tgttacctaa ccaggaaagg aagactgttt     3000 tcctgataag tggacagccg caagccacca tgccacc                              3037

<210> SEQ ID NO 10
<211> LENGTH: 707
<212> TYPE: PRT
<213> ORGANISM: Mus musculus

<400> SEQUENCE: 10

| Met | Val | Ser | Trp | Gly | Arg | Phe | Ile | Cys | Leu | Val | Leu | Val | Thr | Met | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Leu | Ser | Leu | Ala | Arg | Pro | Ser | Phe | Ser | Leu | Val | Glu | Asp | Thr | Thr |
|     |     |     |     | 20  |     |     |     |     | 25  |     |     |     |     | 30  |     |

| Leu | Glu | Pro | Glu | Gly | Ala | Pro | Tyr | Trp | Thr | Asn | Thr | Glu | Lys | Met | Glu |
|     |     |     | 35  |     |     |     |     | 40  |     |     |     |     | 45  |     |     |

| Lys | Arg | Leu | His | Ala | Val | Pro | Ala | Ala | Asn | Thr | Val | Lys | Phe | Arg | Cys |
| 50  |     |     |     |     | 55  |     |     |     |     | 60  |     |     |     |     |     |

| Pro | Ala | Gly | Gly | Asn | Pro | Thr | Pro | Thr | Met | Arg | Trp | Leu | Lys | Asn | Gly |
| 65  |     |     |     |     | 70  |     |     |     |     | 75  |     |     |     |     | 80  |

| Lys | Glu | Phe | Lys | Gln | Glu | His | Arg | Ile | Gly | Gly | Tyr | Lys | Val | Arg | Asn |
|     |     |     |     | 85  |     |     |     |     | 90  |     |     |     |     | 95  |     |

| Gln | His | Trp | Ser | Leu | Ile | Met | Glu | Ser | Val | Val | Pro | Ser | Asp | Lys | Gly |
|     |     |     |     | 100 |     |     |     |     | 105 |     |     |     |     | 110 |     |

| Asn | Tyr | Thr | Cys | Leu | Val | Glu | Asn | Glu | Tyr | Gly | Ser | Ile | Asn | His | Thr |
|     |     |     |     | 115 |     |     |     |     | 120 |     |     |     |     | 125 |     |

| Tyr | His | Leu | Asp | Val | Val | Glu | Arg | Ser | Pro | His | Arg | Pro | Ile | Leu | Gln |
|     | 130 |     |     |     |     | 135 |     |     |     |     | 140 |     |     |     |     |

| Ala | Gly | Leu | Pro | Ala | Asn | Ala | Ser | Thr | Val | Val | Gly | Gly | Asp | Val | Glu |
| 145 |     |     |     |     | 150 |     |     |     |     | 155 |     |     |     |     | 160 |

| Phe | Val | Cys | Lys | Val | Tyr | Ser | Asp | Ala | Gln | Pro | His | Ile | Gln | Trp | Ile |
|     |     |     |     | 165 |     |     |     |     | 170 |     |     |     |     | 175 |     |

| Lys | His | Val | Glu | Lys | Asn | Gly | Ser | Lys | Tyr | Gly | Pro | Asp | Gly | Leu | Pro |
|     |     |     |     | 180 |     |     |     |     | 185 |     |     |     |     | 190 |     |

| Tyr | Leu | Lys | Val | Leu | Lys | His | Ser | Gly | Ile | Asn | Ser | Ser | Asn | Ala | Glu |
|     |     |     | 195 |     |     |     |     | 200 |     |     |     |     | 205 |     |     |

| Val | Leu | Ala | Leu | Phe | Asn | Val | Thr | Glu | Met | Asp | Ala | Gly | Glu | Tyr | Ile |
|     | 210 |     |     |     |     | 215 |     |     |     |     | 220 |     |     |     |     |

| Cys | Lys | Val | Ser | Asn | Tyr | Ile | Gly | Gln | Ala | Asn | Gln | Ser | Ala | Trp | Leu |
| 225 |     |     |     |     | 230 |     |     |     |     | 235 |     |     |     |     | 240 |

| Thr | Val | Leu | Pro | Lys | Gln | Gln | Ala | Pro | Val | Arg | Glu | Lys | Glu | Ile | Thr |
|     |     |     |     | 245 |     |     |     |     | 250 |     |     |     |     | 255 |     |

| Ala | Ser | Pro | Asp | Tyr | Leu | Glu | Ile | Ala | Ile | Tyr | Cys | Ile | Gly | Val | Phe |
|     |     |     | 260 |     |     |     |     | 265 |     |     |     |     | 270 |     |     |

| Leu | Ile | Ala | Cys | Met | Val | Val | Thr | Val | Ile | Phe | Cys | Arg | Met | Lys | Thr |
|     |     | 275 |     |     |     |     | 280 |     |     |     |     | 285 |     |     |     |

| Thr | Thr | Lys | Lys | Pro | Asp | Phe | Ser | Ser | Gln | Pro | Ala | Val | His | Lys | Leu |
|     |     | 290 |     |     |     |     | 295 |     |     |     |     | 300 |     |     |     |

| Thr | Lys | Arg | Ile | Pro | Leu | Arg | Arg | Gln | Val | Thr | Val | Ser | Ala | Glu | Ser |
| 305 |     |     |     |     | 310 |     |     |     |     | 315 |     |     |     |     | 320 |

| Ser | Ser | Ser | Met | Asn | Ser | Asn | Thr | Pro | Leu | Val | Arg | Ile | Thr | Thr | Arg |
|     |     |     |     | 325 |     |     |     |     | 330 |     |     |     |     | 335 |     |

| Leu | Ser | Ser | Thr | Ala | Asp | Thr | Pro | Met | Leu | Ala | Gly | Val | Ser | Glu | Tyr |
|     |     |     | 340 |     |     |     |     | 345 |     |     |     |     | 350 |     |     |

-continued

Glu Leu Pro Glu Asp Pro Lys Trp Glu Phe Pro Arg Asp Lys Leu Thr
355                 360                 365

Leu Gly Lys Pro Leu Gly Glu Gly Cys Phe Gly Gln Val Val Met Ala
370                 375                 380

Glu Ala Val Gly Ile Asp Lys Asp Lys Pro Lys Glu Ala Val Thr Val
385                 390                 395                 400

Ala Val Lys Met Leu Lys Asp Asp Ala Thr Glu Lys Asp Leu Ser Asp
            405                 410                 415

Leu Val Ser Glu Met Glu Met Met Lys Met Ile Gly Lys His Lys Asn
        420                 425                 430

Ile Ile Asn Leu Leu Gly Ala Cys Thr Gln Asp Gly Pro Leu Tyr Val
    435                 440                 445

Ile Val Glu Tyr Ala Ser Lys Gly Asn Leu Arg Glu Tyr Leu Arg Ala
450                 455                 460

Arg Arg Pro Pro Gly Met Glu Tyr Ser Tyr Asp Ile Asn Arg Val Pro
465                 470                 475                 480

Glu Glu Gln Met Thr Phe Lys Asp Leu Val Ser Cys Thr Tyr Gln Leu
            485                 490                 495

Ala Arg Gly Met Glu Tyr Leu Ala Ser Gln Lys Cys Ile His Arg Asp
        500                 505                 510

Leu Ala Ala Arg Asn Val Leu Val Thr Glu Asn Asn Val Met Lys Ile
    515                 520                 525

Ala Asp Phe Gly Leu Ala Arg Asp Ile Asn Asn Ile Asp Tyr Tyr Lys
530                 535                 540

Lys Thr Thr Asn Gly Arg Leu Pro Val Lys Trp Met Ala Pro Glu Ala
545                 550                 555                 560

Leu Phe Asp Arg Val Tyr Thr His Gln Ser Asp Val Trp Ser Phe Gly
            565                 570                 575

Val Leu Met Trp Glu Ile Phe Thr Leu Gly Gly Ser Pro Tyr Pro Gly
        580                 585                 590

Ile Pro Val Glu Glu Leu Phe Lys Leu Leu Lys Glu Gly His Arg Met
    595                 600                 605

Asp Lys Pro Thr Asn Cys Thr Asn Glu Leu Tyr Met Met Met Arg Asp
610                 615                 620

Cys Trp His Ala Val Pro Ser Gln Arg Pro Thr Phe Lys Gln Leu Val
625                 630                 635                 640

Glu Asp Leu Asp Arg Ile Leu Thr Leu Thr Thr Asn Glu Glu Tyr Leu
            645                 650                 655

Asp Leu Thr Gln Pro Leu Glu Gln Tyr Ser Pro Ser Tyr Pro Asp Thr
        660                 665                 670

Arg Ser Ser Cys Ser Ser Gly Asp Asp Ser Val Phe Ser Pro Asp Pro
    675                 680                 685

Met Pro Tyr Glu Pro Cys Leu Pro Gln Tyr Pro His Ile Asn Gly Ser
690                 695                 700

Val Lys Thr
705

<210> SEQ ID NO 11
<211> LENGTH: 3344
<212> TYPE: DNA
<213> ORGANISM: Xenopus tropicalis

<400> SEQUENCE: 11
agagcaggga agtacagcgc tgcgctacaa gaactgagca aacgagcaga aaagtacaca      60

```
ttcctgatcc ttcggtctttt ccaaaagtcc ccaatggggt cacacaggcc atggttactt      120
ggtgctgtgg tgctgctggc actccttcag gtacagggag gactggcaga atggacacag      180
tgtcaaatgg gattttccaa ggaaaggtac agcttttcgg tacctaagaa cttggagaca      240
gacaaagcac tgggtagagt gatctttaac agctgtgagg gaccagtgag aattcagttt      300
gcctctaaag atcctaattt tgaaattcac aaagatggca cagtttatgt taagaatcct      360
accaagatga aagacaacag aaaaacattc cgtgtcctgg cttgggagaa tcaaggtcat      420
gtatactcta ccagtgtaac cttgaaaggg gaagggcatc accataagca ggacatttct      480
tctgtgaaac attcccacca cccaaaatct gagactggtt taaaaagaca aaaaagagac      540
tgggtgattc caccaatcgt aacatctgag aatgaaaagg gcccatttcc caaacggctt      600
gtgcagatca agtccagtaa tgcaaaggaa atcaaggttt tttacagtat cacaggccag      660
ggtgccgata cccctccaga aggagtgttc actattggac gggaggatgg atggctaaat      720
gtgacacgac ctttggacag agaagccatt gatagttaca ctcttttttc tcatgctgtg      780
tcagtaaatg ggcaaaatgt ggaagatccc atggaaatcc aaattaaagt acaagatcag      840
aatgataatg acccagtttt cacacaggag gtctttgaag gctatgtgcc tgaagggtct      900
aagccaggta cgcccgtcat gactgtatct gcaacagatg ccgatgatgc tatagacatg      960
tacaatggtg tgattactta ctccattctc aaccaagacc ctaaagagcc caacaatcaa     1020
atgttcacta ttgattccca gtctgggttg atcagcgtag ttacaactgg attagacaga     1080
gagaaaatac cagtgtacac actgactatt caagctgcag atggagaatt tgggaaagat     1140
cgcacaacaa ctgcaaaagc tgtgatcatt gtgacagaca ccaatgataa ccctcctgtg     1200
tttaacccaa cgcaatacat tgcagaggtt cctgaaaatg aagttggata tgaggttgca     1260
cgtcttacgg taacagatgc agatattgaa gggtcagatg cctggaatgc tgtgtacaag     1320
atcattaaag gaaatgaggc tggcttttc agcatccaaa cagatattga caacattggg     1380
ctactgaaaa cagtgaaggg tctggactat gagctgaaga agcagtatat tctgtcagtc     1440
attgtgacaa acaaagctaa cttttctgtt ccactacaaa cttcaactgc aacggtcact     1500
gtaactgtca cagatgtgaa tgaggcccca gtatttgtac cagtgttgaa agacgtgtct     1560
gtgccagagg atctgcccag tggccaagtt gttgctacct ataccgcaca ggatccagac     1620
aaggaacaga accagaaaat aagttacttc attggaaatg acccagcagg gtgggtgtct     1680
gtgaacagag ataatgggat tgtcactgga aatggaaact tggatcggga atcaaagttt     1740
gtgctaaaca acacctacaa agtcataatc ttggccgctg acagtggcac tcctctgcc      1800 actgggactg gaacccttgt gcttaatctc attgatgtta atgataatgg cccattttttg     1860 gatccccaac aaaatagttt ctgccagaag gatccaggct ttcgtgtatt taatatcatt     1920
gacaaagatc tttaccctaa cacatacca tatacagtag acctgactgg tgaatccaat     1980
gaaaactgga ctgctacagt gacagaacag agtttacttg agctgagacc taaaaaggaa     2040
ctggatattg gacgatacga agtttttgatc tcattgagag acaatcaggg actgacagat     2100
gtgacaaagc tacagattac aatctgtcaa tgtaatggtg accaaatgca atgtgaggaa     2160
aaggctgctc aagcaggagg tttgggata tcagccatag ttggaatcct tggagggatc     2220
ctagcgcttc ttttattgtt gttgctgctc ttactgtttg tacgacgaaa gaaagtggta     2280 aaagaaacctt tattaccacc agaagatgag actcgggaca atgtattttt ctatgatgaa     2340
gaaggcggtg gtgaggaaga ccaggatttt gatctaagcc agcttcaccg tggtctagat     2400
gctcgtccag atataatccg taatgatgtc gttccagttt tagctgctcc ccagtatcga     2460
```

-continued

```
cccgtcctg ccaatccaga tgaaattgga aatttcattg atgagaactt gcatgcagct    2520
gacaatgacc ccactgctcc tccatacgac tcgctccttg tgttcgatta cgaaggcagt    2580
ggctctgagg ccgcatcact cagctctctt aactcttcca actctgattt agatcaggat    2640
tacagtgctt tgaataactg gggacctcgt ttcaccaaac tggcagaaat gtatggagga    2700
gatgaggatt agaatgtgca ctgcaatacc attttgattc taaacagtaa actaaaaacc    2760
ataattgtgt atgcagtctt tggaattcac tttgttttct cctgctctta aaacagagat    2820
aaggactgct caaaagttac tcctcctgct tttgtaaaat cgttcaaaaa tattttatgt    2880
atatgtatat atgaaaaaat cgtatttttt gtactatttg tgttcttata tccctgcaat    2940
ttgtaataca agaggatctt tatctgctta attataaata taaaatgccc gatatgattc    3000
actatgattt taatgtgttg agaaatcttt ttttaaaaag gtttccagac acctgacgct    3060
tggaagggaa ttccataaaa atataattga attgggggga gattgtgttt tgccatggtc    3120
tgatatacat tttcatatat atacatatga tcattcacag agtacagtca acatttggaa    3180
tttgatgagc ttgctggtcg aactgaaaaa aaaatgtatt atagctgggg taaaaattaa    3240
tgtatgagct aaatggggca caattttgat atctctgcat ttgtatttta cttggcatgt    3300 atactttgt aataaaataa agatatacat taatatacaa cata                     3344
```

<210> SEQ ID NO 12
<211> LENGTH: 872
<212> TYPE: PRT
<213> ORGANISM: Xenopus tropicalis

<400> SEQUENCE: 12

```
Met Gly Ser His Arg Pro Trp Leu Leu Gly Ala Val Val Leu Leu Ala
1               5                   10                  15

Leu Leu Gln Val Gln Gly Gly Leu Ala Glu Trp Thr Gln Cys Gln Met
            20                  25                  30

Gly Phe Ser Lys Glu Arg Tyr Ser Phe Ser Val Pro Lys Asn Leu Glu
        35                  40                  45

Thr Asp Lys Ala Leu Gly Arg Val Ile Phe Asn Ser Cys Glu Gly Pro
    50                  55                  60

Val Arg Ile Gln Phe Ala Ser Lys Asp Pro Asn Phe Glu Ile His Lys
65                  70                  75                  80

Asp Gly Thr Val Tyr Val Lys Asn Pro Thr Lys Met Lys Asp Asn Arg
                85                  90                  95

Lys Thr Phe Arg Val Leu Ala Trp Glu Asn Gln Gly His Val Tyr Ser
            100                 105                 110

Thr Ser Val Thr Leu Lys Gly Glu Gly His His Lys Gln Asp Ile
        115                 120                 125

Ser Ser Val Lys His Ser His His Pro Lys Ser Glu Thr Gly Leu Lys
    130                 135                 140

Arg Gln Lys Arg Asp Trp Val Ile Pro Pro Ile Val Thr Ser Glu Asn
145                 150                 155                 160

Glu Lys Gly Pro Phe Pro Lys Arg Leu Val Gln Ile Lys Ser Ser Asn
                165                 170                 175

Ala Lys Glu Ile Lys Val Phe Tyr Ser Ile Thr Gly Gln Gly Ala Asp
            180                 185                 190

Thr Pro Pro Glu Gly Val Phe Thr Ile Gly Arg Glu Asp Gly Trp Leu
        195                 200                 205

Asn Val Thr Arg Pro Leu Asp Arg Glu Ala Ile Asp Ser Tyr Thr Leu
```

-continued

```
              210                 215                 220
    Phe Ser His Ala Val Ser Val Asn Gly Gln Asn Val Glu Asp Pro Met
    225                 230                 235                 240

Glu Ile Gln Ile Lys Val Gln Asp Gln Asn Asp Asn Asp Pro Val Phe
                        245                 250                 255

Thr Gln Glu Val Phe Glu Gly Tyr Val Pro Glu Gly Ser Lys Pro Gly
                        260                 265                 270

Thr Pro Val Met Thr Val Ser Ala Thr Asp Ala Asp Asp Ala Ile Asp
                    275                 280                 285

Met Tyr Asn Gly Val Ile Thr Tyr Ser Ile Leu Asn Gln Asp Pro Lys
                290                 295                 300

Glu Pro Asn Asn Gln Met Phe Thr Ile Asp Ser Gln Ser Gly Leu Ile
    305                 310                 315                 320

Ser Val Val Thr Thr Gly Leu Asp Arg Glu Lys Ile Pro Val Tyr Thr
                        325                 330                 335

Leu Thr Ile Gln Ala Ala Asp Gly Glu Phe Gly Lys Asp Arg Thr Thr
                        340                 345                 350

Thr Ala Lys Ala Val Ile Ile Val Thr Asp Thr Asn Asp Asn Pro Pro
                    355                 360                 365

Val Phe Asn Pro Thr Gln Tyr Ile Ala Glu Val Pro Glu Asn Glu Val
                370                 375                 380

Gly Tyr Glu Val Ala Arg Leu Thr Val Thr Asp Ala Asp Ile Glu Gly
    385                 390                 395                 400

Ser Asp Ala Trp Asn Ala Val Tyr Lys Ile Ile Lys Gly Asn Glu Ala
                        405                 410                 415

Gly Phe Phe Ser Ile Gln Thr Asp Ile Asp Asn Ile Gly Leu Leu Lys
                        420                 425                 430

Thr Val Lys Gly Leu Asp Tyr Glu Leu Lys Lys Gln Tyr Ile Leu Ser
                    435                 440                 445

Val Ile Val Thr Asn Lys Ala Asn Phe Ser Val Pro Leu Gln Thr Ser
                450                 455                 460

Thr Ala Thr Val Thr Val Thr Val Thr Asp Val Asn Glu Ala Pro Val
    465                 470                 475                 480

Phe Val Pro Val Leu Lys Asp Val Ser Val Pro Glu Asp Leu Pro Ser
                        485                 490                 495

Gly Gln Val Val Ala Thr Tyr Thr Ala Gln Asp Pro Asp Lys Glu Gln
                        500                 505                 510

Asn Gln Lys Ile Ser Tyr Phe Ile Gly Asn Asp Pro Ala Gly Trp Val
                    515                 520                 525

Ser Val Asn Arg Asp Asn Gly Ile Val Thr Gly Asn Gly Asn Leu Asp
                530                 535                 540

Arg Glu Ser Lys Phe Val Leu Asn Asn Thr Tyr Lys Val Ile Ile Leu
    545                 550                 555                 560

Ala Ala Asp Ser Gly Thr Pro Ser Ala Thr Gly Thr Gly Thr Leu Val
                        565                 570                 575

Leu Asn Leu Ile Asp Val Asn Asp Asn Gly Pro Phe Leu Asp Pro Gln
                        580                 585                 590

Gln Asn Ser Phe Cys Gln Lys Asp Pro Gly Phe Arg Val Phe Asn Ile
                    595                 600                 605

Ile Asp Lys Asp Leu Tyr Pro Asn Thr Tyr Pro Tyr Thr Val Asp Leu
                610                 615                 620

Thr Gly Glu Ser Asn Glu Asn Trp Thr Ala Thr Val Thr Glu Gln Ser
    625                 630                 635                 640
```

Leu Leu Glu Leu Arg Pro Lys Lys Glu Leu Asp Ile Gly Arg Tyr Glu
                645                 650                 655

Val Leu Ile Ser Leu Arg Asp Asn Gln Gly Leu Thr Asp Val Thr Lys
            660                 665                 670

Leu Gln Ile Thr Ile Cys Gln Cys Asn Gly Asp Gln Met Gln Cys Glu
        675                 680                 685

Glu Lys Ala Ala Gln Ala Gly Gly Leu Gly Ile Ser Ala Ile Val Gly
    690                 695                 700

Ile Leu Gly Gly Ile Leu Ala Leu Leu Leu Leu Leu Leu Leu Leu Leu
705                 710                 715                 720

Leu Phe Val Arg Arg Lys Lys Val Val Lys Glu Pro Leu Leu Pro Pro
                725                 730                 735

Glu Asp Glu Thr Arg Asp Asn Val Phe Phe Tyr Asp Glu Gly Gly Gly
            740                 745                 750

Gly Glu Glu Asp Gln Asp Phe Asp Leu Ser Gln Leu His Arg Gly Leu
        755                 760                 765

Asp Ala Arg Pro Asp Ile Ile Arg Asn Asp Val Val Pro Val Leu Ala
    770                 775                 780

Ala Pro Gln Tyr Arg Pro Arg Pro Ala Asn Pro Asp Glu Ile Gly Asn
785                 790                 795                 800

Phe Ile Asp Glu Asn Leu His Ala Ala Asp Asn Asp Pro Thr Ala Pro
                805                 810                 815

Pro Tyr Asp Ser Leu Leu Val Phe Asp Tyr Glu Gly Ser Gly Ser Glu
            820                 825                 830

Ala Ala Ser Leu Ser Ser Leu Asn Ser Ser Asn Ser Asp Leu Asp Gln
        835                 840                 845

Asp Tyr Ser Ala Leu Asn Asn Trp Gly Pro Arg Phe Thr Lys Leu Ala
    850                 855                 860

Glu Met Tyr Gly Gly Asp Glu Asp
865                 870

<210> SEQ ID NO 13
<211> LENGTH: 1862
<212> TYPE: DNA
<213> ORGANISM: Homo sapiens

<400> SEQUENCE: 13
gtccccgcgc cagagacgca gccgcgctcc caccacccac acccaccgcg ccctcgttcg    60
cctcttctcc gggagccagt ccgcgccacc gccgccgccc aggccatcgc caccctccgc   120
agccatgtcc accaggtccg tgtcctcgtc ctcctaccgc aggatgttcg gcggcccggg   180
caccgcgagc cggccgagct ccagccggag ctacgtgact acgtccaccc gcacctacag   240
cctgggcagc gcgctgcgcc ccagcaccag ccgcagcctc tacgcctcgt ccccgggcgg   300
cgtgtatgcc acgcgctcct ctgccgtgcg cctgcggagc agcgtgcccg gggtgcggct   360
cctgcaggac tcggtggact ctcgctggc cgacgccatc aacaccgagt tcaagaacac   420
ccgcaccaac gagaaggtgg agctgcagga gctgaatgac cgcttcgcca actacatcga   480
caaggtgcgc ttcctggagc agcagaataa gatcctgctg gccgagctcg agcagctcaa   540
gggccaaggc aagtcgcgcc tggggggacct ctacgaggag gagatgcggg agctgcgccg   600
gcaggtggac cagctaacca acgacaaagc ccgcgtcgag gtggagcgcg acaacctggc   660
cgaggacatc atgcgcctcc gggagaaatt gcaggaggag atgcttcaga gagaggaagc   720
cgaaaacacc ctgcaatctt tcagacagga tgttgacaat gcgtctctgg cacgtcttga   780

```
ccttgaacgc aaagtggaat cttttgcaaga agagattgcc ttttttgaaga aactccacga    840 agaggaaatc caggagctgc aggctcagat tcaggaacag catgtccaaa tcgatgtgga    900
tgtttccaag cctgacctca cggctgccct gcgtgacgta cgtcagcaat atgaaagtgt    960
ggctgccaag aacctgcagg aggcagaaga atggtacaaa tccaagtttg ctgacctctc   1020
tgaggctgcc aaccggaaca atgacgccct gcgccaggca aagcaggagt ccactgagta   1080
ccggagacag gtgcagtccc tcacctgtga agtggatgcc cttaaaggaa ccaatgagtc   1140
cctggaacgc cagatgcgtg aaatggaaga gaactttgcc gttgaagctg ctaactacca   1200
agacactatt ggccgcctgc aggatgagat tcagaatatg aaggaggaaa tggctcgtca   1260
ccttcgtgaa taccaagacc tgctcaatgt taagatggcc cttgacattg agattgccac   1320
ctacaggaag ctgctggaag gcgaggagag caggatttct ctgcctcttc caaacttttc   1380
ctccctgaac ctgagggaaa ctaatctgga ttcactccct ctggttgata cccactcaaa   1440
aaggacactt ctgattaaga cggttgaaac tagagatgga caggttatca acgaaacttc   1500
tcagcatcac gatgaccttg aataaaaatt gcacacactc agtgcagcaa tatattacca   1560
gcaagaataa aaaagaaatc catatcttaa agaaacagct ttcaagtgcc tttctgcagt   1620
ttttcaggag cgcaagatag atttggaata ggaataagct ctagttctta acaaccgaca   1680
ctcctacaag atttagaaaa aagtttacaa cataatctag tttacagaaa atcttgtgc   1740 tagaatactt tttaaaaggt attttgaata ccattaaaac tgctttttt tttccagcaa   1800 gtatccaacc aacttggttc tgcttcaata atctttgga aaaactcaaa aaaaaaaaa   1860 aa                                                                 1862
```

<210> SEQ ID NO 14
<211> LENGTH: 466
<212> TYPE: PRT
<213> ORGANISM: Homo sapiens

<400> SEQUENCE: 14

```
Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
        50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175
```

```
Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
        260                 265                 270

Arg Gln Gln Tyr Glu Ser Val Ala Ala Lys Asn Leu Gln Glu Ala Glu
    275                 280                 285

Glu Trp Tyr Lys Ser Lys Phe Ala Asp Leu Ser Glu Ala Ala Asn Arg
290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
450                 455                 460

Leu Glu
465

<210> SEQ ID NO 15
<211> LENGTH: 2721
<212> TYPE: DNA
<213> ORGANISM: Homo sapiens

<400> SEQUENCE: 15
atgtgccgga tagcgggagc gctgcggacc ctgctgccgc tgctggcggc cctgcttcag     60
gcgtctgtag aggcttctgg tgaaatcgca ttatgcaaga ctggatttcc tgaagatgtt    120
tacagtgcag tcttatcgaa ggatgtgcat gaaggacagc tcttctcaa tgtgaagttt     180 agcaactgca atggaaaaag aaaagtacaa tatgagagca gtgagcctgc agattttaag    240
gtggatgaag atggcatggt gtatgccgtg agaagctttc cactctcttc tgagcatgcc    300
aagttcctga tatatgccca agacaaagag acccaggaaa gtggcaagt ggcagtaaaa     360 ttgagcctga agccaacctt aactgaggag tcagtgaagg agtcagcaga agttgaagaa    420
```

```
atagtgttcc caagacaatt cagtaagcac agtggccacc tacaaaggca gaagagagac    480
tgggtcatcc ctccaatcaa cttgccagaa aactccaggg gaccttttcc tcaagagctt    540
gtcaggatca ggtctgatag agataaaaac ctttcactgc ggtacagtgt aactgggcca    600
ggagctgacc agcctccaac tggtatcttc attatcaacc ccatctcggg tcagctgtcg    660
gtgacaaagc ccctggatcg cgagcagata gcccggtttc atttgagggc acatgcagta    720
gatattaatg gaaatcaagt ggagaacccc attgacattg tcatcaatgt tattgacatg    780
aatgacaaca gacctgagtt cttacaccag gtttggaatg ggacagttcc tgagggatca    840
aagcctggaa catatgtgat gaccgtaaca gcaattgatg ctgacgatcc caatgccctc    900
aatgggatgt tgaggtacag aatcgtgtct caggctccaa gcaccccttc acccaacatg    960
tttacaatca acaatgagac tggtgacatc atcacagtgg cagctggact tgatcgagaa   1020
aaagtgcaac agtatacgtt aataattcaa gctacagaca tggaaggcaa tcccacatat   1080
ggcctttcaa acacagccac ggccgtcatc acagtgacag atgtcaatga caatcctcca   1140
gagtttactg ccatgacgtt ttatggtgaa gttcctgaga cagggtaga catcatagta    1200
gctaatctaa ctgtgaccga taaggatcaa ccccatacac cagcctggaa cgcagtgtac   1260
agaatcagtg gcggagatcc tactggacgg ttcgccatcc agaccgaccc aaacagcaac   1320
gacgggttag tcaccgtggt caaaccaatc gactttgaaa caaataggat gtttgtcctt   1380
actgttgctg cagaaaatca gtgccatta gccaagggaa ttcagcaccc ccctcagtca   1440
actgcaaccg tgtctgttac agttattgac gtaaatgaaa acccttattt tgcccccaat   1500
cctaagatca ttcgccaaga agaagggctt catgccggta ccatgttgac aacattcact   1560
gctcaggacc cagatcgata tatgcagcaa aatattagat acactaaatt atctgatcct   1620
gccaattggc taaaaataga tcctgtgaat ggacaaataa ctacaattgc tgttttggac   1680
cgagaatcac caaatgtgaa aaacaatata tataatgcta cttccttgc ttctgacaat   1740
ggaattcctc ctatgagtgg aacaggaacg ctgcagatct atttacttga tattaatgac   1800
aatgccctc aagtgttacc tcaagaggca gagacttgcg aaactccaga ccccaattca   1860
attaatatta cagcacttga ttatgacatt gatccaaatg ctggaccatt tgcttttgat   1920
cttcctttat ctccagtgac tattaagaga aattggacca tcactcggct taatggtgat   1980
tttgctcagc ttaattaaaa gataaaattt cttgaagctg gtatctatga agttcccatc   2040
ataatcacag attcgggtaa tcctcccaaa tcaaatattt ccatcctgcg tgtgaaggtt   2100
tgccagtgtg actccaacgg ggactgcaca gatgtggaca ggattgtggg tgcgggcctt   2160
ggcaccggtg ccatcattgc catcctgctc tgcatcatca tcctgcttat ccttgtgctg   2220
atgtttgtgg tatggatgaa acgccggat aaagaacgcc aggccaaaca acttttaatt   2280
gatccagaag atgatgtaag agataatatt ttaaaatatg atgaagaagg tggaggagaa   2340
gaagaccagg actatgactt gagccagctg cagcagcctg cactgtggga gcctgatgcc   2400
atcaagcctg tgggaatccg acgaatggat gaaagaccca tccacgccga gccccagtat   2460
ccggtccgat ctgcagcccc acaccctgga gacattgggg acttcattaa tgagggcctt   2520
aaagcggctg acaatgaccc cacagctcca ccatatgact ccctgttagt gtttgactat   2580
gaaggcagtg gctccactgc tgggtccttg agctccctta attcctcaag tagtggtggt   2640
gagcaggact atgattacct gaacgactgg gggccacggt tcaagaaact tgctgacatg   2700
tatggtggag gtgatgactg a                                             2721
```

```
<210> SEQ ID NO 16
<211> LENGTH: 906
<212> TYPE: PRT
<213> ORGANISM: Homo sapiens

<400> SEQUENCE: 16

Met Cys Arg Ile Ala Gly Ala Leu Arg Thr Leu Leu Pro Leu Leu Ala
1               5                   10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
        35                  40                  45

Val His Glu Gly Gln Pro Leu Leu Asn Val Lys Phe Ser Asn Cys Asn
    50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser
                85                  90                  95

Ser Glu His Ala Lys Phe Leu Ile Tyr Ala Gln Asp Lys Glu Thr Gln
            100                 105                 110

Glu Lys Trp Gln Val Ala Val Lys Leu Ser Leu Lys Pro Thr Leu Thr
        115                 120                 125

Glu Glu Ser Val Lys Glu Ser Ala Glu Val Glu Ile Val Phe Pro
130                 135                 140

Arg Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
            180                 185                 190

Leu Arg Tyr Ser Val Thr Gly Pro Gly Ala Asp Gln Pro Pro Thr Gly
        195                 200                 205

Ile Phe Ile Ile Asn Pro Ile Ser Gly Gln Leu Ser Val Thr Lys Pro
210                 215                 220

Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
            260                 265                 270

Asn Gly Thr Val Pro Glu Gly Ser Lys Pro Gly Thr Tyr Val Met Thr
        275                 280                 285

Val Thr Ala Ile Asp Ala Asp Pro Asn Ala Leu Asn Gly Met Leu
290                 295                 300

Arg Tyr Arg Ile Val Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                325                 330                 335

Leu Asp Arg Glu Lys Val Gln Gln Tyr Thr Leu Ile Ile Gln Ala Thr
            340                 345                 350

Asp Met Glu Gly Asn Pro Thr Tyr Gly Leu Ser Asn Thr Ala Thr Ala
        355                 360                 365

Val Ile Thr Val Thr Asp Val Asn Asp Asn Pro Pro Glu Phe Thr Ala
370                 375                 380
```

```
Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
                405                 410                 415

Asn Ala Val Tyr Arg Ile Ser Gly Gly Asp Pro Thr Gly Arg Phe Ala
            420                 425                 430

Ile Gln Thr Asp Pro Asn Ser Asn Asp Gly Leu Val Thr Val Val Lys
        435                 440                 445

Pro Ile Asp Phe Glu Thr Asn Arg Met Phe Val Leu Thr Val Ala Ala
    450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                485                 490                 495

Phe Ala Pro Asn Pro Lys Ile Ile Arg Gln Glu Glu Gly Leu His Ala
            500                 505                 510

Gly Thr Met Leu Thr Thr Phe Thr Ala Gln Asp Pro Asp Arg Tyr Met
        515                 520                 525

Gln Gln Asn Ile Arg Tyr Thr Lys Leu Ser Asp Pro Ala Asn Trp Leu
530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
                565                 570                 575

Ala Ser Asp Asn Gly Ile Pro Pro Met Ser Gly Thr Gly Thr Leu Gln
            580                 585                 590

Ile Tyr Leu Leu Asp Ile Asn Asp Asn Ala Pro Gln Val Leu Pro Gln
        595                 600                 605

Glu Ala Glu Thr Cys Glu Thr Pro Asp Pro Asn Ser Ile Asn Ile Thr
    610                 615                 620

Ala Leu Asp Tyr Asp Ile Asp Pro Asn Ala Gly Pro Phe Ala Phe Asp
625                 630                 635                 640

Leu Pro Leu Ser Pro Val Thr Ile Lys Arg Asn Trp Thr Ile Thr Arg
                645                 650                 655

Leu Asn Gly Asp Phe Ala Gln Leu Asn Leu Lys Ile Lys Phe Leu Glu
            660                 665                 670

Ala Gly Ile Tyr Glu Val Pro Ile Ile Thr Asp Ser Gly Asn Pro
        675                 680                 685

Pro Lys Ser Asn Ile Ser Ile Leu Arg Val Lys Val Cys Gln Cys Asp
    690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Leu Cys Ile Ile Ile Leu Leu
                725                 730                 735

Ile Leu Val Leu Met Phe Val Val Trp Met Lys Arg Arg Asp Lys Glu
            740                 745                 750

Arg Gln Ala Lys Gln Leu Leu Ile Asp Pro Glu Asp Asp Val Arg Asp
        755                 760                 765

Asn Ile Leu Lys Tyr Asp Glu Glu Gly Gly Gly Glu Glu Asp Gln Asp
    770                 775                 780

Tyr Asp Leu Ser Gln Leu Gln Gln Pro Asp Thr Val Glu Pro Asp Ala
785                 790                 795                 800
```

```
Ile Lys Pro Val Gly Ile Arg Arg Met Asp Glu Arg Pro Ile His Ala
            805                 810                 815

Glu Pro Gln Tyr Pro Val Arg Ser Ala Ala Pro His Pro Gly Asp Ile
        820                 825                 830

Gly Asp Phe Ile Asn Glu Gly Leu Lys Ala Ala Asp Asn Asp Pro Thr
    835                 840                 845

Ala Pro Pro Tyr Asp Ser Leu Leu Val Phe Asp Tyr Glu Gly Ser Gly
850                 855                 860

Ser Thr Ala Gly Ser Leu Ser Ser Leu Asn Ser Ser Ser Gly Gly
865                 870                 875                 880

Glu Gln Asp Tyr Asp Tyr Leu Asn Asp Trp Gly Pro Arg Phe Lys Lys
                885                 890                 895

Leu Ala Asp Met Tyr Gly Gly Gly Asp Asp
                900                 905

<210> SEQ ID NO 17
<211> LENGTH: 2391
<212> TYPE: DNA
<213> ORGANISM: Homo sapiens

<400> SEQUENCE: 17
```

| | | | | | |
|---|---|---|---|---|---|
| atgaaggaga | actactgttt | acaagccgcc | ctggtgtgcc | tgggcatgct | gtgccacagc    60 |
| catgccttg | ccccagagcg | gcgggggcac | ctgcggccct | ccttccatgg | caccatgag    120 |
| aagggcaagg | agggggcaggt | gctacagcgc | tccaagcgtg | gctgggtctg | gaaccagttc    180 |
| ttcgtgatag | aggagtacac | cgggcctgac | cccgtgcttg | tgggcaggct | tcattcagat    240 |
| attgactctg | gtgatgggaa | cattaaatac | attctctcag | gggaaggagc | tggaaccatt    300 |
| tttgtgattg | atgacaaatc | aggaacatt | catgccacca | agacgttgga | tcgagaagag    360 |
| agagcccagt | acacgttgat | ggctcaggcg | gtggacaggg | acaccaatcg | ccactggag    420 |
| ccaccgtcgg | aattcattgt | caaggtccag | gacattaatg | caaccctcc | ggagttcctg    480 |
| cacgagacct | atcatgccaa | cgtgcctgag | aggtccaatg | tgggaacgtc | agtaatccag    540 |
| gtgacagctt | cagatgcaga | tgaccccact | tatggaaata | cgccaagtt | agtgtacagt    600 |
| atcctcgaag | acaacccta | ttttcggtg | aagcacaga | caggtatcat | cagaacagcc    660 |
| ctacccaaca | tggacaggga | ggccaaggag | gagtaccacg | tggtgatcca | ggccaaggac    720 |
| atgggtggac | atatgggcgg | actctcaggg | acaaccaaag | tgacgatcac | actgaccgat    780 |
| gtcaatgaca | acccaccaaa | gtttccgcag | agcgtatacc | agatgtctgt | gtcagaagca    840 |
| gccgtccctg | ggaggaagt | aggaagagtg | aaagctaaag | atccagacat | tggagaaaat    900 |
| ggcttagtca | catacaatat | tgttgatgga | gatggtatgg | aatcgtttga | aatcacaacg    960 |
| gactatgaaa | cacaggaggg | ggtgataaag | ctgaaaaagc | ctgtagattt | tgaaaccaaa   1020 |
| agagcctata | gcttgaaggt | agaggcagcc | aacgtgcaca | tcgacccgaa | gtttatcagc   1080 |
| aatggcccctt | tcaaggacac | tgtgaccgtc | aagatctcag | tagaagatgc | tgatgagccc   1140 |
| cctatgttct | tggccccaag | ttacatccac | gaagtccaag | aaaatgcagc | tgctggcacc   1200 |
| gtggttggga | gagtgcatgc | caaagaccct | gatgctgcca | acagcccgat | aaggtattcc   1260 |
| atcgatcgtc | acactgacct | cgacagattt | ttcactatta | tcccagagga | tggtttat   1320 |
| aaaactacaa | aacctctgga | tagagaggaa | acagcctggc | tcaacatcac | tgtctttgca   1380 |
| gcagaaatcc | acaatcggca | tcaggaagcc | aaagtcccag | tggccattag | ggtccttgat   1440 |
| gtcaacgata | atgctcccaa | gtttgctgcc | ccttatgaag | gtttcatctg | tgagagtgat   1500 |

```
cagaccaagc cactttccaa ccagccaatt gttacaatta gtgcagatga caaggatgac    1560
acggccaatg gaccaagatt tatcttcagc ctacccctg aaatcattca caatccaaat     1620
ttcacagtca gagacaaccg agataacaca gcaggcgtgt acgcccggcg tggagggttc    1680
agtcggcaga agcaggactt gtaccttctg cccatagtga tcagcgatgg cggcatcccg    1740
cccatgagta gcaccaacac cctcaccatc aaagtctgcg ggtgcgacgt gaacggggca    1800
ctgctctcct gcaacgcaga ggcctacatt ctgaacgccg gcctgagcac aggcgccctg    1860
atcgccatcc tcgcctgcat cgtcattctc ctggtcattg tagtattgtt tgtgaccctg    1920
agaaggcaaa agaaagaacc actcattgtc tttgaggaag aagatgtccg tgagaacatc    1980
attacttatg atgatgaagg gggtggggaa gaagacacag aagcctttga tattgccacc    2040
ctccagaatc ctgatggtat caatggattt atccccgca aagacatcaa acctgagtat      2100
cagtacatgc ctagacctgg gctccggcca gcgcccaaca gcgtggatgt cgatgacttc    2160
atcaacacga gaatacagga ggcagacaat gaccccacgg ctcctcctta tgactccatt    2220
caaatctacg gttatgaagg caggggctca gtggccgggt ccctgagctc cctagagtcg    2280
gccaccacag attcagactt ggactatgat tatctacaga actggggacc tcgttttaag    2340
aaactagcag atttgtatgg ttccaaagac acttttgatg acgattctta a             2391
```

<210> SEQ ID NO 18
<211> LENGTH: 796
<212> TYPE: PRT
<213> ORGANISM: Homo sapiens

<400> SEQUENCE: 18

```
Met Lys Glu Asn Tyr Cys Leu Gln Ala Ala Leu Val Cys Leu Gly Met
1               5                   10                  15

Leu Cys His Ser His Ala Phe Ala Pro Glu Arg Arg Gly His Leu Arg
            20                  25                  30

Pro Ser Phe His Gly His His Glu Lys Gly Lys Glu Gly Gln Val Leu
        35                  40                  45

Gln Arg Ser Lys Arg Gly Trp Val Trp Asn Gln Phe Phe Val Ile Glu
    50                  55                  60

Glu Tyr Thr Gly Pro Asp Pro Val Leu Val Gly Arg Leu His Ser Asp
65                  70                  75                  80

Ile Asp Ser Gly Asp Gly Asn Ile Lys Tyr Ile Leu Ser Gly Glu Gly
                85                  90                  95

Ala Gly Thr Ile Phe Val Ile Asp Asp Lys Ser Gly Asn Ile His Ala
            100                 105                 110

Thr Lys Thr Leu Asp Arg Glu Glu Arg Ala Gln Tyr Thr Leu Met Ala
        115                 120                 125

Gln Ala Val Asp Arg Asp Thr Asn Arg Pro Leu Glu Pro Pro Ser Glu
    130                 135                 140

Phe Ile Val Lys Val Gln Asp Ile Asn Asp Asn Pro Pro Glu Phe Leu
145                 150                 155                 160

His Glu Thr Tyr His Ala Asn Val Pro Glu Arg Ser Asn Val Gly Thr
                165                 170                 175

Ser Val Ile Gln Val Thr Ala Ser Asp Ala Asp Asp Pro Thr Tyr Gly
            180                 185                 190

Asn Ser Ala Lys Leu Val Tyr Ser Ile Leu Glu Gly Gln Pro Tyr Phe
        195                 200                 205

Ser Val Glu Ala Gln Thr Gly Ile Ile Arg Thr Ala Leu Pro Asn Met
    210                 215                 220
```

-continued

```
Asp Arg Glu Ala Lys Glu Tyr His Val Val Ile Gln Ala Lys Asp
225                 230                 235                 240

Met Gly Gly His Met Gly Gly Leu Ser Gly Thr Thr Lys Val Thr Ile
                    245                 250                 255

Thr Leu Thr Asp Val Asn Asp Asn Pro Pro Lys Phe Pro Gln Ser Val
            260                 265                 270

Tyr Gln Met Ser Val Ser Glu Ala Val Pro Gly Glu Glu Val Gly
        275                 280                 285

Arg Val Lys Ala Lys Asp Pro Asp Ile Gly Glu Asn Gly Leu Val Thr
    290                 295                 300

Tyr Asn Ile Val Asp Gly Asp Gly Met Glu Ser Phe Glu Ile Thr Thr
305                 310                 315                 320

Asp Tyr Glu Thr Gln Glu Gly Val Ile Lys Leu Lys Pro Val Asp
            325                 330                 335

Phe Glu Thr Lys Arg Ala Tyr Ser Leu Lys Val Glu Ala Ala Asn Val
            340                 345                 350

His Ile Asp Pro Lys Phe Ile Ser Asn Gly Pro Phe Lys Asp Thr Val
        355                 360                 365

Thr Val Lys Ile Ser Val Glu Asp Ala Asp Glu Pro Pro Met Phe Leu
370                 375                 380

Ala Pro Ser Tyr Ile His Glu Val Gln Glu Asn Ala Ala Ala Gly Thr
385                 390                 395                 400

Val Val Gly Arg Val His Ala Lys Asp Pro Asp Ala Ala Asn Ser Pro
            405                 410                 415

Ile Arg Tyr Ser Ile Asp Arg His Thr Asp Leu Asp Arg Phe Phe Thr
        420                 425                 430

Ile Asn Pro Glu Asp Gly Phe Ile Lys Thr Thr Lys Pro Leu Asp Arg
        435                 440                 445

Glu Glu Thr Ala Trp Leu Asn Ile Thr Val Phe Ala Ala Glu Ile His
450                 455                 460

Asn Arg His Gln Glu Ala Lys Val Pro Val Ala Ile Arg Val Leu Asp
465                 470                 475                 480

Val Asn Asp Asn Ala Pro Lys Phe Ala Ala Pro Tyr Glu Gly Phe Ile
            485                 490                 495

Cys Glu Ser Asp Gln Thr Lys Pro Leu Ser Asn Gln Pro Ile Val Thr
            500                 505                 510

Ile Ser Ala Asp Asp Lys Asp Asp Thr Ala Asn Gly Pro Arg Phe Ile
        515                 520                 525

Phe Ser Leu Pro Pro Glu Ile Ile His Asn Pro Asn Phe Thr Val Arg
        530                 535                 540

Asp Asn Arg Asp Asn Thr Ala Gly Val Tyr Ala Arg Arg Gly Gly Phe
545                 550                 555                 560

Ser Arg Gln Lys Gln Asp Leu Tyr Leu Leu Pro Ile Val Ile Ser Asp
            565                 570                 575

Gly Gly Ile Pro Pro Met Ser Ser Thr Asn Thr Leu Thr Ile Lys Val
            580                 585                 590

Cys Gly Cys Asp Val Asn Gly Ala Leu Leu Ser Cys Asn Ala Glu Ala
            595                 600                 605

Tyr Ile Leu Asn Ala Gly Leu Ser Thr Gly Ala Leu Ile Ala Ile Leu
        610                 615                 620

Ala Cys Ile Val Ile Leu Leu Val Ile Val Val Leu Phe Val Thr Leu
625                 630                 635                 640
```

```
Arg Arg Gln Lys Lys Glu Pro Leu Ile Val Phe Glu Glu Glu Asp Val
            645                 650                 655

Arg Glu Asn Ile Ile Thr Tyr Asp Asp Glu Gly Gly Gly Glu Glu Asp
            660                 665                 670

Thr Glu Ala Phe Asp Ile Ala Thr Leu Gln Asn Pro Asp Gly Ile Asn
            675                 680                 685

Gly Phe Ile Pro Arg Lys Asp Ile Lys Pro Glu Tyr Gln Tyr Met Pro
        690                 695                 700

Arg Pro Gly Leu Arg Pro Ala Pro Asn Ser Val Asp Val Asp Asp Phe
705                 710                 715                 720

Ile Asn Thr Arg Ile Gln Glu Ala Asp Asn Asp Pro Thr Ala Pro Pro
                725                 730                 735

Tyr Asp Ser Ile Gln Ile Tyr Gly Tyr Glu Gly Arg Gly Ser Val Ala
            740                 745                 750

Gly Ser Leu Ser Ser Leu Glu Ser Ala Thr Thr Asp Ser Asp Leu Asp
            755                 760                 765

Tyr Asp Tyr Leu Gln Asn Trp Gly Pro Arg Phe Lys Lys Leu Ala Asp
        770                 775                 780

Leu Tyr Gly Ser Lys Asp Thr Phe Asp Asp Ser
785                 790                 795

<210> SEQ ID NO 19
<211> LENGTH: 2598
<212> TYPE: DNA
<213> ORGANISM: Homo sapiens

<400> SEQUENCE: 19
atggccctcg tactcggctc cctgttgctg ctggggctgt gcgggaactc cttttcagga      60
gggcagcctt catccacaga tgctcctaag gcttggaatt atgaattgcc tgcaacaaat     120
tatgagaccc aagactccca taaagctgga cccattggca ttctctttga actagtgcat     180
atctttctct atgtggtaca gccgcgtgat ttcccagaag atactttgag aaaattctta     240
cagaaggcat atgaatccaa aattgattat gacaagccag aaactgtaat cttaggtcta     300
aagattgtct actatgaagc agggattatt ctatgctgtg tcctggggct gctgtttatt     360
attctgatgc ctctggtggg gtatttcttt tgtatgtgtc gttgctgtaa caatgtggt      420 ggagaaatgc accagcgaca gaaggaaaat gggccttcc tgaggaaatg cttgcaatc      480 tccctgttgg tgatttgtat aataataagc attggcatct tctatggttt tgtggcaaat    540
caccaggtaa gaacccggat caaaggagt cggaaactgg cagatagcaa tttcaaggac    600
ttgcgaactc tcttgaatga aactccagag caaatcaaat atatattggc ccagtacaac     660
actaccaagg acaaggcgtt cacagatctg aacagtatca attcagtgct aggaggcgga    720
attcttgacc gactgagacc caacatcatc cctgttcttg atgagattaa gtccatggca    780
acagcgatca ggagaccaa agaggcgttg gagaacatga cagcaccttt gaagagcttg    840
caccaacaaa gtacacagct tagcagcagt ctgaccagcg tgaaaactag cctgcggtca    900
tctctcaatg accctctgtg cttggtgcat ccatcaagtg aaacctgcaa cagcatcaga    960
ttgtctctaa gccagctgaa tagcaaccct gaactgaggc agcttccacc cgtggatgca   1020
gaacttgaca acgttaataa cgttcttagg acagatttgg atggcctggt ccaacagggc   1080
tatcaatccc ttaatgatat acctgacaga gtacaacgcc aaaccacgac tgtcgtagca   1140
ggtatcaaaa gggtcttgaa ttccattggt tcagatatcg acaatgtaac tcagcgtctt   1200
cctattcagg atatactctc agcattctct gtttatgtta ataacactga agttacatc    1260
```

-continued

```
cacagaaatt tacctacatt ggaagagtat gattcatact ggtggctggg tggcctggtc   1320
atctgctctc tgctgaccct catcgtgatt ttttactacc tgggcttact gtgtggcgtg   1380
tgcggctatg acaggcatgc cacccccgacc acccgaggct gtgtctccaa caccggaggc   1440
gtcttcctca tggttggagt tggattaagt ttcctctttt gctggatatt gatgatcatt   1500
gtggttctta cctttgtctt tggtgcaaat gtggaaaaac tgatctgtga accttacacg   1560
agcaaggaat tattccgggt tttggataca ccctacttac taaatgaaga ctgggaatac   1620
tatctctctg ggaagctatt taataaatca aaaatgaagc tcacttttga caagtttac    1680
agtgactgca aaaaaaatag aggcacttac ggcactcttc acctgcagaa cagcttcaat   1740
atcagtgaac atctcaacat taatgagcat actggaagca taagcagtga attggaaagt   1800
ctgaaggtaa atcttaatat ctttctgttg ggtgcagcag aagaaaaaaa ccttcaggat   1860
tttgctgctt gtggaataga cagaatgaat tatgacagct acttggctca gactggtaaa   1920
tcccccgcag gagtgaatct tttatcattt gcatatgatc tagaagcaaa agcaaacagt   1980
ttgcccccag gaaatttgag gaactccctg aaaagagatg cacaaactat taaaacaatt   2040
caccagcaac gagtccttcc tatagaacaa tcactgagca ctctatacca aagcgtcaag   2100
atacttcaac gcacagggaa tggattgttg gagagagtaa ctaggattct agcttctctg   2160
gattttgctc agaacttcat cacaaacaat acttcctctg ttattattga ggaaactaag   2220
aagtatggga gaacaataat aggatatttt gaacattatc tgcagtggat cgagttctct   2280
atcagtgaga agtggcatc gtgcaaacct gtggccaccg ctctagatac tgctgttgat   2340
gtctttctgt gtagctacat tatcgacccc ttgaatttgt tttggtttgg cataggaaaa   2400
gctactgtat ttttacttcc ggctctaatt tttgcggtaa aactggctaa gtactatcgt   2460
cgaatggatt cggaggacgt gtacgatgat gttgaaacta tacccatgaa aaatatggaa   2520
aatggtaata atggttatca taaagatcat gtatatggta ttcacaatcc tgttatgaca   2580
agcccatcac aacattga                                                2598
```

<210> SEQ ID NO 20
<211> LENGTH: 865
<212> TYPE: PRT
<213> ORGANISM: Homo sapiens

<400> SEQUENCE: 20

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125
```

-continued

```
Phe Phe Cys Met Cys Arg Cys Cys Asn Lys Cys Gly Gly Glu Met His
    130                 135                 140
Gln Arg Gln Lys Glu Asn Gly Pro Phe Leu Arg Lys Cys Phe Ala Ile
145                 150                 155                 160
Ser Leu Leu Val Ile Cys Ile Ile Ser Ile Gly Ile Phe Tyr Gly
                165                 170                 175
Phe Val Ala Asn His Gln Val Arg Thr Arg Ile Lys Arg Ser Arg Lys
                180                 185                 190
Leu Ala Asp Ser Asn Phe Lys Asp Leu Arg Thr Leu Leu Asn Glu Thr
                195                 200                 205
Pro Glu Gln Ile Lys Tyr Ile Leu Ala Gln Tyr Asn Thr Thr Lys Asp
210                 215                 220
Lys Ala Phe Thr Asp Leu Asn Ser Ile Asn Ser Val Leu Gly Gly Gly
225                 230                 235                 240
Ile Leu Asp Arg Leu Arg Pro Asn Ile Pro Val Leu Asp Glu Ile
                245                 250                 255
Lys Ser Met Ala Thr Ala Ile Lys Glu Thr Lys Glu Ala Leu Glu Asn
                260                 265                 270
Met Asn Ser Thr Leu Lys Ser Leu His Gln Gln Ser Thr Gln Leu Ser
        275                 280                 285
Ser Ser Leu Thr Ser Val Lys Thr Ser Leu Arg Ser Ser Leu Asn Asp
    290                 295                 300
Pro Leu Cys Leu Val His Pro Ser Ser Glu Thr Cys Asn Ser Ile Arg
305                 310                 315                 320
Leu Ser Leu Ser Gln Leu Asn Ser Asn Pro Glu Leu Arg Gln Leu Pro
                325                 330                 335
Pro Val Asp Ala Glu Leu Asp Asn Val Asn Asn Val Leu Arg Thr Asp
                340                 345                 350
Leu Asp Gly Leu Val Gln Gln Gly Tyr Gln Ser Leu Asn Asp Ile Pro
            355                 360                 365
Asp Arg Val Gln Arg Gln Thr Thr Thr Val Val Ala Gly Ile Lys Arg
    370                 375                 380
Val Leu Asn Ser Ile Gly Ser Asp Ile Asp Asn Val Thr Gln Arg Leu
385                 390                 395                 400
Pro Ile Gln Asp Ile Leu Ser Ala Phe Ser Val Tyr Val Asn Asn Thr
                405                 410                 415
Glu Ser Tyr Ile His Arg Asn Leu Pro Thr Leu Glu Glu Tyr Asp Ser
                420                 425                 430
Tyr Trp Trp Leu Gly Gly Leu Val Ile Cys Ser Leu Leu Thr Leu Ile
                435                 440                 445
Val Ile Phe Tyr Tyr Leu Gly Leu Leu Cys Gly Val Cys Gly Tyr Asp
    450                 455                 460
Arg His Ala Thr Pro Thr Thr Arg Gly Cys Val Ser Asn Thr Gly Gly
465                 470                 475                 480
Val Phe Leu Met Val Gly Val Gly Leu Ser Phe Leu Phe Cys Trp Ile
                485                 490                 495
Leu Met Ile Ile Val Val Leu Thr Phe Val Phe Gly Ala Asn Val Glu
                500                 505                 510
Lys Leu Ile Cys Glu Pro Tyr Thr Ser Lys Glu Leu Phe Arg Val Leu
            515                 520                 525
Asp Thr Pro Tyr Leu Leu Asn Glu Asp Trp Glu Tyr Tyr Leu Ser Gly
    530                 535                 540
Lys Leu Phe Asn Lys Ser Lys Met Lys Leu Thr Phe Glu Gln Val Tyr
```

```
                545                 550                 555                 560
        Ser Asp Cys Lys Lys Asn Arg Gly Thr Tyr Gly Thr Leu His Leu Gln
                        565                 570                 575

Asn Ser Phe Asn Ile Ser Glu His Leu Asn Ile Asn Glu His Thr Gly
                    580                  585                 590

Ser Ile Ser Ser Glu Leu Glu Ser Leu Lys Val Asn Leu Asn Ile Phe
                595                 600                 605

Leu Leu Gly Ala Ala Gly Arg Lys Asn Leu Gln Asp Phe Ala Ala Cys
                610                 615                 620

Gly Ile Asp Arg Met Asn Tyr Asp Ser Tyr Leu Ala Gln Thr Gly Lys
        625                 630                 635                 640

Ser Pro Ala Gly Val Asn Leu Ser Phe Ala Tyr Asp Leu Glu Ala
                        645                 650                 655

Lys Ala Asn Ser Leu Pro Pro Gly Asn Leu Arg Asn Ser Leu Lys Arg
                        660                 665                 670

Asp Ala Gln Thr Ile Lys Thr Ile His Gln Gln Arg Val Leu Pro Ile
                    675                 680                 685

Glu Gln Ser Leu Ser Thr Leu Tyr Gln Ser Val Lys Ile Leu Gln Arg
                690                 695                 700

Thr Gly Asn Gly Leu Leu Glu Arg Val Thr Arg Ile Leu Ala Ser Leu
        705                 710                 715                 720

Asp Phe Ala Gln Asn Phe Ile Thr Asn Asn Thr Ser Ser Val Ile Ile
                        725                 730                 735

Glu Glu Thr Lys Lys Tyr Gly Arg Thr Ile Ile Gly Tyr Phe Glu His
                    740                 745                 750

Tyr Leu Gln Trp Ile Glu Phe Ser Ile Ser Glu Lys Val Ala Ser Cys
                755                 760                 765

Lys Pro Val Ala Thr Ala Leu Asp Thr Ala Val Asp Val Phe Leu Cys
                770                 775                 780

Ser Tyr Ile Ile Asp Pro Leu Asn Leu Phe Trp Phe Gly Ile Gly Lys
        785                 790                 795                 800

Ala Thr Val Phe Leu Leu Pro Ala Leu Ile Phe Ala Val Lys Leu Ala
                        805                 810                 815

Lys Tyr Tyr Arg Arg Met Asp Ser Glu Asp Val Tyr Asp Asp Val Glu
                    820                 825                 830

Thr Ile Pro Met Lys Asn Met Glu Asn Gly Asn Asn Gly Tyr His Lys
                835                 840                 845

Asp His Val Tyr Gly Ile His Asn Pro Val Met Thr Ser Pro Ser Gln
                850                 855                 860

His
        865

<210> SEQ ID NO 21
<211> LENGTH: 2466
<212> TYPE: DNA
<213> ORGANISM: Homo sapiens

<400> SEQUENCE: 21
atggtcagct ggggtcgttt catctgcctg gtcgtggtca ccatggcaac cttgtccctg      60
gcccggccct ccttcagttt agttgaggat accacattag agccagaaga gccaccaacc     120
aaataccaaa tctctcaacc agaagtgtac gtggctgcgc aggggagtc gctagaggtg     180 cgctgcctgt tgaaagatgc cgccgtgatc agttggacta aggatggggt gcacttgggg     240
cccaacaata ggacagtgct tattggggag tacttgcaga taagggcgc cacgcctaga     300
```

```
gactccggcc tctatgcttg tactgccagt aggactgtag acagtgaaac ttggtacttc    360
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatgaaagt     660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag gggtcttctt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380
gcagggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga atgttttgg taacagaaaa caatgtgatg   1920
aaaatagcag actttggact cgccagagat atcaacaata tagactatta caaaagacc    1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaactttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga ggaatacttg gacctcagcc aacctctcga acagtattca   2340
cctagttacc ctgacacaag aagttcttgt tcttcaggag atgattctgt tttttctcca   2400
gaccccatgc cttacgaacc atgccttcct cagtatccac acataaacgg cagtgttaaa   2460
acatga                                                             2466
```

<210> SEQ ID NO 22
<211> LENGTH: 821
<212> TYPE: PRT

<213> ORGANISM: Homo sapiens

<400> SEQUENCE: 22

```
Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
        355                 360                 365

Ile Thr Ala Ser Pro Asp Tyr Leu Glu Ile Ala Ile Tyr Cys Ile Gly
    370                 375                 380

Val Phe Leu Ile Ala Cys Met Val Val Thr Val Ile Leu Cys Arg Met
385                 390                 395                 400
```

```
Lys Asn Thr Thr Lys Lys Pro Asp Phe Ser Ser Gln Pro Ala Val His
                405                 410                 415
Lys Leu Thr Lys Arg Ile Pro Leu Arg Arg Gln Val Thr Val Ser Ala
            420                 425                 430
Glu Ser Ser Ser Ser Met Asn Ser Asn Thr Pro Leu Val Arg Ile Thr
        435                 440                 445
Thr Arg Leu Ser Ser Thr Ala Asp Thr Pro Met Leu Ala Gly Val Ser
    450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
                485                 490                 495
Met Ala Glu Ala Val Gly Ile Asp Lys Asp Lys Pro Lys Glu Ala Val
            500                 505                 510
Thr Val Ala Val Lys Met Leu Lys Asp Asp Ala Thr Glu Lys Asp Leu
        515                 520                 525
Ser Asp Leu Val Ser Glu Met Glu Met Met Lys Met Ile Gly Lys His
    530                 535                 540
Lys Asn Ile Ile Asn Leu Leu Gly Ala Cys Thr Gln Asp Gly Pro Leu
545                 550                 555                 560
Tyr Val Ile Val Glu Tyr Ala Ser Lys Gly Asn Leu Arg Glu Tyr Leu
                565                 570                 575
Arg Ala Arg Arg Pro Pro Gly Met Glu Tyr Ser Tyr Asp Ile Asn Arg
            580                 585                 590
Val Pro Glu Glu Gln Met Thr Phe Lys Asp Leu Val Ser Cys Thr Tyr
        595                 600                 605
Gln Leu Ala Arg Gly Met Glu Tyr Leu Ala Ser Gln Lys Cys Ile His
    610                 615                 620
Arg Asp Leu Ala Ala Arg Asn Val Leu Val Thr Glu Asn Asn Val Met
625                 630                 635                 640
Lys Ile Ala Asp Phe Gly Leu Ala Arg Asp Ile Asn Asn Ile Asp Tyr
                645                 650                 655
Tyr Lys Lys Thr Thr Asn Gly Arg Leu Pro Val Lys Trp Met Ala Pro
            660                 665                 670
Glu Ala Leu Phe Asp Arg Val Tyr Thr His Gln Ser Asp Val Trp Ser
        675                 680                 685
Phe Gly Val Leu Met Trp Glu Ile Phe Thr Leu Gly Gly Ser Pro Tyr
    690                 695                 700
Pro Gly Ile Pro Val Glu Glu Leu Phe Lys Leu Leu Lys Glu Gly His
705                 710                 715                 720
Arg Met Asp Lys Pro Ala Asn Cys Thr Asn Glu Leu Tyr Met Met Met
                725                 730                 735
Arg Asp Cys Trp His Ala Val Pro Ser Gln Arg Pro Thr Phe Lys Gln
            740                 745                 750
Leu Val Glu Asp Leu Asp Arg Ile Leu Thr Leu Thr Thr Asn Glu Glu
        755                 760                 765
Tyr Leu Asp Leu Ser Gln Pro Leu Glu Gln Tyr Ser Pro Ser Tyr Pro
    770                 775                 780
Asp Thr Arg Ser Ser Cys Ser Ser Gly Asp Asp Ser Val Phe Ser Pro
785                 790                 795                 800
Asp Pro Met Pro Tyr Glu Pro Cys Leu Pro Gln Tyr Pro His Ile Asn
                805                 810                 815
Gly Ser Val Lys Thr
```

820

<210> SEQ ID NO 23
<211> LENGTH: 2649
<212> TYPE: DNA
<213> ORGANISM: Homo sapiens

<400> SEQUENCE: 23

| | | | | | |
|---|---|---|---|---|---|
| atgggccctt | ggagccgcag | cctctcggcg | ctgctgctgc | tgctgcaggt | ctcctcttgg | 60 |
| ctctgccagg | agccggagcc | ctgccaccct | ggctttgacg | ccgagagcta | cacgttcacg | 120 |
| gtgcccggc | gccacctgga | gagaggccgc | gtcctgggca | gagtgaattt | tgaagattgc | 180 |
| accggtcgac | aaaggacagc | ctattttttcc | ctcgacaccc | gattcaaagt | gggcacagat | 240 |
| ggtgtgatta | cagtcaaaag | gcctctacgg | tttcataacc | cacagatcca | tttcttggtc | 300 |
| tacgcctggg | actccaccta | cagaaagttt | tccaccaaag | tcacgctgaa | tacagtgggg | 360 |
| caccaccacc | gcccccgcc | catcaggcc | tccgtttctg | gaatccaagc | agaattgctc | 420 |
| acatttccca | actcctctcc | tggcctcaga | agacagaaga | gagactgggt | tattcctccc | 480 |
| atcagctgcc | cagaaaatga | aaaggccca | tttcctaaaa | acctggttca | gatcaaatcc | 540 |
| aacaaagaca | agaaggcaa | ggttttctac | agcatcactg | gccaaggagc | tgacacaccc | 600 |
| cctgttggtg | tctttattat | tgaaagagaa | acaggatggc | tgaaggtgac | agagcctctg | 660 |
| gatagagaac | gcattgccac | atacactctc | ttctctcacg | ctgtgtcatc | caacgggaat | 720 |
| gcagttgagg | atccaatgga | gattttgatc | acggtaaccg | atcagaatga | caacaagccc | 780 |
| gaattcaccc | aggaggtctt | taaggggtct | gtcatggaag | gtgctcttcc | aggaacctct | 840 |
| gtgatggagg | tcacagccac | agacgcggac | gatgatgtga | acacctacaa | tgccgccatc | 900 |
| gcttacacca | tcctcagcca | agatcctgag | ctccctgaca | aaaatatgtt | caccattaac | 960 |
| aggaacacag | gagtcatcag | tgtggtcacc | actgggctgg | accgagagag | tttccctacg | 1020 |
| tatacccctgg | tggttcaagc | tgctgacctt | caaggtgagg | ggttaagcac | aacagcaaca | 1080 |
| gctgtgatca | cagtcactga | caccaacgat | aatcctccga | tcttcaatcc | caccacgtac | 1140 |
| aagggtcagg | tgcctgagaa | cgaggctaac | gtcgtaatca | ccacactgaa | agtgactgat | 1200 |
| gctgatgccc | ccaataccc | agcgtgggag | gctgtataca | ccatattgaa | tgatgatggt | 1260 |
| ggacaatttg | tcgtcaccac | aaatccagtg | aacaacgatg | gcattttgaa | aacagcaaag | 1320 |
| ggcttggatt | ttgaggccaa | gcagcagtac | attctacacg | tagcagtgac | gaatgtggta | 1380 |
| ccttttgagg | tctctctcac | cacctccaca | gccaccgtca | ccgtggatgt | gctggatgtg | 1440 |
| aatgaagccc | ccatctttgt | gcctcctgaa | aagagagtgg | aagtgtccga | ggactttggc | 1500 |
| gtgggccagg | aaatcacatc | ctacactgcc | caggagccag | acacatttat | ggaacagaaa | 1560 |
| ataacatatc | ggatttggag | agacactgcc | aactggctgg | agattaatcc | ggacactggt | 1620 |
| gccatttcca | ctcgggctga | gctggacagg | gaggattttg | agcacgtgaa | gaacagcacg | 1680 |
| tacacagccc | taatcatagc | tacagacaat | ggttctccag | ttgctactgg | aacagggaca | 1740 |
| cttctgctga | tcctgtctga | tgtgaatgac | aacgccccca | taccagaacc | tcgaactata | 1800 |
| ttcttctgtg | agaggaatcc | aaagcctcag | gtcataaaca | tcattgatgc | agaccttcct | 1860 |
| cccaatacat | ctcccttcac | agcagaacta | acacacgggg | cgagtgccaa | ctggaccatt | 1920 |
| cagtacaacg | acccaaccca | agaatctatc | attttgaagc | aaagatggc | cttagaggtg | 1980 |
| ggtgactaca | aaatcaatct | caagctcatg | gataaccaga | taaagacca | agtgaccacc | 2040 |
| ttagaggtca | gcgtgtgtga | ctgtgaaggg | gccgctggcg | tctgtaggaa | ggcacagcct | 2100 |

-continued

```
gtcgaagcag gattgcaaat tcctgccatt ctggggattc ttggaggaat tcttgctttg    2160
ctaattctga ttctgctgct cttgctgttt cttcggagga gagcggtggt caaagagccc    2220
ttactgcccc cagaggatga cacccgggac aacgtttatt actatgatga agaaggaggc    2280
ggagaagagg accaggactt tgacttgagc cagctgcaca ggggcctgga cgctcggcct    2340
gaagtgactc gtaacgacgt tgcaccaacc ctcatgagtg tcccccggta tcttccccgc    2400
cctgccaatc ccgatgaaat tggaaatttt attgatgaaa atctgaaagc ggctgatact    2460
gaccccacag ccccgcctta tgattctctg ctcgtgtttg actatgaagg aagcggttcc    2520
gaagctgcta gtctgagctc cctgaactcc tcagagtcag acaaagacca ggactatgac    2580
tacttgaacg aatggggcaa tcgcttcaag aagctggctg acatgtacgg aggcggcgag    2640
gacgactag                                                           2649
```

<210> SEQ ID NO 24
<211> LENGTH: 882
<212> TYPE: PRT
<213> ORGANISM: Homo sapiens

<400> SEQUENCE: 24

```
Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270
```

-continued

Glu Gly Ala Leu Pro Gly Thr Ser Val Met Glu Val Thr Ala Thr Asp
            275                 280                 285

Ala Asp Asp Asp Val Asn Thr Tyr Asn Ala Ala Ile Ala Tyr Thr Ile
290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
                340                 345                 350

Glu Gly Leu Ser Thr Thr Ala Thr Ala Val Ile Thr Val Thr Asp Thr
                355                 360                 365

Asn Asp Asn Pro Pro Ile Phe Asn Pro Thr Thr Tyr Lys Gly Gln Val
370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
                420                 425                 430

Asp Gly Ile Leu Lys Thr Ala Lys Gly Leu Asp Phe Glu Ala Lys Gln
                435                 440                 445

Gln Tyr Ile Leu His Val Ala Val Thr Asn Val Val Pro Phe Glu Val
                450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
                500                 505                 510

Pro Asp Thr Phe Met Glu Gln Lys Ile Thr Tyr Arg Ile Trp Arg Asp
                515                 520                 525

Thr Ala Asn Trp Leu Glu Ile Asn Pro Asp Thr Gly Ala Ile Ser Thr
530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
                580                 585                 590

Pro Ile Pro Glu Pro Arg Thr Ile Phe Phe Cys Glu Arg Asn Pro Lys
                595                 600                 605

Pro Gln Val Ile Asn Ile Ile Asp Ala Asp Leu Pro Pro Asn Thr Ser
                610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
                660                 665                 670

Gln Asn Lys Asp Gln Val Thr Thr Leu Glu Val Ser Val Cys Asp Cys
                675                 680                 685

-continued

```
Glu Gly Ala Ala Gly Val Cys Arg Lys Ala Gln Pro Val Glu Ala Gly
    690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Leu Phe Leu Arg Arg Arg Ala Val
                725                 730                 735
Val Lys Glu Pro Leu Leu Pro Pro Glu Asp Asp Thr Arg Asp Asn Val
                740                 745                 750
Tyr Tyr Tyr Asp Glu Glu Gly Gly Gly Glu Glu Asp Gln Asp Phe Asp
            755                 760                 765
Leu Ser Gln Leu His Arg Gly Leu Asp Ala Arg Pro Glu Val Thr Arg
    770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
                805                 810                 815
Ala Ala Asp Thr Asp Pro Thr Ala Pro Pro Tyr Asp Ser Leu Leu Val
            820                 825                 830
Phe Asp Tyr Glu Gly Ser Gly Ser Glu Ala Ala Ser Leu Ser Ser Leu
            835                 840                 845
Asn Ser Ser Glu Ser Asp Lys Asp Gln Asp Tyr Asp Tyr Leu Asn Glu
    850                 855                 860
Trp Gly Asn Arg Phe Lys Lys Leu Ala Asp Met Tyr Gly Gly Gly Glu
865                 870                 875                 880
Asp Asp
```

METHOD OF ISOLATING CIRCULATING TUMOR CELLS

CROSS-REFERENCE TO RELATED APPLICATIONS

This patent application is a national stage filing under 35 U.S.C. § 371 of International Application No. PCT/US2013/043745, filed on Apr. 31, 2013, which application claims priority to U.S. Provisional Application No. 61/760,042, filed Feb. 2, 2013, and U.S. Provisional Application No. 61/806,358, filed Mar. 28, 2013, which are incorporated herein by reference in their entireties.

STATEMENT REGARDING FEDERALLY SPONSORED RESEARCH

This invention was made with government support under federal grant number W81XWH-10-1-0483 awarded by the Department of Defense and federal grant number 5R01-CA127727-03 awarded by NIH. The U.S. Government has certain rights to this invention.

SEQUENCE LISTING

The sequence listing is filed with the application in electronic format only and is incorporated by reference herein. The sequence listing text file "WO00_ASFILED_SequenceListing-Text" was created on May 31, 2013 and is 131,252 bytes in size.

FIELD

The disclosure relates to methods for the detection and prognosis of cancer. Moreover, the disclosure provides methods for capturing and isolating circulating tumor cells (CTCs) that include the identification, detection, and optional enumeration of the CTCs that can be used in methods relating to a prognosis, diagnosis, or the treatment of cancer in a subject.

BACKGROUND

Most metazoan cells can be classified as either epithelial or mesenchymal based on morphology, behavior and molecular signatures. Epithelial tumor cells can become mesenchymal cells and vice versa via phenotypic transitions, a process known as epithelial plasticity. Epithelial cells are generally polar in the apico-basal direction, adherent to adjacent cells in the plane perpendicular to the polarity, and non-motile in the polar direction. Mesenchymal cells, in contrast, lack polarity, do not form tight interactions with neighboring cells, and are motile. In adult animals, epithelial and mesenchymal cells remain stably in one state or the other; that is, an epithelial cell does not change its properties and become mesenchymal. During development, however, epithelial cells of the early embryo give rise to all three embryonal layers (endoderm, mesoderm and ectoderm), which include mesenchymal cells (Hay, E. D., et al. *Am. J. Kidney Dis.* 1995, 26, 678-690). Therefore, these early embryonal cells have the ability to transition between epithelial and mesenchymal states. Embryos have been shown to undergo epithelial-mesenchymal transitions (EMTs) as well as mesenchymal-epithelial transitions (METs) (Acloque, H., et al. *J. Clin. Invest.* 2009, 119, 1438-1449).

Epithelial plasticity (EP) refers to the reversible loss of the epithelial cellular phenotype, a process known to occur during cancer metastasis. This EP biology has been linked in multiple studies to the risk of cancer metastasis and the acquisition of mesenchymal and/or stemness properties through the EMT process. EMT has been linked to chemoresistance, invasion, intravasation, and dissemination in multiple preclinical models of cancer. The MET process, which results in the re-expression of the epithelial phenotype, is also likely of great importance in development and metastasis and has been linked to metastatic colonization and survival of tumor cells in the metastatic niche. For example, in prostate cancer, mesenchymal biomarkers may be upregulated during androgen deprivation in prostate cancer cell lines, animal models, and in patient tumor specimens. Moreover, these biomarkers are plastic, revert upon replacement of testosterone, and are linked to an increased metastatic propensity and chemoresistance. Mesenchymal-like tumor cells may better promote local tumor invasion and intravasation/extravasation, but epithelial tumor cells may be necessary for eventual survival and proliferation in the metastatic niche, illustrating the potential relevance of the dual nature of EP in mediating the full process of metastasis.

Circulating tumor cells (CTCs), which are cells that have detached from a primary tumor and circulate in the bloodstream, have potential prognostic, predictive and surrogate implications in oncology. CTCs may constitute seeds for subsequent growth of additional tumors (metastasis) in different tissues. Thus, detection of CTCs can provide a diagnosis and/or prognosis for overall survival and therapeutic implications in subjects with cancers such as metastatic prostate and breast cancer. The number of CTCs in any patient sample (e.g., a blood sample) can be very small, which can make detection difficult. Current methods for detecting CTCs are based on the detection of epithelial cell adhesion molecule (EpCAM) expression, which is a biomarker associated with epithelial cells. However, during the process of metastasis, circulating tumor cells (CTCs) may lose their epithelial phenotype and acquire a mesenchymal phenotype that is not sufficiently captured by existing epithelial-based CTC technologies. During metastasis, tumor cells may exist as a spectrum of epithelial to mesenchymal phenotypes. CTCs may lose their epithelial phenotype and acquire a mesenchymal phenotype, which may not be captured with existing epithelial-based CTC technology and thus lead to the under-detection of CTCs under circumstances where cells undergo a decrease or loss of EpCAM expression, such as during biologic processes including EMT. Because of the role CTCs can play in the diagnosis, monitoring, and prognosis of disease in patients having cancer, any shortcoming in the detection technology needs to be addressed by the art.

There is recent evidence to suggest that CTCs with a mesenchymal phenotype are missed by CELLSEARCH® and other epithelial-based technologies. Accordingly, there is a need for methods and systems for capturing CTCs that do not rely on existing capture technologies, and methods for correlating CTC detection to diagnosis, monitoring, and prognosis of disease in cancer patients.

SUMMARY

In an aspect, the disclosure provides a method for detecting a circulating tumor cell (CTC) in a biological sample, the method comprising detecting at least one epithelial mesenchymal transition (EMT) biomarker in the biological sample.

In an aspect, the disclosure provides a kit for detecting a circulating tumor cell (CTC) in a biological sample, the kit comprising an antibody to at least one EMT biomarker and instructions for use.

In an aspect, the disclosure provides a method of predicting responsiveness of a subject having cancer to a course of cancer treatment, the method comprising: determining the level or presence of expression of at least one EMT biomarker to obtain an EMT biomarker profile and/or optionally a gene expression pattern for a CTC; and predicting the responsiveness of the subject to the cancer drug based on the EMT biomarker profile and/or optional gene expression pattern. In some embodiments the method includes: determining the level or presence of expression of at least one EMT biomarker in a sample from the subject to obtain a biomarker profile and optionally a gene expression pattern in a CTC for the subject; identifying the type of cancer from the biomarker profile and/or optional gene expression pattern, and optionally characterizing the stage of the cancer; and predicting responsiveness of the subject to the cancer drug based on any one of the biomarker pattern, the optional gene expression pattern, the type of cancer, or the stage of the cancer. Embodiments of this aspect can include detecting a number of cells captured and enumerated from a blood sample using at least one EMT biomarker applied to a sample from the subject. These cells that express the EMT biomarker are thereby captured using the EMT biomarker and could then be used to obtain a gene expression pattern in CTCs for the subject; to predict responsiveness of the subject to the cancer drug based on the obtained gene expression pattern, and for the detection of other biomarkers in these CTCs to assist in guiding therapy of that subject. These cells could also be used to measure the level of the specified EMT biomarker or other EMT biomarkers.

In an aspect, the disclosure provides a method of assessing the number of CTCs using both the traditional EpCAM based capture methodology and an EMT-marker based capture methodology. This EMT-based capture may replace or complement existing CTC capture technologies. The further capture, enumeration, and characterization of these CTCs using EMT antigen capture may further targeting delivery of a cancer drug in a subject having cancer comprising administering to the subject a cancer drug linked to an antibody specific for at least one EMT biomarker or specific drugs based on a gene expression profile or presence of this EMT biomarker.

In an aspect, the disclosure provides a method of estimating the prognosis of a subject with cancer as well as permitting a further characterization of CTCs that may predict for therapeutic responsiveness, the method comprising: determining the level of or presence of expression of at least one EMT biomarker in a sample from the subject to determine the number of CTCs in the subject and to obtain a gene expression pattern for the subject; and providing a prognosis to the subject based on the gene expression or biomarker profile pattern obtained.

In an aspect, the disclosure provides a method for monitoring progression of cancer in a subject undergoing therapeutic treatment, the method comprising detecting the level of expression or presence of expression of at least one EMT biomarker and the quantification of CTCs captured using this method in blood samples taken from the subject at a first and a second time; and comparing the first and second levels of expression; wherein a detected difference in the level of expression of the at least one EMT biomarker in the first and second samples over time indicates a change in the progression status of the cancer.

In an aspect, the disclosure provides a method for detecting cancer in a subject, the method comprising determining the presence of CTCs that express at least one EMT biomarker in a sample from the subject as compared to a normal or control sample, wherein an increased level of at least one EMT biomarker indicates presence of cancer progression or metastatic spread in the subject.

In an aspect, the disclosure provides a method of treating cancer in a subject comprising administering to the subject a cancer drug linked to an antibody that specifically binds at least one EMT biomarker.

The present disclosure is directed to a method for isolating, capturing, or enriching a circulating tumor cell from a patient, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby isolating, capturing, or enriching the circulating tumor cell. The method may further comprise confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The circulating tumor cell may have a mesenchymal phenotype. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method for detecting or identifying a circulating tumor cell in a patient, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby detecting or identifying the circulating tumor cell. The method may further comprise confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The circulating tumor cell may have a mesenchymal phenotype. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic. The present disclosure is directed to a method for isolating or capturing an intact cell from a patient, wherein the cell is β-catenin positive, DAPI positive, and CD45 negative, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the intact cell to form a solid phase-capture binding protein-intact cell complex; and separating the solid phase-capture binding protein-intact cell complex from the sample and unbound magnetic particle-capture binding protein complexes by application of an external magnetic field on the sample, thereby isolating or capturing the intact cell. The intact cell may have a mesenchymal phenotype. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of detecting and treating cancer in a subject, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, determining the level of circulating tumor cell in the solid phase-capture binding protein-circulating tumor cell complex; comparing the level of circulating tumor cell to a reference level of circulating tumor cell, detecting cancer in the subject if the level of circulating tumor cell is higher than the reference level of circulating tumor cell, cancer is detected in the subject, and administrating a therapy against cancer to the subject identified as having cancer. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of monitoring progression of cancer in a subject undergoing therapeutic treatment, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample; determining the level of circulating tumor cell in the solid phase-capture binding protein-circulating tumor cell complex; correlating the level of circulating tumor cell with the progression of cancer in the subject, wherein if the level of the circulating tumor cell is higher as compared to the level of the circulating tumor cell in an earlier biological sample from the subject, the subject is identified as having progression of cancer; and administering a therapy against cancer to the subject identified as having progression of cancer. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of determining a cancer prognosis in a subject, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample; determining the level of circulating tumor cell in the solid phase-capture binding protein-circulating tumor cell complex; comparing the level of circulating tumor cell to a reference level of circulating tumor cell, determining the cancer prognosis in the subject, wherein if the level of circulating tumor cell is higher than the reference level of circulating tumor cell, the subject is identified as having cancer, and administrating a therapy against cancer to the subject identified as having cancer. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a method of predicting responsiveness of a subject having cancer to a course of treatment, the method comprising: obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample; determining the level of circulating tumor cell in the solid phase-capture binding protein-circulating tumor cell complex; and comparing the level of circulating tumor cell to a reference level of circulating tumor cell. Determining the level of circulating tumor cell in the solid phase-capture binding protein-circulating tumor cell complex comprises confirming the circulating tumor cell. Confirming the circulating tumor cell comprises at least one of DAPI staining, β-catenin detection, CD45 detection and CD31 detection. The circulating tumor cell may be confirmed if DAPI staining is positive, β-catenin expression is positive, CD45 expression is negative, and CD31 expression is negative. The EMT biomarker may be at least one of OB-cadherin, N-cadherin, vimentin, E-cadherin, FGFR2 splice variant isoforms, or CD133. The patient may have cancer. The may comprise at least one of breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancer, carcinoma, sarcoma, and soft tissue cancer. The method may further comprise determining the presence or absence of at least one prostate cancer-specific genomic event. The at least one prostate cancer-specific genomic event may be selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof. The determining step may performed by fluorescence in situ hybridization (FISH). The biological sample may comprise a tissue sample or a fluid sample from an organism. The biological sample may comprise blood. The capture binding protein may be an antibody. The solid phase may be a microparticle. The microparticle may be magnetic or paramagnetic.

The present disclosure is directed to a kit for isolating or capturing a circulating tumor cell in a biological sample, the kit comprising an antibody linked to a magnetic particle, wherein the antibody binds specifically to at least one EMT biomarker and at least one staining reagent. The at least one EMT biomarker may include at least one of OB-cadherin, N-cadherin, vimentin, E-cadherin, FGFR2 splice variant isoforms, or CD133. The at least one staining reagent may include at least one of phycoerytherin-labeled anti-β-catenin antibody and an allophycocyanin-labeled anti-CD45 antibody.

Other aspects and embodiments of the disclosure will become apparent by consideration of the detailed description and accompanying drawings.

BRIEF DESCRIPTION OF THE DRAWINGS

FIG. 22 depicts examples of OB-cadherin captured. β-catenin-positive cellular events from men with metastatic castration-resistant prostate cancer. The top rows show single cells which are mostly CD31-positive and may represent endothelial cells, while the bottom rows show clumps of CD31-negative cells which may represent mesenchymal tumor cells.

FIG. 23 depicts (left image) immunofluorescent images of PC-3 cells stained for OB-cadherin (green) and DAPI/nucleus (blue), illustrating that PC-3 cells are somewhat heterogeneous for OB-cadherin expression; and (right image) a graph of fluorescence-activated cell sorting of PC-3 cells based on OB-cadherin expression shows that approximately 50% of the cells express OB-cadherin.

FIG. 24 depicts immunostaining and fluorescent in situ hybridization (FISH) results from a representative patient with metastatic castration-resistant prostate cancer. Columns A and B—Circulating cells captured with OB-cadherin and stained with β-catenin show same multigene FISH pattern as a CTC captured with EpCAM and stained with cytokeratin from the same patient. Androgen receptor (AR) FISH shows extra copies of the androgen receptor gene. For the ERG break FISH, yellow arrows denote missing 5' Erg signals which is indicative of TMPRSS2:ERG fusion. PTEN FISH shows homozygous deletion of PTEN gene. Column C—leukocyte from the same patient shows a cytokeratin-negative cell with a normal FISH pattern of 1 AR signal, no ERG rearrangement, and two copies of PTEN.

DETAILED DESCRIPTION

Figure 1:
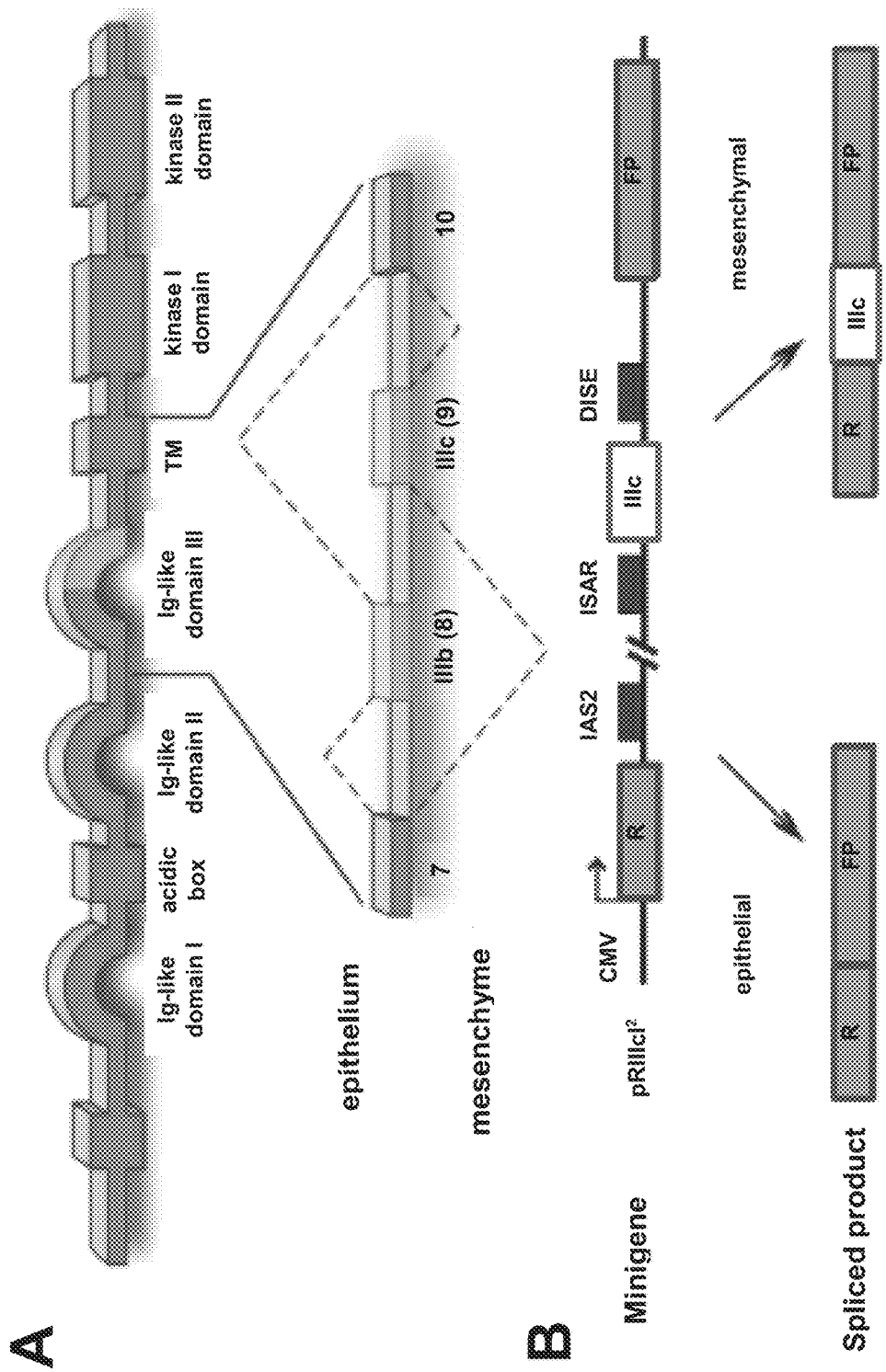
FIG. 1. (A) depicts a schematic representation of the IIIb and IIIc alternatively spliced isoforms of FGFR2. (B) is a schematic of the pRIIIcI$^2$ minigene and the fluorescence read-out. (C) is an RT-PCR analysis of the reporter (upper panel) and endogenous FGFR2 (lower panel). (D) are epifluorescence and phase-contrast pictures of clones AT3-M and AT3-T.

Before any embodiments are described in detail, it is to be understood that the claims are not limited to the details of construction and the arrangement of components set forth in the following description or illustrated in the included drawings.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

In a general sense, the disclosure provides biomarkers that have been identified to be associated with circulating tumor cells (CTCs). As described herein, one or more biomarkers of epithelial mesenchymal transition (EMT) are detectable on CTCs of patients afflicted with common epithelial malignancies. These transitional cells often display stem cell-like characteristics (stemness) and/or plasticity. Further, the disclosure provides description that metastatic propensity and epithelial phenotypic changes correlate with alternative splicing of the FGFR2 gene. The disclosure also provides that, as illustrated in the non-limiting Examples, transitional cells are found in cancer patients where many CTCs co-expressed biomarkers associated with epithelial and mesenchymal cells.

Thus, as described below EMT biomarker expression can be used to detect and quantify CTCs in a biological sample. Accordingly, methods comprising detection of EMT biomarker expression, or detection of CTCs, or a combination thereof, can be used to assess cancer prognosis, tumor invasiveness, risk of metastasis, or to stage tumors. As one of skill in the art will appreciate, any suitable method for evaluating EMT biomarker expression can be used to evaluate EMT biomarker expression according to the methods described herein including, but not limited to, detection with antibodies, real time RT-PCR, Northern analysis, Western analysis, and flow cytometry.

The disclosure also describes the development of a CTC capture method that is based on the biology of epithelial plasticity and isolates cells based on mesenchymal markers, such as N-cadherin or OB-cadherin cell surface expression. In patients with advanced breast and prostate cancer, EP biomarkers including OB-cadherin, N-cadherin, and vimentin can be detected in CTCs that are isolated by EpCAM-based ferromagnetic capture and co-express cytokeratin, which is expressed in epithelial cells. Similarly, CTCs expressing the mesenchymal markers twist and vimentin have been identified rarely in patients with early stage breast cancer but in the majority of patients with metastatic breast cancer, suggesting that transition to a mesenchymal phenotype may be important for metastasis. Furthermore, recent serial monitoring of CTCs with a mesenchymal phenotype, as defined by RNA fluorescence in situ hybridization (FISH), suggests that there may be an association between mesenchymal CTCs and disease progression in women with breast cancer.

As described herein, in patients with metastatic castration-resistant prostate cancer (CRPC) and breast cancer (BC), CTCs isolated using epithelial cell adhesion molecule (EpCAM) ferromagnetic capture expressed mesenchymal markers, including N- and OB-cadherin, suggesting phenotypic plasticity and the presence of EMT. The CTC capture method described herein involves a mesenchymal-based assay. This assay detected OB-cadherin cellular events present in men with metastatic prostate cancer but were less common in healthy individuals. This method may complement existing epithelial-based methods and may potentially be useful in patients with bone metastases.

Definitions

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody."

"Antibody fragment" as used herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region. The term "administration" or "administering," as used herein, refers to providing, contacting, and/or delivery of a cancer treatment by any appropriate route to achieve the desired effect. The cancer treatment may be administered to a subject in numerous ways including, but not limited to, orally, ocularly, nasally, intravenously, topically, as aerosols, suppository, etc. and may be used in combination.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

The term "biomarker" as used herein refers to any quantifiable biological component that is unique to a particular physiological condition (e.g., cancer). A biomarker may be a gene, an mRNA transcribed from said gene, or a protein translated from said mRNA. A measureable increase or decrease, of a biomarker level, relative to a control, such as an individual, group of individuals or populations, or alternatively, relative to subjects with cancer, may provide a diagnosis of a particular physiological condition.

"Breast cancer" as used herein refers to a type of cancer that originates from and develops in the breast.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Circulating tumor cells", "CTC" and "CTCs" as used interchangeably herein refers to cells that have shed into the vasculature from a primary tumor and circulate in the bloodstream. CTCs are considered seeds for subsequent growth of additional tumors (metastasis) in vital distant organs, triggering a mechanism that is responsible for the vast majority of cancer-related deaths.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/ solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

The term "effective dosage" as used herein means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual.

"Epithelial" and "epithelial phenotype" as used herein refer to membranous tissue composed of one or more layers of cells separated by very little intercellular substance and forming the covering the most internal and external surfaces of the body and its organs.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entirety). An acridinium compound can be used as a detectable label in a homogeneous chemiluminescent assay (see, e.g., Adamczyk et al., Bioorg. Med. Chem. Left. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

"Mesenchymal" and "mesenchymal phenotype" as used interchangeably herein refer to a type of undifferentiated loose connective tissue that can develop into the tissues of the lymphatic and circulatory systems and connective tissues throughout the body, such as bone and cartilage. Mesenchymal phenotypes may be characterized morphologically by a prominent ground substance matrix containing a loose aggregate of reticular fibrils and unspecialized cells. Mesenchymal cells can migrate easily, in contrast to epithelial cells, which lack mobility and are organized into closely adherent sheets, are polygonal in shape, and are polarized in an apical-basal orientation.

"Mesenchymal phenotypic CTC" and "mesenchymal CTC" as used interchangeably herein refer to a CTC which has a mesenchymal phenotype.

The term "normal control" or "healthy control" as used herein means a sample or specimen taken from a subject, or an actual subject who does not have cancer, or is not at risk of developing cancer.

The term "normal subject" as used herein means a healthy subject, i.e. a subject having no clinical signs or symptoms of cancer. The normal subject is clinically evaluated for otherwise undetected signs or symptoms of cancer, which evaluation may include routine physical examination and/or laboratory testing.

The term "predetermined cutoff" and "predetermined level" as used herein means an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Prostate cancer" as used herein refers to a type of cancer that develops in the prostate. Prostate cancer may be slow growing or aggressive, in which the cancer cells metastasize from the prostate to other parts of the body, particularly the bones and lymph nodes. "Metastatic prostate cancer" refers to prostate cancer that spreads outside the prostate gland to the lymph nodes, bones, or other areas. "Castration resistant prostate cancer" refers to prostate cancer disease progression despite androgen-deprivation therapy which may present as one or any combination of a continuous rise in serum levels of prostate-specific antigen, progression of pre-existing disease, or appearance of new metastases.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction to comprise a "sensitivity panel."

The term "reference activity level" or "reference" as used herein means an activity level of the biomarker in a sample group that serves as a reference against which to assess the activity level in an individual or sample group.

The term "risk assessment," "risk classification," "risk identification," or "risk stratification" as used herein interchangeably, means an evaluation of factors including biomarkers, to predict the risk of occurrence of future events including disease onset or disease progression, so that treatment decisions regarding the subject may be made on a more informed basis.

The term "sample," "test sample," "specimen," "biological sample," "sample from a subject," or "subject sample" as used herein interchangeably, means a sample or isolate of blood, tissue, urine, serum, plasma, amniotic fluid, cerebrospinal fluid, placental cells or tissue, endothelial cells, leukocytes, or monocytes, can be used directly as obtained from a subject or can be pre-treated, such as by filtration, distillation, extraction, concentration, centrifugation, inactivation of interfering components, addition of reagents, and the like, to modify the character of the sample in some manner as discussed herein or otherwise as is known in the art.

The term also means any biological material being tested for and/or suspected of containing an analyte of interest. The sample may be any tissue sample taken or derived from the subject. In some embodiments, the sample from the subject may comprise protein. Any cell type, tissue, or bodily fluid may be utilized to obtain a sample. Such cell types, tissues, and fluid may include sections of tissues such as biopsy and autopsy samples, frozen sections taken for histological purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

Methods well-known in the art for collecting, handling and processing urine, blood, serum and plasma, and other body fluids, are used in the practice of the present disclosure. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples, a pre-processed archived sample, etc.), pretreatment of the sample is an option that can be performed for mere convenience (e.g., as part of a protocol on a commercial platform). The sample may be used directly as obtained from the subject or following pretreatment to modify a characteristic of the sample. Pretreatment may include extraction, concentration, inactivation of interfering components, and/or the addition of reagents.

"Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. For example, the linking agent can include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. For examples, the solid phase can be plastic, derivatized plastic, magnetic, paramagnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "subject", "patient" or "subject in the method" as used herein interchangeably, means any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human. In some embodiments, the subject or subject may be a human or a non-human. In some embodiments, the subject may be a human subject at risk for developing or already having cancer.

"Treat", "treating" or "treatment" are each used interchangeably herein to describe reversing, alleviating, or inhibiting the progress of a disease, such as cancer, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

As described herein the ability for a cell to transition easily between epithelial-like and mesenchymal-like states (phenotypic plasticity) is a relevant determinant of malignant fitness more so than the properties of the end states. While these epithelial transitions are phenotypic, the propensity to transition (plasticity) among carcinoma cells may be determined by genotype. The majority of plastic cells may inhabit transitional intermediate states with properties of both epithelium and mesenchyme, and that these transitional cells may be particularly malignant. Such cells may be detected in: (1) tumors where the cancer cells have mixed histology, which indeed have been observed and have been classified as highly aggressive (e.g., clonal sarcomatous carcinomas of epithelial origin, which exhibit an extremely aggressive behavior, such as sarcomatoid renal cell carcinoma and carcinosarcoma of the prostate); and (2) cancer cells co-expressing epithelial and mesenchymal markers, as described herein.

The disclosure, as illustrated by the non-limiting embodiments in the Examples, provides for identification of cells that possess an intermediate phenotype—expressing epithelial and mesenchymal isoforms of FGFR2, having epithelial-like morphology and gene expression patterns, while also displaying mesenchymal cell-like migration, tumor formation, and metastases. In embodiments, these cells are identified in patients with advanced cancer, metastatic adenocarcinoma, and metastatic breast and prostate carcinomas. In some embodiments, the cells comprise CTCs. In some embodiments the CTCs co-expresses biomarkers including, for example, EpCAM, cytokeratin, and vimentin, which identify cells as both epithelial- and mesenchymal-like. In some embodiments, these CTCs in intermediate phenotypic states are identified by detecting EMT biomarkers and provide a diagnosis and/or prognosis of the state and/or degree of malignancy of a cancer.

In an aspect the disclosure provides a method for detecting CTCs in a biological sample, the method comprising detecting at least one EMT biomarker in the biological sample. In some embodiments such as illustrated in the Examples, biomarkers of EMT are present on the CTCs of patients with common epithelial malignancies. In some embodiments methods that include detection and identification of alternative splice variants of the FGFR2 gene are used to correlate to metastatic propensity and epithelial phenotypic in a CTC.

Thus, EMT biomarker expression may be used to detect CTCs. EMT biomarker expression, or detection of CTCs, or a combination thereof, may be used to assess cancer prognosis, tumor invasiveness, risk of metastasis, or to stage tumors. As mentioned above, the methods described herein can include any suitable method for evaluating EMT biomarker expression including, but not limited to, detection with antibodies, real time RT-PCR, Northern analysis, magnetic particles (e.g., microparticles or nanoparticles), Western analysis, and any method or system involving flow cytometry. In some embodiments, the methods and EMT biomarkers can be used in a commercially available system such as a system that has been approved by a regulatory agency (e.g., FDA) including, for example, CELL-SEARCH® technology (Veridex LLC). Thus, the methods can incorporate standard protocols that are known in the art. For example, embodiments comprising CELLSEARCH® technology can include detecting the presence of an EMT biomarker, and correlated to quantifying the number of circulating tumor cells (CTCs) a biological sample, (e.g., blood collected from women in need of a new treatment regimen for metastatic breast cancer, or men in need of treatment for mCRPC). Typical protocols can include drawing blood sample sizes of about 15 mL that can be collected at any particular time (suitably when the patient starts the new therapy, and then again at three to four week intervals). The number of CTCs can be correlated with disease response or progression as determined by standard radiology studies (e.g., CT scans) performed every nine to 12 weeks.

In an aspect, the disclosure relates to a method for detecting a circulating tumor cell (CTC) in a biological sample, wherein the method comprises detecting at least one EMT biomarker in the biological sample. As noted above, a biological sample can be from any tissue or fluid from an organism. In some embodiments the biological sample is from a bodily fluid or tissue that is part of, or associated with, the lymphatic system or the circulatory system of the organism. In some embodiments the biological sample is a blood sample.

The EMT and cellular plasticity biomarkers used in the methods described herein are associated with circulating tumor cells (CTCs). Accordingly, in various embodiments the methods include detecting the presence of one or more EMT biomarker and correlating that detection with the presence of a CTC, optionally quantifying the number of CTCs in the sample. As discussed herein, EMT biomarkers can include any detectable biomolecule that is associated with a transitional cell that exhibits characteristics (e.g., phenotype, or surface antigen or gene expression profiles, etc.) of plasticity, stem-like properties, invasiveness, and/or chemo-resistance of a cell. In some non-limiting embodiments, the EMT biomarker includes any of vimentin, N-cadherin, O-cadherin, E-cadherin, FGFR2 splice variant isoforms (such as, for example FGFR2 that includes or excludes either exon IIIc or exon IIIb), or CD133, or any combination of two or more thereof. In some embodiments, the EMT biomarker can include one or more of vimentin (polypeptide SEQ ID NO: 14 encoded by polynucleotide SEQ ID NO: 13), N-cadherin (polypeptide SEQ ID NO: 2 encoded by polynucleotide SEQ ID NO: 1; polypeptide SEQ ID NO: 16 encoded by polynucleotide SEQ ID NO: 15), 0-cadherin (polypeptide SEQ ID NO: 4 encoded by polynucleotide SEQ ID NO: 3; polypeptide SEQ ID NO: 18 encoded by polynucleotide SEQ ID NO: 17), E-cadherin (polypeptide SEQ ID NO: 12 encoded by polynucleotide SEQ ID NO: 11; polypeptide SEQ ID NO: 24 encoded by polynucleotide SEQ ID NO: 23), FGFR2 (polypeptide SEQ ID NO: 8 encoded by polynucleotide SEQ ID NO: 7; polypeptide SEQ ID NO: 10 encoded by polynucleotide SEQ ID NO: 9; polypeptide SEQ ID NO: 22 encoded by polynucleotide SEQ ID NO: 21), and CD133 (polypeptide SEQ ID NO: 6 encoded by polynucleotide SEQ ID NO: 5; polypeptide SEQ ID NO: 20 encoded by polynucleotide SEQ ID NO: 19). In some embodiments, the EMT biomarker can include one or more of N-cadherin, for example human N-cadherin (for example SEQ ID NO: 16, CCDS ID No: CCDS11891.1); O-cadherin, for example human O-cadherin (for example SEQ ID NO: 18, CCDS ID No: CCDS10803.0); E-cadherin, for example human E-cadherin (for example SEQ ID NO: 24, CCDS ID No:

CCDS10869.1); CD133, for example human CD133 (for example SEQ ID NO: 20, CCDS ID No: CCDS47029.1); FGFR2, for example human FGFR2 (for example SEQ ID NO: 22, CCDS ID No: CCDS31298.1); and vimentin, for example human vimentin (for example SEQ ID NO: 14, Accession No. BC000163). It will be understood by one of skill in the art that when reference is made to polynucleotides that encode polypeptides in the above embodiments as well as embodiments throughout, the polynucleotide can be disclosed as either an RNA (e.g., mRNA) or a DNA (e.g., cDNA).

The EMT biomarkers can be associated with any organism (ortholog) and in certain embodiments are EMT biomarkers associated with a human. Any portion or the entirety of an EMT biomarker can be used for detecting in the methods described herein such as, for example, an epitope of an EMT biomarker protein that binds to an antibody, or a nucleic acid sequence of an EMT biomarker an expressed or transcribed mRNA molecule that is complementary to a reporter nucleic acid probe or primer. In some embodiments, the methods provide for detecting expression of at least two EMT biomarkers. In certain embodiments, expression of vimentin and E-cadherin are detected. In certain embodiments, expression of N-cadherin and O-cadherin are detected. This measure may be used alone or in combination with another method to detect CTCs. In certain embodiments, the methods described herein may be used as a supplemental method in conjunction with CELLSEARCH® Circulating Tumor Cell Test (noted above). Thus, embodiments provide for a method as part of a dual or complementary detection system that can be used to detect and optionally quantify CTCs in a sample (e.g., comprising the detection of EpCAM and at least one EMT biomarker). The expression of at least one EMT biomarker may be used to isolate CTCs. The expression of at least one EMT biomarker may be used to count or provide a relative number or amount of CTCs, using any known method for correlating detection of a biomarker to a cell, such as a CTC. CTCs may be detected at the time of, prior to, or after metastasis.

Cancers may include, but are not limited to, breast cancer, colon cancer, lung cancer, prostate cancer, testicular cancer, brain cancer, skin cancer, rectal cancer, gastric cancer, esophageal cancer, sarcomas, tracheal cancer, head and neck cancer, pancreatic cancer, liver cancer, ovarian cancer, lymphoid cancer, cervical cancer, vulvar cancer, melanoma, mesothelioma, renal cancer, bladder cancer, thyroid cancer, bone cancers, carcinomas, sarcomas, and soft tissue cancers. Thus, the disclosure is generally applicable to any type of cancer in which expression of an EMT biomarker occurs. In certain embodiments, the cancer is a solid tumor malignancy. In certain embodiments, the cancer is breast, colon, or prostate cancer.

Expression of at least one EMT biomarker may be detected using any suitable method known in the art, including but not limited to, binding with antibodies or fragment thereof, antibodies tethered to or associated with an imaging agent, expression reporter plasmids, flow cytometry, and any suitable array scanner technology. The antibody or fragment thereof may suitably recognize a particular intracellular protein, protein isoform, or protein configuration.

As used herein, an "imaging agent" or "reporter molecule" is any entity which enhances visualization or detection of the cell to which it is delivered. Any type of detectable reporter molecule/imaging agent can be used in the methods disclosed herein for the detection of one or more EMT biomarker. Such detectable molecules are known in the art and include, for example, magnetic beads, fluorophores, radionuclides, nuclear stains (e.g., DAPI). For example, an imaging agent can include a compound that comprises an unstable isotope (i.e., a radionuclide) or a fluorescent moiety, such as Cy-5, Alexa 647, Alexa 555, Alexa 488, fluorescein, rhodamine, and the like. Suitable radionuclides include both alpha- and beta-emitters. In some embodiments, the targeting vehicle is labeled. In other embodiments, suitable radioactive moieties include labeled polynucleotides and polypeptides which can be coupled to the targeting vehicle. In some embodiments, the imaging agent comprises a radionuclide such as, for example, a radionuclide that emits low-energy electrons (e.g., those that emit photons with energies as low as 20 keV). Such nuclides can irradiate the cell to which they are delivered without irradiating surrounding cells or tissues. Non-limiting examples of radionuclides that are can be delivered to cells include $^{137}$Cs, $^{103}$Pd, $^{111}$In, $^{125}$I, $^{211}$At, $^{212}$Bi and $^{213}$Bi, among others known in the art. Further imaging agents suitable for delivery to a cell in accordance with some embodiments include paramagnetic species for use in MRI imaging, echogenic entities for use in ultrasound imaging, fluorescent entities for use in fluorescence imaging (including quantum dots), and light-active entities for use in optical imaging. A suitable species for MRI imaging is a gadolinium complex of diethylenetriamine pentacetic acid (DTPA). For positron emission tomography (PET), $^{18}$F or $^{11}$C may be delivered. Other non-limiting examples of reporter molecules are discussed throughout the disclosure.

In an aspect, the disclosure provides a kit for detecting CTCs in a sample. In embodiments, the kit comprises an antibody to at least one EMT biomarker. The antibody in the kit can be connected to or associated with an imaging agent. In embodiments, the kit can comprise an antibody to at least one EMT biomarker, wherein the antibody is associated a magnetic bead. The magnetic bead may be used for ferromagnetic separation and enrichment of CTCs.

Aspects also relate to methods of predicting responsiveness of a subject to a cancer drug. The methods may comprise determining the level of expression of at least one EMT biomarker in a sample from the subject. The level of expression of at least one EMT biomarker may be used to obtain a gene expression pattern in CTCs for the subject. The methods may further comprise predicting responsiveness of the subject to the cancer drug based on the gene expression pattern obtained. Genome variation in CTCs from the subject may also be determined.

Also provided are methods of providing a cancer prognosis to a subject. The methods may comprise determining the level of expression of at least one EMT biomarker in a sample from the subject. The level of expression of at least one EMT biomarker may be used to determine the number of CTCs in the sample. The CTCs may be captured using at least one EMT biomarker. The level of expression of at least one EMT biomarker may be used to determine a gene expression pattern in the CTCs for the subject. A prognosis may be provided to the subject based on the gene expression pattern obtained.

Also provided are methods for following the progress of cancer in a subject. The methods may comprise determining the level of expression of at least one EMT biomarker in samples from the subject at a first and a second time, and comparing the first and second levels of expression. The level of expression of at least one EMT biomarker in the sample may be determined over time, such as following initiation of a new cancer therapy. The level of expression of at least one EMT biomarker in the sample may be used to determine the number or amount of CTCs. An increase between the first and second levels may indicate progression of the cancer. A decrease between the first and second levels may indicate remission or response of the cancer to the therapy. No difference between the first and second levels may indicate arrest or stability in the progression of the cancer.

Also provided are methods of screening for cancer in a subject. The methods may comprise determining the level of expression of at least one EMT biomarker in a sample from the subject. The level of expression of at least one EMT biomarker may be used to determine the amount or number of CTCs in the subject. The level of expression of at least one EMT biomarker may be compared to a normal or control sample. An increased level of at least one EMT biomarker may indicate presence of cancer in the subject.

Also provided are methods of arresting cell growth or inducing cell death of a cancer cell expressing an EMT biomarker. The methods include contacting the cancer cell with a conjugate capable of mediating intracellular delivery of an agent, such as the antibodies to EMT markers described herein. The agent is capable of arresting or attenuating the growth of the cell or inducing cell death through any mechanism after agent internalization. The cancer cell may be contacted with the conjugate in vitro, in vivo, or ex vivo. These methods may be useful in treating cancer by directly targeting cancer cells expressing an EMT biomarker for delivery of agents capable of decreasing or arresting cell growth or inducing cell death.

The disclosure also provides for targeted therapeutic methods and molecules that comprise an anti-cancer agent linked to a binding agent that targets at least one EMT as described herein. In some embodiments the link between the anti-cancer agent and the binding agent is a covalent bond. In some embodiments the link is formed by strong electrostatic interactions (hydrogen bonds, hydrophilic/hydrophobic interaction, or oppositely charged moieties, and the like). Any anti-cancer agent can be used in such molecules and therapeutic methods, and can be selected by one of skill in the art based on the type of cancer to be treated, the progress/stage of the cancer, potential adverse drug interactions, dosage requirements, administration schedule, and the like.

Method of Isolating, Capturing, or Enriching Circulating Tumor Cells

With the importance of EP in metastasis, the disclosure identifies CTCs that have lost their epithelial phenotype in patients, such as patients with advanced prostate cancer, using a mesenchymal-based capture method. Such a method may complement or replace existing epithelial-based approaches by capturing cells that have reduced or absent EpCAM expression.

The present disclosure is directed to methods of isolating, capturing or enriching CTCs using any EMT biomarker, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby isolating, capturing, or enriching the circulating tumor cell. The EMT biomarker may include OB-cadherin, N-cadherin, vimentin, E-cadherin, FGFR2 splice variant isoforms, or CD133.

a) OB-Cadherin

OB-cadherin, also known as cadherin-11 and O-cadherin, is encoded by the CDH11 gene and was first identified in mouse osteoblasts. OB-cadherin is a homophilic cell adhesion molecule that mediates osteoblast adhesion during bone development. Aberrant OB-cadherin expression has been recognized in breast, gastric, and prostate cancers. OB-cadherin may be involved in prostate cancer metastasis. OB-cadherin expression was shown in CTCs (see FIG. 1).

In human prostate cancer, examination by immunohistochemistry showed increased expression of OB-cadherin in bone metastases compared with the primary tumor. Although the exact mechanism of how OB-cadherin expression facilitates bone metastasis is unclear, OB-cadherin is known to mediate adhesion between PC cells and osteoblasts. Preclinically, in PC-3 cells, when OB-cadherin is silenced by shRNA and the silenced cells are injected into mice, fewer bone metastases develop, while metastases in other organs was unaffected. In addition, induction of OB-cadherin expression has been linked to EMT/EP biology in other model systems. Furthermore, androgen depletion leads to OB-cadherin upregulation, suggesting a role for OB-cadherin in castration-resistant disease progression. Finally, given that lethal metastatic prostate cancer invariably spreads to bone in the vast majority of men, OB-cadherin positive CTCs may be detectable in the blood of men with metastatic CRPC.

Antibodies directed against OB-cadherin were attached to iron particles to form a novel ferrofluid that may replace or complement EpCAM ferrofluid in the FDA-approved CELLSEARCH® technology. After OB-cadherin expressing cells are enriched from whole blood immunomagnetically, additional characterization steps follow to ensure that the captured cells are the cells of interest, such as measuring levels of an EMT-independent characterization protein, such as β-catenin. The antibody may bind to the extracellular domain of OB-cadherin.

b) N-Cadherin

N-cadherin, also known as neural cadherin (NCAD) and cadherin-2 (CDH2) is encoded by the CDH2 gene. N-Cadherin is commonly found in cancer cells and provides a mechanism for transendothelial migration. When a cancer cell adheres to the endothelial cells of a blood vessel, it up-regulates the src kinase pathway, which phosphorylates beta-catenins attached to both N-cadherin and E-cadherins. This causes the intercellular connection between two adjacent endothelial cells to fail and allows the cancer cell to slip through. The antibody may bind to the extracellular domain of N-cadherin.

Methods of Confirming Circulating Tumor Cells

Given that CTCs are extraordinarily rare relative to other circulating cells, the isolation of CTCs involves the identification and exclusion of cells expressing the pan-leukocyte marker CD45. Circulating CD45 negative cells are not necessarily tumor-derived, however, but instead may represent normal blood vessel or stromal cells, circulating mesenchymal cells or stem cells, or other host cells that exist in rare quantities in the circulation. Circulating endothelial cells result from blood vessel wall turnover, and bone marrow-derived endothelial progenitor cells may circulate in the setting of neovascularization of ischemic tissue and tumor formation. These cells are all CD45 negative and CD31 positive. Also CD45 negative but CD31 negative, mesenchymal stromal cells (MSCs) are a more diverse group of cells that may be bone marrow-, peripheral blood-, or fat-derived. MSCs are multipotent cells that may differentiate into a variety of stromal cell types, circulate in inflammatory disorders, and are under active investigation for use in regenerative medicine and other conditions. The significance of circulating MSCs in cancer remains unclear. Thus, any CTC detection method involves distinguishing tumor cells from a range of other rare non-tumor cells in the circulation that may express non-epithelial biomarkers. Confirmation of CTCs may include detecting β-catenin, CD31, CD45, cytokeratin, and/or PSA, staining with DAPI, and/or detecting a prostate cancer-specific genomic event. For example, a CTC may be confirmed if DAPI staining is positive, β-catenin expression is positive, CD45 expression is negative, and CD31 expression is negative. The detection of β-catenin, CD31, CD45, cytokeratin, and/or PSA may be performed using antibodies against β-catenin, CD31, CD45, cytokeratin, and/or PSA, wherein the antibodies are labeled.

a) β-Catenin

β-catenin, encoded by the CTNNB1 gene, has multiple functions in cancer cells, including cadherin-mediated cell adhesion and involvement in the Wnt signaling pathway. When Wnt ligands are absent, β-catenin is phosphorylated and degraded. When Wnt ligands are present, β-catenin moves to the nucleus and activates target genes linked to EMT/invasion, proliferation, and survival in multiple cancers. In prostate cancer specifically, β-catenin may act as cofactor with the androgen receptor and increased expression and change in localization has been observed in advanced disease. β-catenin expression may be a constant finding regardless of the epithelial or mesenchymal phenotypic nature of a CTC. Using β-catenin expression to identify CTC does not have the epithelial bias associated with using cytokeratin. An antibody that binds to β-catenin may be used to detect β-catenin.

b) CD31

Cluster of differentiation 31 (CD31), also known as platelet endothelial cell adhesion molecule (PECAM-1), is encoded by the PECAM1 gene and plays a role in removing aged neutrophils from the body. CD31 is found on the surface of platelets, monocytes, neutrophils, and some types of T-cells, and makes up a large portion of endothelial cell intercellular junctions. CD31 is normally found on endothelial cells and used in immunohistochemistry to demonstrate the presence of endothelial cells in histological tissue sections. An antibody that binds to CD31 may be used to detect CD31.

c) CD45

Cluster of differentiation 45 (CD45), also known as protein tyrosine phosphatase, receptor type, C and leukocyte common antigen, is encoded by the PTPRC gene. CD45 is used to identify leukocytes. An antibody that binds to CD45 may be used to detect CD45.

d) Cytokeratin

Cytokeratins are keratin-containing intermediate filaments found in the intracytoplasmic cytoskeleton of epithelial tissue. Cytokeratin-expressing cancer cells lose their cytokeratin expression after undergoing epithelial-mesenchymal transition, with up to 20% of cells having no detectable cytokeratin. A protein other than cytokeratin may identify a pure mesenchymal CTC.

e) PSA

Prostate-specific antigen (PSA), also known as gamma-seminoprotein or kallikrein-3 (KLK3), is a glycoprotein enzyme encoded in humans by the KLK3 gene. PSA is a member of the kallikrein-related peptidase family and is secreted by the epithelial cells of the prostate gland. PSA is present in small quantities in the serum of men with healthy prostates, but is often elevated in the presence of prostate cancer or other prostate disorders.

f) DAPI

DAPI, also known as 4',6-diamidino-2-phenylindole, is a fluorescent stain that binds strongly to A-T rich regions in DNA. It is used extensively in fluorescence microscopy. DAPI can pass through an intact cell membrane therefore it can be used to stain both live and fixed cells.

g) Prostate Cancer-Specific Genomic Event

A CTC may be confirmed by detecting the presence or absence of at least one prostate cancer-specific genomic event. The at least one prostate cancer-specific genomic event may be androgen receptor amplification, phosphatase and tensin homolog (PTEN) loss, gene fusion of transmembrane protease, serine 2 (TMPRSS2) gene and ETS related (ERG) gene, and combinations thereof. For example, the detection of the presence of androgen receptor amplification, phosphatase and tensin homolog (PTEN) loss, gene fusion of transmembrane protease, serine 2 (TMPRSS2) gene and ETS related (ERG) gene may indicate and/or confirm that the CTC is a prostate cancer cell. The detection of a prostate cancer-specific genomic event may be performed using fluorescent in situ hybridization.

Method of Detecting or Identifying Circulating Tumor Cells

The present disclosure is directed to methods of detecting or identifying CTCs using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby detecting or identifying the circulating tumor cell.

Methods for Isolating or Capturing an Intact Cell from a Patient

The present disclosure is directed to methods of isolating or capturing an intact cell from a patient, wherein the intact cell is β-catenin positive, DAPI positive, and CD45 negative, using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; and separating the solid phase-capture binding protein-circulating tumor cell complex from the sample and unbound magnetic particle-capture binding protein complexes by application of an external magnetic field on the sample, thereby isolating or capturing the intact cell. The intact cell may be a mesenchymal phenotypic cell, such as mesenchymal CTC.

Method of Detecting Cancer in a Subject

The present disclosure is directed to methods of detecting cancer in a subject using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; comparing the level of circulating tumor cell to a reference level of circulating tumor cell; and detecting cancer in the subject if the level of circulating tumor cell is higher than the reference level of circulating tumor cell, cancer is detected in the subject. The cancer may be at least one cancer, as described above. The method may further include administering a therapy against cancer to the subject identified as having cancer.

Method of Monitoring Progression of Cancer in a Subject Undergoing Therapeutic Treatment The present disclosure is directed to methods of monitoring progression of cancer in a subject undergoing therapeutic treatment using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; and correlating the level of circulating tumor cell with the progression of cancer in the subject, wherein if the level of the circulating tumor cell is higher as compared to the level of the circulating tumor cell in an earlier biological sample from the subject, the subject is identified as having progression of cancer. The method may further include administering a therapy against cancer to the subject identified as having cancer.

Method of Determining a Cancer Prognosis in a Subject

The present disclosure is directed to methods of determining a cancer prognosis in a subject using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; comparing the level of circulating tumor cell to a reference level of circulating tumor cell; and determining the cancer prognosis in the subject, wherein if the level of circulating tumor cell is higher than the reference level of circulating tumor cell, the subject is identified as having cancer. The method may further include administering a therapy against cancer to the subject identified as having cancer.

Method of Predicting Responsiveness of a Subject Having Cancer to a Course of Treatment The present disclosure is directed to methods of predicting responsiveness of a subject having cancer to a course of treatment using EMT biomarkers, as described above. The method includes obtaining a biological sample from a patient; obtaining at least one capture binding protein, wherein the capture binding protein is linked to a solid phase to form a solid phase-capture binding protein complex; contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex; separating the solid phase-capture binding protein-circulating tumor cell complex from the sample and unbound magnetic particle-capture binding protein complexes by application of an external magnetic field on the sample, thereby isolating or capturing the intact cell; determining the level of circulating tumor cell in the solid phase-capture binding protein-circulating tumor cell complex; and comparing the level of circulating tumor cell to a reference level of circulating tumor cell.

Treatment

The subject identified in the methods described above as having a level of circulating tumor cell higher than or equal to a reference level is identified as a patient having cancer. The subject is then treated for the cancer.

a) Prostate Cancer

The subject identified in the methods described above having levels of circulating tumor cell greater than or equal to a reference level is identified as a patient having prostate cancer. The subject is then treated for the prostate cancer. Treatments may include watchful waiting or active surveillance, surgery, cryosurgery, high-intensity focused ultrasound, radiation, hormone therapy, chemotherapy, and targeted therapy. Examples of surgery include pelvic lymphadenectomy, radical prostatectomy (retropubic prostatectomy and perineal prostatectomy), transurethral resection of the prostate, and laparoscopic prostatectomy. Examples of radiation therapy include high-energy x-rays (external and internal radiation therapy), proton beam radiation, and intensity-modulated radiation therapy. Examples of hormone therapy include luteinizing hormone-releasing hormone agonists, such as leuprolide (Lupron, Eligard), goserelin, triptorelin (Trelstar), histrelin (Vantas), and buserelin, antiandrogens, such as flutamide, bicalutamide (Casodex), and nilutamide (Nilandron), ketoconazole, orchiectomy, estrogen, and aminoglutethimide. Examples of chemotherapeutic drugs include abiraterone acetate (Zytiga), cabazitaxel, degarelix, docetaxel, enzalutamide (Xtandi), cabazitaxel (Jevtana), leuprolide acetate (Lupron, Lupron Depot, Lupron Depot-3 Month, Lupron Depot-4 Month, Lupron Depot-Ped, Viadur), prednisone, sipuleucel-T (Provenge), estramustine (Emcyt), mitoxantrone (Novantrone), vinorelbine (Navelbine), paclitaxel (Taxol), cyclophosphamide (Cytoxan), etoposide (VP-16), G-1 (a GPR30 agonist/stimulator), and docetaxel (Taxotere).

b) Breast Cancer

The subject identified in the methods described above having levels of circulating tumor cell greater than or equal to a reference level is identified as a patient having breast cancer. The subject is then treated for the breast cancer. Treatment may include surgery, radiation therapy, bone-directed therapy, chemotherapy, hormone therapy, and targeted therapy. Examples of surgery include lumpectomy, quadrantectomy, mastectomy, such as simple mastectomy, skin-sparing mastectomy, modified radical mastectomy, prophylactic mastectomy, and radical mastectomy, prophylactic ovary removal, cryotherapy, and lymph node surgery, such as axillary lymph node dissection and sentinel lymph node biopsy. Examples of radiation therapy include external beam radiation, such as accelerated breast irradiation and 3D-conformal radiotherapy, and brachytherapy (internal radiation), such as interstitial brachytherapy, intracavitary brachytherapy, and intraoperative radiation. Examples of bone-directed therapy include bisphosphonates and denosumab. Examples of chemotherapy include anthracyclines, such as doxorubicin (Adriamycin, Doxil), epirubicin (Ellence), and daunorubicin (Cerubidine, DaunoXome), capecitabine (Xeloda), carboplatin (Paraplatin), cisplatin, cyclophosphamide (Cytoxan), eribulin (Halaven), fluorouracil (also called 5-fluorouracil or 5-FU; Adrucil), gemcitabine (Gemzar), ixabepilone (Ixempra), methotrexate (Amethopterin, Mexate, Folex), mitoxantrone (Novantrone), mutamycin (Mitomycin), taxanes, such as paclitaxel (Taxol, Abraxane), and docetaxel (Taxotere), thiotepa (Thioplex), vincristine (Oncovin, Vincasar PES, Vincrex), and vinorelbine (Navelbine). Examples of hormone therapy include aromatase inhibitors, such as anastrozole (Arimidex), exemestane (Aromasin), and letrozole (Femara), selective estrogen receptor modulators (SERMs), such as tamoxifen (Nolvadex), raloxifene (Evista), and toremifene (Fareston), and estrogen-receptor downregulators, such as fulvestrant (Faslodex). Examples of targeted therapy include trastuzumab (Herceptin), lapatinib (Tykerb), bevacizumab (Avastin), pertuzumab (Perjeta), and everolimus (Afinitor).

Kits

Provided herein is a kit, which may be used for isolating, capturing or enriching CTCs from a sample. The kit comprises at least one component for isolating, capturing or enriching CTCs from a sample and instructions for isolating, capturing or enriching CTCs from a sample. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one antibody that specifically binds to at least one EMT biomarker. The antibody may be an EMT biomarker capture antibody. The antibody may include an antibody against OB-cadherin or N-cadherin. The antibody may be associated with a solid support. The solid support may be a magnetic bead. The magnetic bead may be used for ferromagnetic separation and enrichment of CTCs.

The kit may also comprise at least one staining reagent. The at least one staining reagent may comprise an antibody which is detectably labeled. The antibody may include an antibody against a biomarker which is used to confirm the CTC. The biomarker may be β-catenin, CD45 or CD31. The at least one staining reagent may include of phycoerytherin-labeled anti-β-catenin antibody and an allophycocyanin-labeled anti-CD45 antibody.

The kit may also comprise a calibrator or control and/or at least one container for conducting the isolation, capturing, or enrichment of CTCs. The kit may comprise all components, i.e., reagents, standards, buffers, diluents, etc., which are necessary to perform the isolation, capturing, or enrichment of CTCs.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

EXAMPLES

Example 1. Materials and Methods

Plasmids and Cell Culture.

The minigene used (pRIIIcl$^2$) was previously described (S. Oltean et al., *Proc Natl Acad Sci USA* 2006, 103, 14116, incorporated herein by reference in its entirety). All cell lines were cultured in low glucose DMEM (Invitrogen) with 10% FBS and 15 IJg/mL blasticidin. Single cell progenies were isolated from a population of AT3 cells stably transfected with pRIIIcl$^2$ minigene by limiting dilution to produce a concentration of 1 cell/10 wells and plated on 96-well plates. Cells were counted using a hemocytometer to obtain an initial concentration of $1 \times 10^5$ cells/mL. Through a series of progressive dilutions a final concentration of 1 cell/mL was obtained and 100 IJI were pipetted in each well of three 96-well plates. All wells were monitored through bright field microscopy, those appearing to contain more than one cell were excluded, and those containing single cells were further cultured into 25 mL flasks. 16 of an expected 27 clones were obtained using this procedure in a first round.

To measure cell population growth rate in vitro, cells were plated at 50,000/well in 6-well dishes. Viable cells were counted using Trypan Blue staining at 24, 48, 72, and 96 h.

Animals and Tumor Cell Implantation.

Cells were trypsinized, washed, and resuspended in PBS at a final concentration of $3 \times 10^5$ cells/mL, and kept on ice for less than 30 minutes before implantation. Cells ($3 \times 10^5$) were injected subcutis in both flanks of Copenhagen 2331 rats (Harlan Labs, Indianapolis, Ind.; 75-90 g, 2 months of age). Animals were continuously monitored for tumor growth. All animal procedures were approved by the Duke University Institutional and Animal Care and Use committee and followed NIH guidelines. Sacrifice curves were compared using a Mantel-Haenszel logrank test. Tumor volume was compared using an unpaired t test. Prism 4.0c for the Macintosh (Graphpad, La Jolla, Calif.) was used for statistical analyses.

Histological Sections and Analysis.

Excised tumors and lungs were washed in PBS at room temperature. Depending on the size of the lungs, they were frozen either together or separately. The tumor sections and the lungs were placed in cryomolds, embedded in optimal-cutting-temperature tissue sectioning medium (Sakura Finetek, Torrance, Calif.), snap-frozen in liquid nitrogen, and stored at 80° C. Slides for fluorescence imaging were prepared as follows: the tissue was incubated for 2-3 h at −20° C. to equilibrate the temperature and then sectioned with a microtome. The sections (15 µm) were placed on glass slides, fixed in 4% (wt/vol) paraformaldehyde for 30 min at room temperature, and rinsed in PBS at room temperature. The slides were mounted with gel/mount media (Biomeda, Foster City, Calif.). The sections were analyzed by using an Olympus (Melville, N.Y.) IX 71 epifluorescence microscope, and images were acquired by using an Olympus DP70 digital camera. Image processing was done with DP Controller software (Olympus). For hematoxylin-eosin staining after fluorescence imaging, the slides were incubated in warm water for 15-20 minutes for the cover slip to come off, slides were dried, and staining was performed according to standard procedure.

RNA Extraction from Tumor Sections.

Sections were fixed in 4% (wt/vol) paraformaldehyde for 5 minutes, rinsed in PBS, and imaged. DsRED+ and DsRED− regions of the sections were marked on the slide. The slide was immersed in warm water for 5 minutes to remove the coverslip and the DsRED+ and DsRED− regions scraped off RNA isolation was further performed as described before (N. Masuda, T. Ohnishi, S. Kawamoto, M. Monden, K. Okubo, Nucleic Acids Res 1999, 27, 4436, incorporated herein by reference in its entirety). Briefly, samples were treated with proteinase K in digestion buffer containing SDS, and further isolation of RNA was performed using the RNeasy kit (QIAGEN, Valencia, Calif.).

Immunoblots.

Cells were collected from confluent 25 cm² tissues flasks by scraping, washed in PBS, and lysed in sample buffer. Whole cell lysates were serially diluted in sample buffer, fractionated via 7.5% SDS-PAGE, and transferred to PVDF. Membranes were cut in half. The bottom half was probed with anti-β-actin at 1:1000 or 1:5000 (Santa Cruz Biotechnology, CA, 47778) as an internal loading control, while the top half was probed with anti-CD 133 (Santa Cruz Biotechnology, CA, 30219) at 1:200 or anti-CD44 (Santa Cruz Biotechnology, CA, 7946) at 1:200.

Gene Expression Analysis.

Triplicate cultures of AT3-M and AT3-T cells were grown to ~60% confluency. Total RNA was isolated using the RNeasy kit (Qiagen, Valencia, Calif.), and triplicate samples were submitted to the Duke Microarray Facility. Gene expression analysis was performed using the R027K rat spotted arrays 3.0 (Operon, Huntsville, Ala.). Bioinformatical analysis of expression differences between AT3-M and AT3-T cells was done using the GeneSpring GX software version 7.3.1 (Agilent Technologies, Durham, N.C.). The data files (representing signals for 26,986 gene probes in all six data points, three for AT3-M and three for AT3-T) were normalized using the feature: per Spot and per Chip-intensity dependent (lowess) normalization. The resulting gene list was used to determine the significantly differentially expressed genes between AT3-M and AT3-T using the "Filtering on Volcano plot" feature with the following characteristics: (1) Test type: Parametric test, did not assume variances equal; (2) Multiple testing correction: None; (3) Fold Difference: Twofold or greater and a P-value cutoff of 0.05.

Analysis of Human Circulating Tumor Cells.

Patients eligible for the CTC biomarker protocols included (1) men with progressive CRPC, with metastatic progression by PSA (two consecutive rises over nadir separated by >1 week) or radiologic criteria (RECIST or new bone scan lesions), a PSA≥5, age≥18 years; or (2) women with mBC with disease progression or with initiation of a new systemic therapy, who were >18 years of age, and who were at least 7 days from treatment with an anthracycline-containing regimen. Blood (15 mL) was collected from patients and processed within 48 hours at the Duke University CTC lab using the Cell Search System (Veridex, Raritan, N.J.). Veridex profile kits were used, which isolate EpCAM positive cells without additional staining. The isolated cells were either processed immediately or stored overnight in 4% paraformaldehyde and processed the next day. Immunostaining was done on teflon coated slides. Briefly, cells were pipetted into the wells of the slides and left to settle for ~30 minutes followed by standard immunostaining procedures with careful aspiration to minimize cell loss. An initial ferromagnetic wash using a benchtop magnet was performed to further isolate CTCs, with resuspension of the cell pellet after magnet release 100 uL PBS. Following 4% PFA fixation and permeabilization with PBT (PBS with 2% Triton) and blocking with 10% goat serum for 30 minutes, triple immunostaining was performed using CD45 antibody (AbCam #33533-50) labeled with Alexa 647, cytokeratin (AbD Serotec #MCA1907HT) labeled with Alexa 555, and Vimentin (BD Biosciences, San Jose, Calif. #550513) labeled with Alexa 488. Nuclear staining with 4',6-diamidino-2phenylindole (DAPI) was then performed. A mesenchymal CTC (an event) was defined as an intact cell by microscopic examination, containing an intact nucleus and expressing cytokeratin but lacking CD45 staining, using appropriate controls (see Table 1 for antibodies and controls). Human peripheral blood mononuclear cells (PBMCs), obtained by Ficoll purification of buffy coats from normal donors, were kindly provided by Micah Luftig (Duke University, Durham N.C.) and used as control cells for CD45 expression. Linear regression analysis was performed to compare CTC count (standard Cellsearch method) against the proportion of CTCs that co-express vimentin. Goodness of fit was tested by analysis of variance.

TABLE 1

EMT/Stemness Antigens to be assessed in CTCs.

| Antigen | Product | Positive Control | Negative Control | Leukocyte Expression | Dilution |
|---|---|---|---|---|---|
| Vimentin | BD Biosciences, mouse monoclonal IgG1 | PBMCs, PC-3, DU145 | T47D, LnCAP | Yes | 2:225 |
| N-cadherin | DAKO, mouse monoclonal IgG1, 6G11 | Sarcoma, rat brain, PC-3 | DU145, T47D, mock | No | 4:225 |
| Cytokeratin (pan) | AbD Serotec, mouse monoclonal IgG1, MCAI907HT, clone AEI/AE3 | T47D, DU145 | PC-3, PBMCs | No | 2:45 |
| CD45 | Invitrogen, mouse IgG1, HI30, MHCD4500 | PBMC | PC-3, DU145 | Yes | 1:45 |
| CD133 | Santa Cruz mouse monoclonal IgG, sc-130127 | CaCo-2 colon cancer cells | Mock | Variable | 4:225 |

The slides were mounted with gel/mount media (Biomeda, Foster City, Calif.). The slides were analyzed with an Olympus (Melville, N.Y.) IX 71 epifluorescence microscope, and images were acquired using an Olympus DP70 digital camera. Image processing was done with DP controller software (Olympus). All fields were analysed, with each cytokeratin positive nucleated cell that was CD45 negative being counted as a CTC. Positive control cells for each antibody included PC-3 cells for vimentin, peripheral blood mononuclear cells (PBMCs) for CD45, and T47D breast cancer cell lines for cytokeratin. A similar volume of reaction mix without antibody was used for negative controls.

Media exchange experiments. The cells of AT3-T or AT3-M clones were plated at a concentration of 150,000 cells/2 mL of media in 6-well plates and allowed to incubate for 24 h. The conditioned media was then filtered using a 0.22 µm filter, and then immediately allowed to incubate with cells of the other clone, which was plated at the same concentration and had its media aspirated and cells washed with 2 mL of PBS. All cells with media replaced were incubated for 72 h, and phase and epifluorescent microscopy was used to monitor cell phenotypes 24, 48, and 72 h after treatment. Control plates, in which media was conditioned, cells washed with PBS and media added back to the same cells, were also used.

Scratch-Wound Assay.

Cells were plated and left to grow to nearly 100% confluency in 6-well dishes. A wound was simulated by scratching the cells with a sterile 200 IJI pipette tip. The wells were washed twice with PBS and fresh media added. Pictures were taken in the same marked spot at 0, 24, and 48 h. Percent migration was calculated as (width at 0 h-width at 24 or 48 h) 1 width at 0 h×100. Relative migration was compared using two-way analysis of variance via Prism 4.0c for the Macintosh (Graphpad, La Jolla, Calif.).

Matrigel Assay.

Matrigel assay was performed per manufacturer's indications (BD Biosciences). Briefly, after rehydration, $2 \times 10^5$ cells were plated either in the control or in the matrigel-coated inserts and incubated for 22 h. Following incubation, the non-invading cells from the upper-part of the inserts were removed using cotton-tipped swabs. The cells from the lower part of the membrane were stained with hematoxylin-eosin, membranes were removed, placed on a slide and observed under the microscope.

Immunohistochemical (IHC) Analysis of Metastases.

Under the same informed consent protocol as the analysis of human circulating tumor cells described above, men undergoing CTC collection additionally consented to have a radiologic-guided metastatic biopsy for analysis of biomarker expression by IHC. Samples were obtained through core needle biopsies during light sedation, and immediately formalin-fixed and paraffin embedded. For analysis, slides were deparaffinized, rehydrated, and endogenous peroxidase was inactivated for 30 min. in 0.3% $H_2O_2$ (hydrogen-peroxide) in methanol. Specific antigen retrieval steps were performed for individual antigens. Three markers were evaluated by IHC: vimentin (M7020, Dako, 1:150; antigen retrieval with pepsin treatment at 37° C. for 15 minutes), cytokeratin cocktail (18-0132, Invitrogen, 1:50 and 349205, BD Biosciences 1:50, antigen retrieval with pepsin treatment at 37° C. for 15 minutes), and CD45 (M0701, Dako, 1:200; antigen retrieval with sodium citrate 10 mM, pH 6.0 at 100° C. for 30 minutes). Primary antibody was incubated for 60 minutes at room temperature. Dako Envision horseradish peroxidase secondary antibody was used for 30 minutes at room temperature and the signal was detected with DAB reagent (Vector kit SK 4100). Slides were counter stained with hematoxylin and eosin and assessed by a trained pathologist for expression using appropriate positive (localized prostate tissue microarray sections) and negative controls (mock antibody) for each marker.

Statistical Analyses.

To determine the significantly differentially expressed genes between AT3-M and AT3-T the GeneSpring GX "Filtering on Volcano plot" feature was used with the following characteristics: (1) Test type: Parametric test, don't assume variances equal; (2) Multiple testing correction: None; (3) Fold Difference: Twofold or greater and a P-value cutoff of 0.05. To compare CTC count (standard CELLSEARCH® method) against the proportion of CTCs that co-express vimentin, N-cadherin, or CD133, linear regression analysis was performed. Goodness of fit was tested by analysis of variance.

Example 2. Isolation of Individual AT3 Clones that Inhabit an Intermediate Phenotypic State The alternative splicing of FGFR2 transcripts, which produces either FGFR2-IIIb or -IIIc variants in epithelial and mesenchymal cells respectively, is exquisitely regulated (FIG. 1A). In FIG. 1A is a schematic representation of the IIIb and IIIc alternatively spliced isoforms of FGFR2. FGFR2 contains an extracellular domain (with three IgG-like domains), a transmembrane domain (TM), and two intracellular tyrosine kinase domains. The IIIb isoform is found in epithelial cells while the IIIc isoform in mesenchymal cells. Exons IIIb and IIIc are regulated coordinately to provide mutually exclusive expression of the two isoforms and transcripts including both exons are destabilized by nonsense-mediated decay. We have previously used FGFR2 alternative splicing reporters, in particular constructs that measure the epithelial-specific silencing of exon IIIc (e.g., pRIIIcl$^2$ in FIG. 1B), to report on the phenotypic state of cells in vitro and in vivo. In FIG. 1B is a schematic of the pRIIIcl$^2$ minigene and the fluorescence read-out. The minigene contains the DsRED open reading frame interrupted by exon IIIc and flanking introns of the FGFR2 gene. In epithelial cells exon IIIc is skipped, DsRED open reading frame is formed and results in fluorescence signal. In mesenchymal cells, exon IIIc is included and the DsRED open reading frame is disrupted, resulting in low or close-to-background fluorescence signal. The pRIIIcl$^2$ splicing reporter, which produces a variant red fluorescence protein (DsRED) when exon IIIc is silenced, revealed MET in primary tumors derived from AT3 cells implanted in the flanks of Copenhagen white rats. While most tumors contained MET foci, each tumor had very few foci and these were not randomly distributed but rather were associated with collagenous stroma. In contrast to the low frequency of MET in primary tumors, a high incidence of MET among lung metastases in these animals was observed, suggesting an unexpected association between the more epithelial phenotype and aggressive behavior. These studies could not ascertain whether the epithelial-like AT3 cells found in the lungs had undergone MET in the primary tumors or during the process of metastasis.

In an attempt to find post-MET cells in vitro, limiting dilution was used to obtain clones from AT3 cells stably transfected with the pRIIIcl$^2$ reporter. A total of 16 clones of a maximum calculated recovery of 27 were obtained, which is ~60% cloning efficiency. Eleven of these sixteen clones expressed RIIIcl$^2$ transcripts (italicized in Table 2), and of these, eight expressed DsRED (Table 2). Some of the clones had an epithelial-like morphology (cells with cobblestone appearance and adherent to each other), while others had a mesenchymal-like morphology (spindle-shaped), as well as clones that displayed a mixed phenotype. It is important to note that given the high cloning efficiency and the high frequency of DsRED+ clones, it is highly unlikely for these epithelial-like clones to come from a very small population within the parental AT3 cells. Rather, the process of subcloning induced a phenotypic transition in a significant number of the AT3 cells.

TABLE 2

Properties of AT3 clones.

| AT3 Clones | Cellular morphology[3] | DsRED expression[2] | Detection of exon IIIc skipping among RIIIcl3 transcripts[1] | FGFR2 transcripts detected[3] |
|---|---|---|---|---|
| 1 | Epithelial | High | + | IIIc |
| 2 | Epithelial | High | + | IIIc > IIIb |
| 3 | Epithelial | Low | ND | IIIc > IIIb |
| 4 | Epithelial | Low | ND | IIIc |
| 5 | Epithelial | High | + | IIIc > IIIb |
| 6 | Mesenchymal | Low | ND | IIIc |
| 7 | Mixed | Low | ND | IIIc |
| 8 | Mixed | High | + | IIIc |
| 9 | Mixed | Low | ND | IIIc |
| 10 | Mixed | High | + | IIIc |
| 11 | Mesenchymal | Low | − | IIIc |
| 12 | Mesenchymal | Low | − | IIIc |
| 13 | Epithelial | High | −1 | IIIc > IIIb |
| 14 | Epithelial | Low | − | IIIc |
| 15 | Epithelial | High | + | IIIc |
| 16 | Mixed | High | −2 | IIIc |

[1]See FIG. 1C. A "+" indicates detection of RIIIcl$^2$ transcripts missing exon IIIc, a "−" all RIIIcl$^2$ transcripts include exon IIIc, ND means that no RIIIcl$^2$ transcripts were detected.
[2]Determined by epifluorescence microscopy (high is defined as fluorescence above background of naive AT3 cells and low undistinguishable from the same cells).
[3]Discussed further herein and illustrated in FIG. 1C.

All of the clones obtained by limiting dilution were analyzed to determine the splicing status of RIIIcl$^2$ and endogenous FGFR2 transcripts. We could not detect exon IIIc skipping among pRIIIcl$^2$ transcripts or any evidence of exon IIIb inclusion among endogenous FGFR2 transcripts in clones with a mesenchymal-like morphology (FIG. 1C and Table 2). FIG. 1C shows RT-PCR analysis of the reporter (upper panel) and endogenous FGFR2 (lower panel). Primers used for the reporter are designed in the DsRED regions flanking exon IIIc. RT-PCR shows a higher percentage of the skipped product in clone AT3-T compared to clone AT3M. Reactions that did not include RT (−RT) reveal a contaminating product that is out-competed by the presence of a bona fide cDNA template (AT3-M lanes). Since exons IIIb and IIIc differ in size by only 3 nucleotides, analysis of the presence of IIIb or IIIc exons in FGFR2 gene was done by using primers in the flanking exons and specific restriction digestion of the resulting RT-PCR products. Exon IIIb is digested by Aval (A) and IIIc by HincII (H). There is a higher percentage of exon IIIb in clone AT3-T. The RT-PCR are replicates from three different cultures of the two clones. These clones did not express detectable levels of DsRED (FIG. 1D and Table 2). FIG. 1D shows epifluorescence and phase-contrast pictures of clones AT3-M and AT3-T shows the difference in fluorescence intensity and morphology between the two clones. Epifluorescence pictures were taken at the same exposure. All pictures were acquired at 200× magnification. While the skipping of exon IIIc among pRIIIcl$^2$ transcripts from epithelial-like clones could be expected, the observation that all of these clones both skipped and included exon IIIc was unexpected (FIG. 1C, Table 2 and data not shown). Analysis of endogenous FGFR2 transcripts revealed that four of the clones with epithelial morphology and DsRED expression had clear evidence of coexpression of both IIIb and IIIc isoforms (Table 2, and FIGS. 1C and 1D). As shown in FIG. 1, AT3-T cells expressed epithelial and mesenchymal isoforms of FGFR2. The expression of DsRED in all the cells suggested that each cell in the culture was expressing both isoforms (FIG. 1C).

We followed two clones with epithelial morphology, high DsRED levels and co-expression of FGFR2-IIIb and -IIIc transcripts (clone 2 and clone 5 (clone 5 herein AT3-T)) and noted that the phenotypic characteristics described above were stable for over six months. Equally, we followed clone 11 (clone 11 herein AT3-M) and clone 12 for six months, and noted that the mesenchymal morphology, undetectable DsRED expression and exclusive production of FGFR2-IIIc were also stable. We concluded from these observations that AT3 cells were plastic and were coaxed by sub-cloning to populate intermediate phenotypic states, with properties of epithelial and mesenchymal cells.

Figure 2:
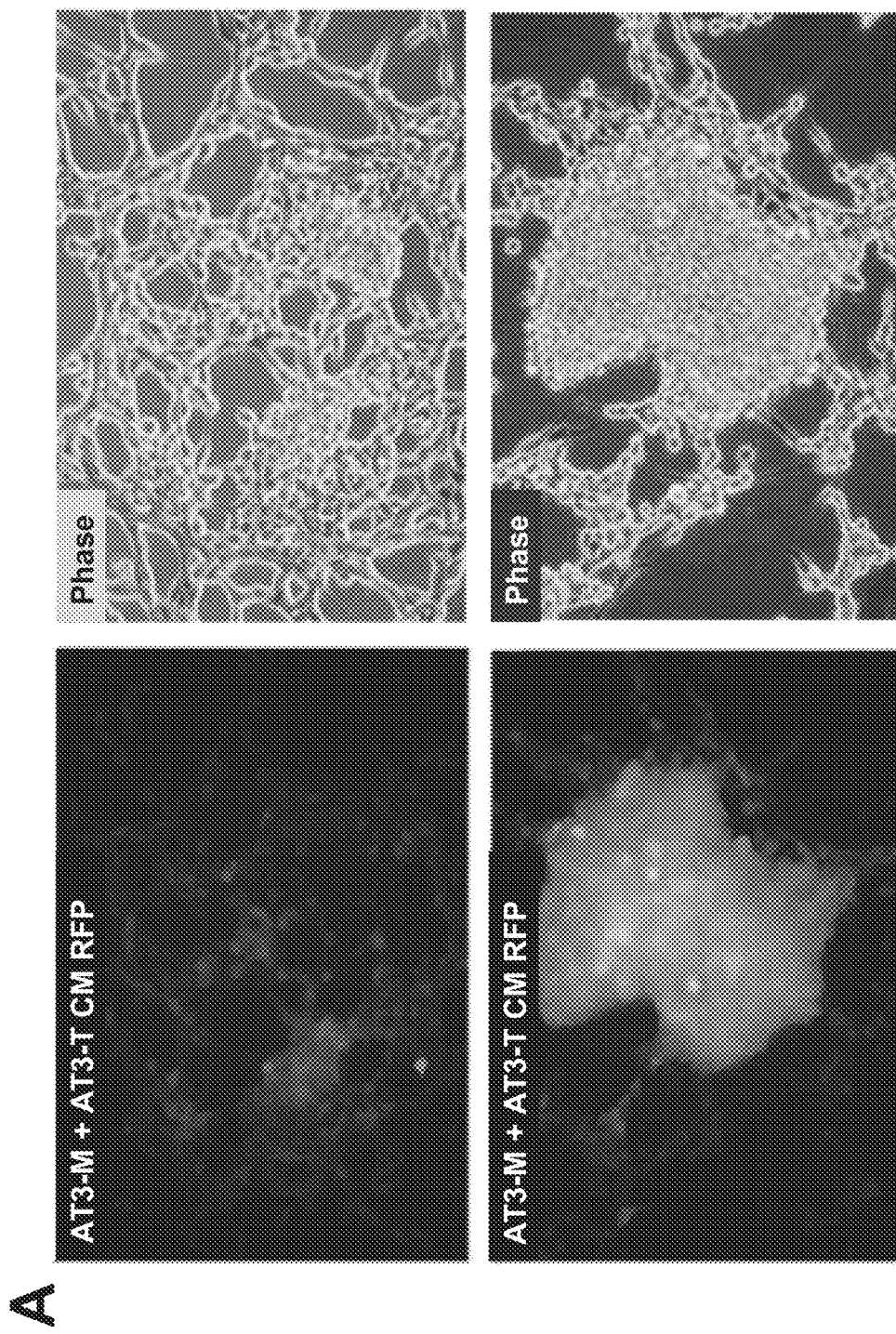
FIG. 2. (A) depicts examples of clusters of DsRED positive cells formed by AT3-M cells upon treatment with conditioned media from clone AT3-T. (B) depicts flow cytometry analysis of the same experiment.

A media exchange experiment was used to investigate whether or not the splicing of RIIIcI$^2$ transcripts in the DsRED expressing clones was regulated by soluble factors. Media conditioned by DsRED expressing clones (clone 5 in Table 2) was filtered and added to DsRED negative clones (clone 11 in Table 2). DsRED+ cells were observed among DsRED-cells incubated with DsRED+ conditioned media (FIG. 2). FIG. 2A shows examples of clusters of DsRED positive cells formed by AT3-M cells upon treatment with conditioned media from clone AT3-T. Media was conditioned for 24 h, filtered and added on AT3-M cells. Pictures (acquired at 200×) are taken 48 h following media exchange. FIG. 2B shows results from flow cytometry analysis of the same experiment. Left upper panel represents clone AT3-M conditioned with media from the same clone, as a negative control. Right upper panel represents clone AT3-T, which is DsRED positive. The lower panel represents clone AT3-M 48 h after conditioned media from clone AT3-T was added. Different lots of fetal bovine serum caused variation in this effect. This effect was quantified by flow cytometry and these data suggested that about half of the DsRED− cells were induced to express DsRED at levels equivalent to those seen in DsRED+ cells (FIG. 2). The changes observed were not due to prolonged culture of the cells in the same wells because conditioned media from a separate DsRED− culture did not induce DsRED expression. As shown in FIG. 2, AT3-T conditioned media induced AT3-M cells to express DsRED. These observations suggest that soluble factors secreted by the DsRED+ clones or dilution of factors extant in the DsRED− conditioned media may contribute to plasticity.

Example 3. AT3-M and AT3-T Cells are Tumorogenic

The initial characterization of the AT3-T revealed that these transitional cells grew slower and reached a lower confluent density than the AT3-M (FIG. 3A). FIG. 3A shows growth curves for clones AT3-T and AT3-M. Cells were plated at 0 h time-point, trypsinized, and counted at the indicated times. Data are the mean±S.D. (n=3). To investigate their growth in vivo AT3-M and AT3-T cells were co-transfected with pGint a plasmid that expresses EGFP (herein GFP) in both mesenchymal and epithelial cells, and sorted stable populations of each cell line using flow cytometry for uniform GFP intensity. The GFP expressing cells maintained the morphological characteristics, the differential DsRED expression, and the differences in the splicing of pRIIIcI$^2$ and FGFR2 transcripts first observed after sub-cloning.

Figure 3:
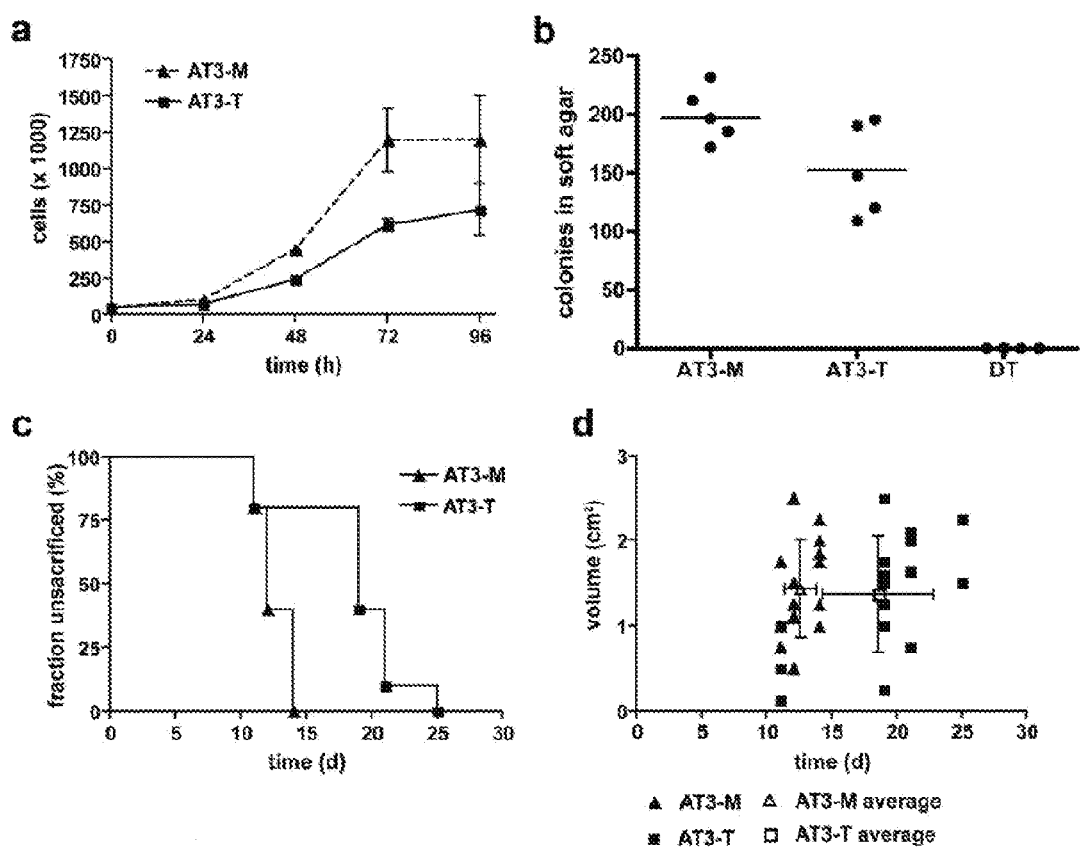
FIG. 3. (A) depicts growth curves for clones AT3-T and AT3-M. (B) is graph of growth of AT3-M, AT3-T, and DT cells in soft agar. (C) depicts a sacrifice curve for rats injected with AT3-M or AT3-T cells. (D) depicts a comparison of tumor volumes resulting from AT3-T and AT3-M injection.

We injected 3×10$^5$ GFP-expressing AT3-T or AT3-M cells subcutis in both flanks of Copenhagen white 2331 male rats. All of the animals developed bilateral tumors, indicating that both AT3-M and AT3-T cells were highly tumorogenic in these syngeneic rats. As a humane endpoint, rats were sacrificed when tumor length estimated by palpation reached 1 cm. The in vivo growth curves for the AT3-M and AT3-T tumors were significantly different, as determined by a logrank test (p=0.0020; FIG. 3B). FIG. 3B is a sacrifice curve for rats injected with AT3-M or AT3-T cells. FIG. 3C shows comparison of tumor volumes resulting from AT3-T and AT3-M injection. The Y-axis represents tumor volumes at the time of sacrifice of the animals and the X-axis days from the time of implantation to the time of sacrifice. Average tumor volumes and average days until sacrifice are represented with S.D. bars. Some points represent more than one tumor with the same volume on the same day. Tumor volume was measured (FIG. 3C) and although most AT3-T animals were sacrificed later, there was no significant difference in tumor size (p=0.76). As shown in FIG. 3, AT3-T cells grew more slowly than the mesenchymal-like AT3-M cells in vitro and in vivo, but both were equally tumorogenic. We concluded that whereas AT3-T cells grew more slowly in vitro and in vivo relative to their more mesenchymal siblings, these transitional cells were capable of forming tumors.

Example 4. Both AT3-M and AT3-T are Plastic

Figure 4:
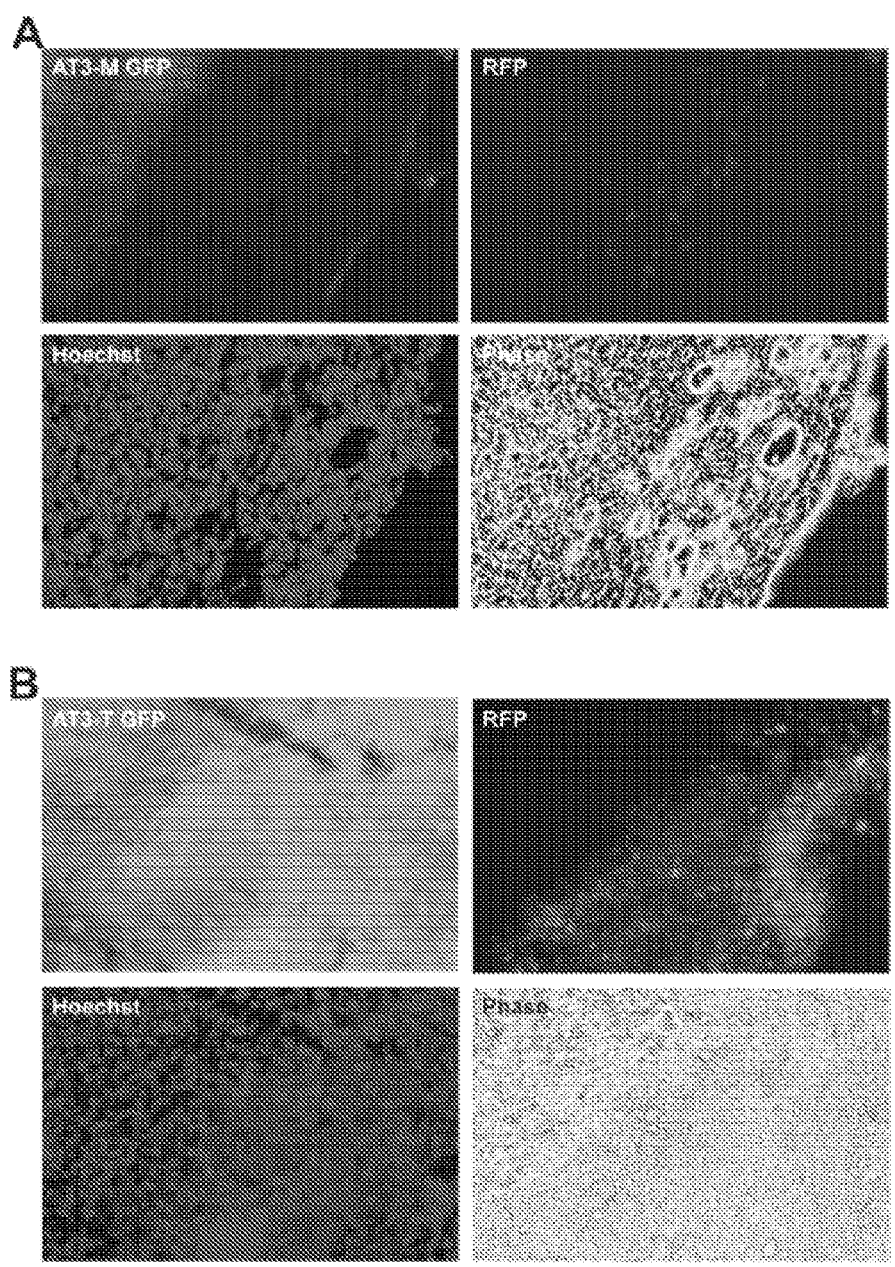
FIG. 4. (A) depicts a representative example of cells that express both RFP and GFP at the periphery of an AT3-M tumor stably transfected with Gint and pRIIIcI$^2$ reporters. (B) a representative example of a section from an AT3-T tumor stably transfected with GFP and pRIIIcI$^2$ reporters.
Figure 5:
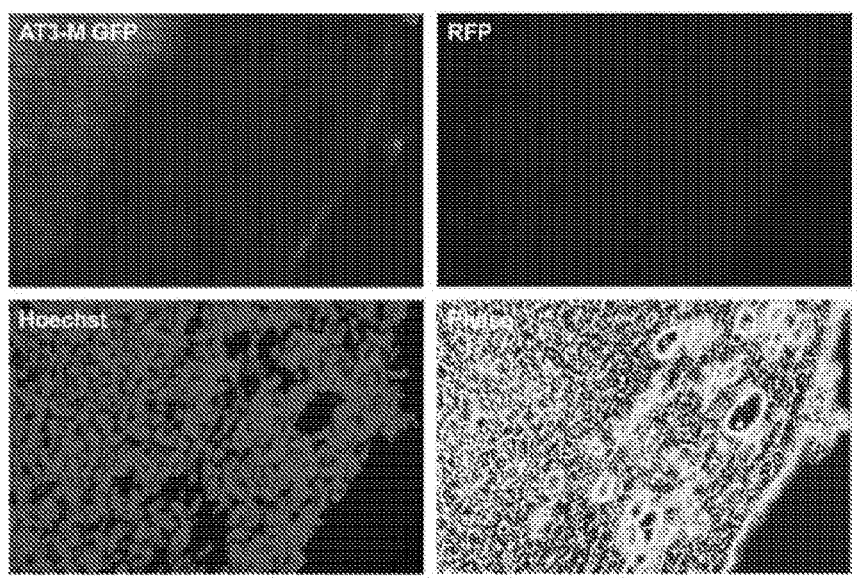
FIG. 5 depicts a representative example of cells that express both RFP and GFP at the periphery of an AT3-M tumor stably transfected with Gint and pRIIIcI$^2$ reporters.

Since the implanted AT3-M and AT3-T cells could be tracked by GFP expression, and epithelial character could be interrogated by DsRED expression, the plasticity of the tumors were able to be investigated. The overwhelming majority of cells in AT3-M tumors expressed GFP but not DsRED (FIG. 4A). As shown in FIG. 4, tumors from both AT3-T and AT3-M clones have evidence of plasticity. FIG. 4A shows representative example of cells that express both RFP and GFP at the periphery of an AT3-M tumor stably transfected with Gint and pRIIIcI$^2$ reporters. Pictures were taken at 200× magnification. To compensate for a low RFP signal, the color curve of the entire picture was adjusted. Nonetheless, groups of cells were observed expressing both GFP and DsRED in many AT3-M tumor sections, especially near the tumor capsule, (FIG. 4A; see also FIG. 5). FIG. 5 shows a representative example of cells that express both RFP and GFP at the periphery of an AT3-M tumor stably transfected with Gint and pRIIIcI$^2$ reporters. Pictures were taken at 200× magnification. In this version, overall RFP signal was not adjusted via color curve after the image was captured. RFP positive cells were clearly above background level.

Many sections from AT3-T tumors co-expressed GFP and DsRED; however, large areas were observed that expressed GFP but not DsRED in all 64 sections surveyed (FIG. 4B). FIG. 4B shows representative example of a section from an AT3-T tumor stably transfected with GFP and pRIIIcI$^2$ reporters. Pictures were taken at 200× magnification. RNA extracted from these regions of AT3-T tumors confirmed the presence of the pRIIIcI$^2$ transcripts. Both AT3-T and AT3-M cells were plastic and produced tumors with cells that displayed a range of epithelial-mesenchymal properties.

Example 5. AT3-T Cells are Motile In Vitro and Metastatic In Vivo

Figure 6:
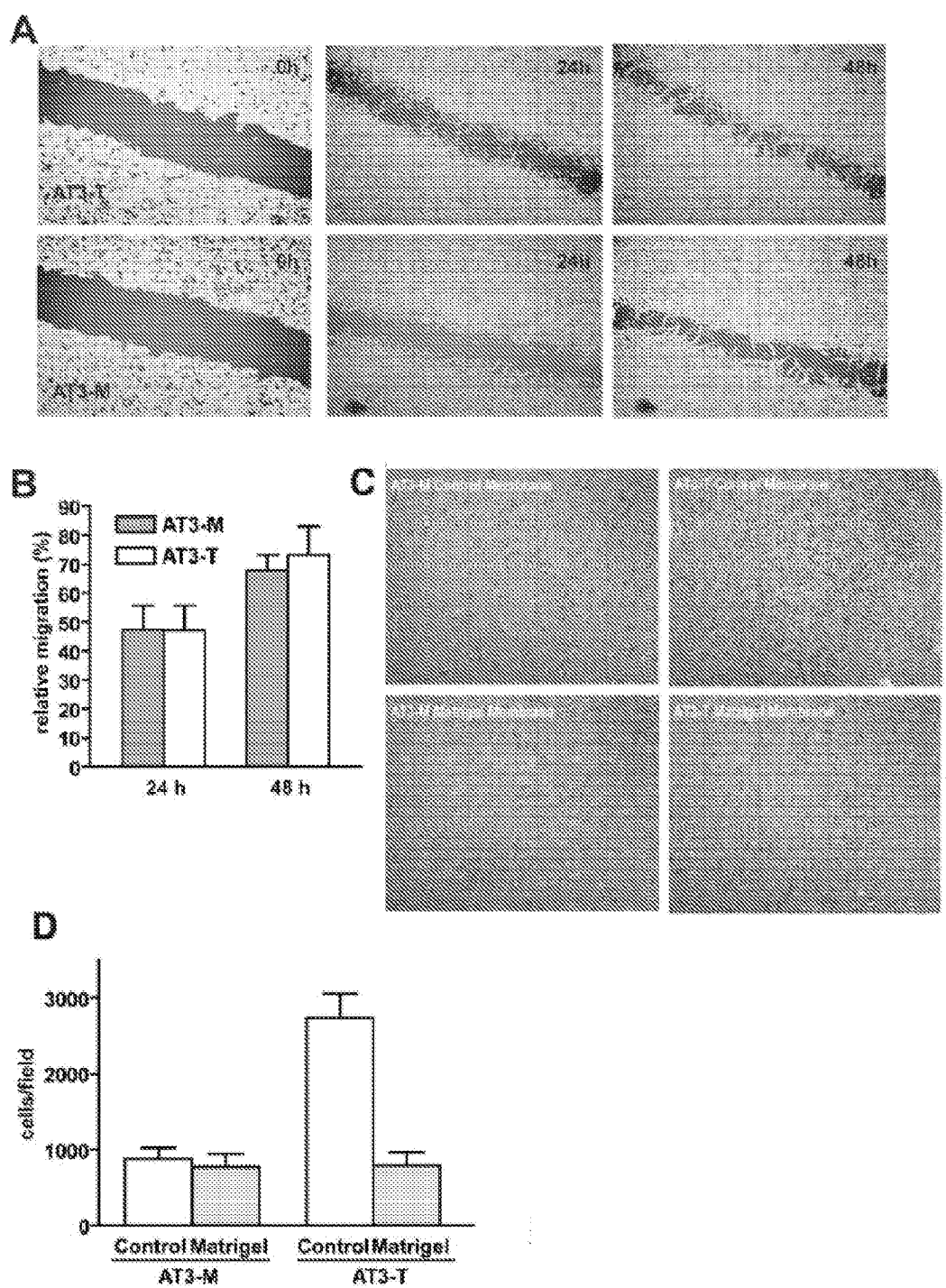
FIG. 6. (A) depicts representative pictures of cells for the scratch-wound assay. (B) a quantification of migration. (C) an invasion assay using Matrigel coated membranes. (D) a quantification of invasion assay results.

Comparison of AT3-T and AT3-M mobility and invasive potential was performed in culture. Motility was measured in culture by a "wound closure" assay, and no significant motility difference (p=0.59) was found between cell lines 24 and 48 hours after a scratch-wound had been made in the cultures (FIG. 6). FIG. 6A shows representative pictures for the scratch-wound assay (experiment done in triplicate for each clone). Pictures were taken at 40× magnification. FIG. 6B shows quantification of migration as explained in Methods. Mean and SO values were derived from triplicate experiments. FIG. 6C shows invasion assay using Matrigel coated membranes. Representative pictures of each clone and for both control membranes and Matrigel-coated membranes (n=5). Cells were stained with hematoxylin-eosin. Pictures were taken at 40× magnification. FIG. 6D shows quantification of invasion assay results. Mean and SD values were derived from five individual experiments. To gauge invasive properties of the cells we measured the number of cells traversing through Matrigel membranes in a 22-hour period. The same number of AT3-T and AT3M cells was observed on the Matrigel membranes suggesting that the two cell lines were equally capable of invading this membrane (FIG. 6). While a higher number of cells from clone AT3-T were observed on the control membrane compared to clone AT3-M, these studies nevertheless indicated that the more epithelial AT3-T cells had similar motility and invasive potential as the AT3-M cells. As shown in FIG. 6, AT3-M and AT3-T cells exhibited similar migration in vitro.

Figure 7:
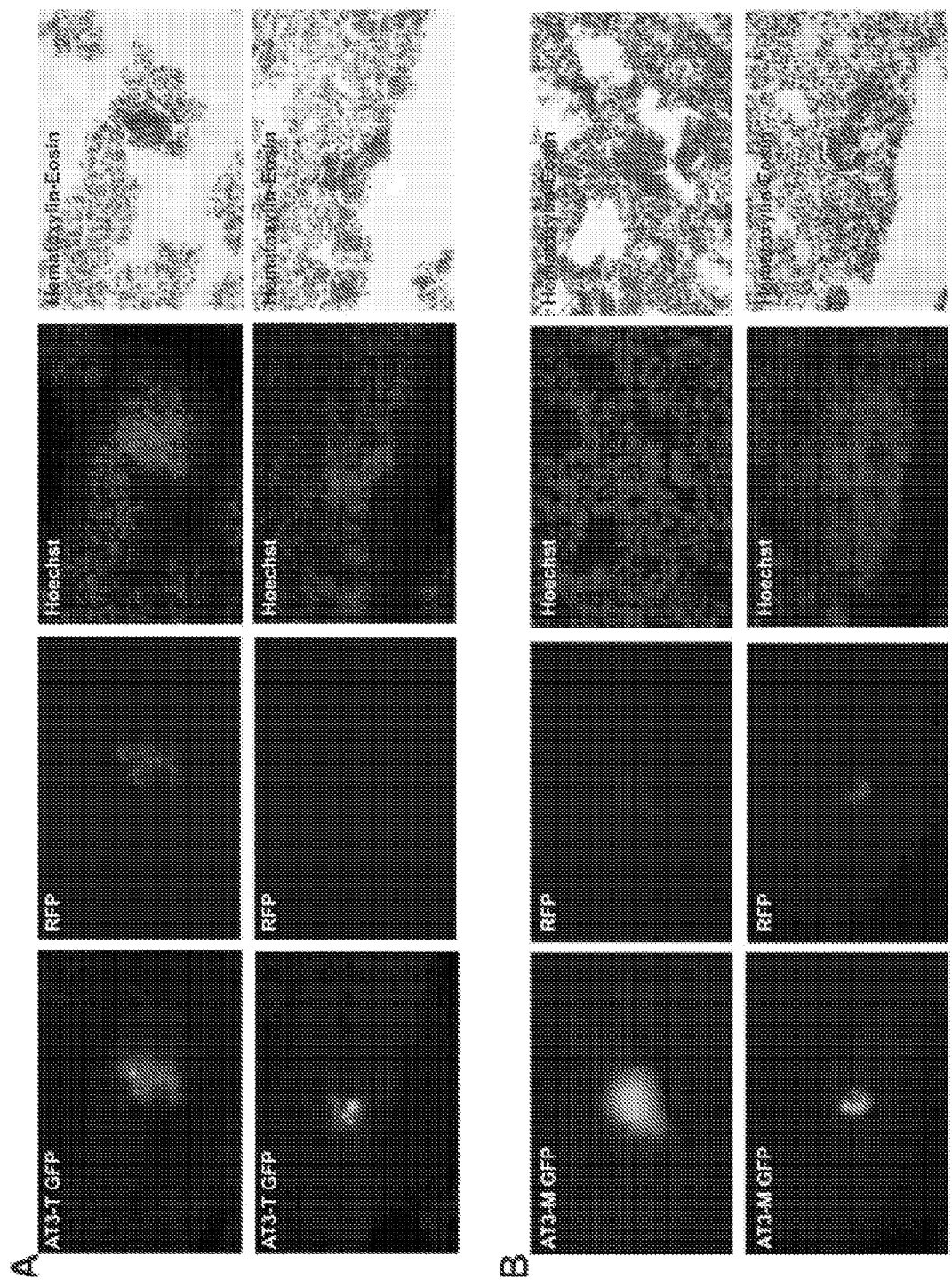
FIG. 7 are metastatic foci in lungs from animals with tumors from either AT3-T or AT3-M clones (stably transfected with GFP and pRIIIcI$^2$ reporters). (A) (upper panel) is an example of a section exhibiting the pattern for clone AT3-T (i.e. GFP+, DsRED+) in a metastatic focus and (lower panel) an example of a section exhibiting a plastic pattern for clone AT3-T (i.e. GFP+, DsRED−) in a metastatic focus. (B) (upper panel) is an example of a section exhibiting the pattern for clone AT3-M (i.e. GFP+, DsRED−) in a metastatic focus and (lower panel) an example of a section exhibiting a plastic pattern for clone AT3-M (i.e. GFP+, DsRED+) in a metastatic focus.

In order to assess invasiveness in vivo lungs from the twenty animals harboring AT3-M and AT3-T tumors were examined for presence of metastatic foci. No macroscopic metastatic nodules were observed in any of the lungs, which was likely due to the sacrificing protocol used on the animals when the tumors reached a specified size instead of using survival as the end-point. The GFP expression from the Gint reporter was examined to evaluate the presence of micrometastases by epifluorescence microscopy. To assure a comprehensive evaluation, 7-8 equally spaced sections from each lung were surveyed (total of 150 sections for each clone). The presence of metastatic foci was determined by GFP fluorescence, followed by counter-staining of the sections with hematoxylineosin (FIG. 7). FIG. 7A shows (upper panel) an example of a section exhibiting the expected pattern for clone AT3-T (i.e. GFP+, DsRED+) in a metastatic focus, and (lower panel) an example of a section exhibiting a plastic pattern for clone AT3-T (i.e. GFP+, DsRED−) in a metastatic focus. FIG. 7B shows (upper panel) an example of a section exhibiting the expected pattern for clone AT3-M (i.e. GFP+, DsRED−) in a metastatic focus, and (lower panel) an example of a section exhibiting a plastic pattern for clone AT3-M (i.e. GFP+, DsRED+) in a metastatic focus. As shown in FIG. 7, metastatic foci in lungs from animals with tumors from either AT3T or AT3-M clones (stably transfected with GFP and pRIIIcI$^2$ reporters) had evidence of plasticity. Metastatic foci were found in 7 out of 10 lungs for clone AT3-M and 6 out of 10 lungs for clone AT3-T.

Evaluation of the plasticity of the metastatic foci using the combined output of the GFP and DsRED reporters revealed plastic foci (DsRED+ for AT3-M and DsRED− for AT3-T) in the case of both clones: 3 out of 12 for clone AT3-T and 13 out 16 for clone AT3-M (FIG. 7). These studies indicated phenotypic plasticity for the AT3-M cells and suggested it for the AT3-T cells. Importantly, both cell lines were metastatic despite differences in the original epithelial vs. mesenchymal phenotype.

Plasticity and Metastatic Behavior of Cancer Cells.

Both the mesenchymal AT3-M and the more epithelial AT3-T cells metastasized efficiently. The drivers of metastasis, however, may be different in these two cells. The gene expression comparison between the AT3-M and AT3-T clones revealed at least one intriguing possibility: microarray analysis showed a 12-fold increase in the expression of junctional adhesion molecule C (JAM-C) in AT3-T compared to AT3-M, and this was confirmed by RT-PCR and immunoblot analysis. JAMs were present in leukocytes and at the tight junctions of epithelial and endothelial cells and have been shown to be involved in transendothelial migration of monocytes. JAM-C is expressed in several cell lines with high metastatic potential and knock-down of this molecule in the HT1080 human fibrosarcoma line significantly decreases its metastatic properties in vivo. Moreover, JAM-C is also present in the gene sets associated with stemness that had significant overlaps with genes that define clone AT3-T. Therefore clone AT3-T, by over-expression of different adhesion molecules may acquire metastatic capabilities. In addition, the overexpression of the downstream Hedgehog pathway effector GLI3 may be significantly upregulated in the more epithelial and stem cell-like AT3-T cells as compared to the more mesenchymal AT3-M cells. Hedgehog signaling has been linked to EMT, stemness, and metastasis/aggressiveness in several tumor types, and thus differential expression or regulation of developmental programs may underly these phenotypical differences across these cell lines. Increased expression of Patched, a Hedgehog pathway component, has been linked to prostate tumors during progression to androgen independence and in circulating tumor cells of men with metastatic castration-resistant prostate cancer.

Example 6. AT3-T Cells Display a Stem Cell-Like Gene Expression Signature

Figure 8A:
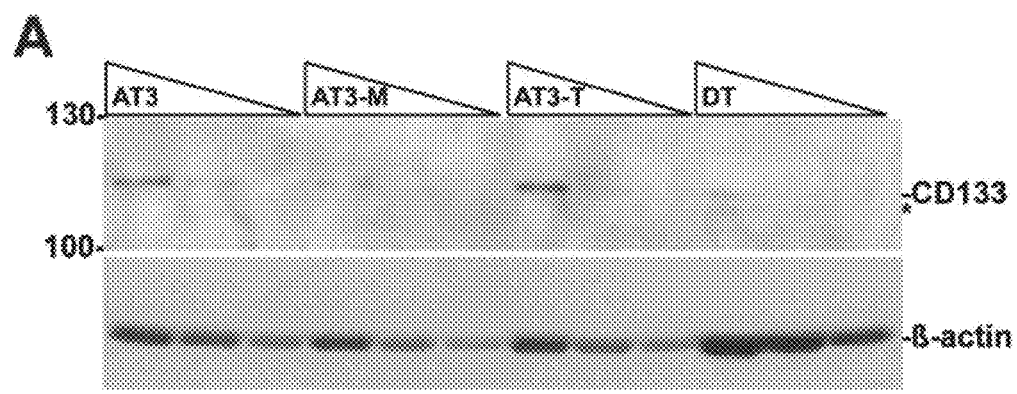
FIG. 8A depicts a membrane with serial two-fold dilutions of whole cell lysates cut in half and immunoblotted for CD133 (upper panel) or β-actin (lower panel).
Figure 8B:
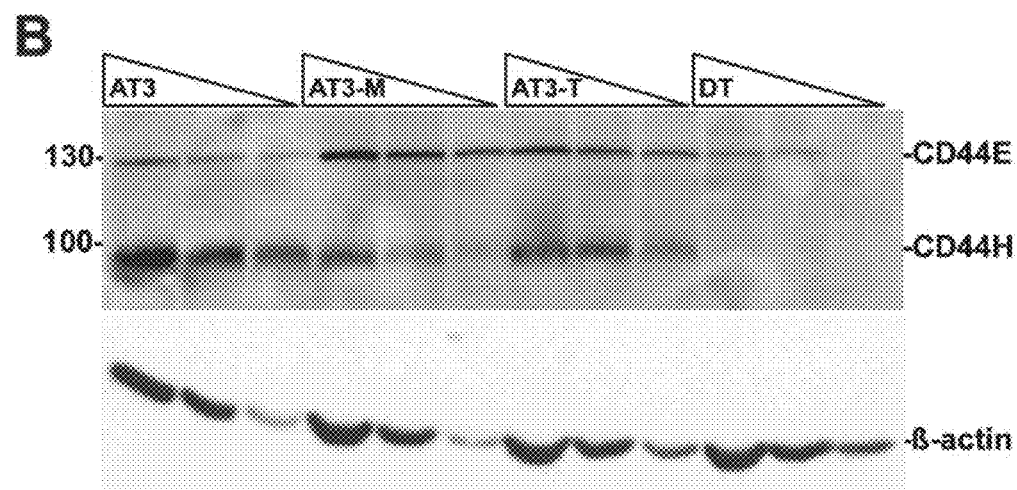
FIG. 8B depicts a membrane with serial twofold dilutions of whole cell lysates cut in half and immunoblotted for CD44 (upper panel) or β-actin (lower panel).

AT3-T cells sometimes formed tight clusters resembling protospheres. While sphere formation is not an exclusive property of stem cells, it has been associated with stemness in many different systems. Given these observations and the high tumorogenicity of AT3-T and AT3-M cells, they were tested for the expression of markers associated with cancer stem-like cells. Also included were the parental AT3 cells and another Dunning tumor cell line, DT cells, which display epithelial markers and are only weakly tumorogenic in Copenhagen white rats. The DT cells expressed very low levels of CD44 and CD133, which are associated with highly malignant cancer stem-like cells (FIG. 8A and FIG. 8B). CD133 was detectable in DT lysates only when four fold more lysate was loaded. The mesenchymal-like AT3 cells expressed much higher levels of both CD44 and CD133 than the DT cells (note that the lanes for the DT samples are overloaded in FIG. 8A), which is consistent with recent reports that EMT induces stemness in mammary epithelial carcinoma cells. FIG. 8A shows a membrane with serial twofold dilutions of whole cell lysates was cut in half and immunoblotted for CD133 (upper panel) or β-actin (lower panel). Size markers are in kDa. A faster migrating CD133 band repeatably detected only in DT lysates is marked (*), suggesting possible post-translational regulation. FIG. 8B shows a membrane with serial twofold dilutions of whole cell lysates was cut in half and immunoblotted for CD44 (upper panel) or β-actin (lower panel). Representative blots from two independent sets of lysates are shown. AT3-T expressed CD44 and CD133. Interestingly, the AT3-T cells expressed overall higher levels of CD44 and CD133 than the more mesenchymal AT3-M. Moreover, AT3-T cells expressed a higher ratio of CD44H to CD44E when compared to AT3-M cells. The CD44H isoform has been associated with malignancy while CD44E is not. This suggests a more complex relationship between epithelial transitions and acquisition of stem cell-like properties. Consistent with expression of stem-like markers, both AT3-M and AT3-T cells formed colonies in soft agar and tumors when injected into Copenhagen white rats, and these tumors led to extensive metastases similar to parental AT3 cells (FIG. 8B).

To further explore these connections between transitions and stemness, global gene expression in AT3-M and AT3-T cells was compared. This analysis showed that 422 genes were differentially expressed (≥2-fold; p-value<0.05) in these two cells (Table 3). Many of the genes that were upregulated in AT3-T relative to AT3-M were preferentially expressed in epithelial cells and vice versa for those preferentially expressed in mesenchymal cells (Table 4). There were exceptions to this, however. Expression of the gene disintegrin-like and metalloprotease was consistent with a mesenchymal phenotype, but this mRNA level was 4-fold higher in AT3-T compared to AT3-M. Integrin β-4, normally associated with epithelial-like cells, was expressed 3-fold lower in AT3-T compared to AT3-M. These observations were consistent with the characterization of AT3-T cells as displaying more epithelial features than AT3-M cells and as populating an intermediate phenotypic state.

TABLE 3

| x Fold change (AT3-T/AT3-M) | Gene Symbol (Human) | Gene Symbol (Rat) |
|---|---|---|
| 0.00771 | P2RX5 | P2rx5 |
| 0.011 | CCNB1IP1 | #N/A |
| 0.0296 | STRA6 | Stra6 |
| 0.0327 | G0S2 | G0s2 |
| 0.0835 | SERPINF1 | Serpinf1 |
| 0.101 | GSTA1 | #N/A |
| 0.107 | RSNL2 | Clip4 |
| 0.115 | ADAMTS7 | #N/A |
| 0.134 | GZMB | #N/A |
| 0.137 | SPON2 | #N/A |
| 0.156 | MMP3 | #N/A |
| 0.191 | ATP8A1 | #N/A |
| 0.197 | EVPL | Evpl |
| 0.21 | LGALS3BP | Lgals3bp |
| 0.216 | SERPINB2 | Serpinb2 |
| 0.219 | NETO2 | Neto2 |
| 0.223 | PTX3 | #N/A |
| 0.23 | SERPINB7 | Serpinb7 |
| 0.233 | RASIP1 | #N/A |
| 0.235 | OMD | #N/A |
| 0.239 | HLA-G | #N/A |
| 0.239 | HLA-A | #N/A |
| 0.247 | CD97 | Cd97 |
| 0.251 | GJA4 | Gja4 |
| 0.254 | DSU | #N/A |
| 0.257 | MGLL | Mgll |
| 0.261 | SPHK1 | #N/A |
| 0.268 | HRBL | Zcwpw1 |
| 0.268 | ZCWPW1 | Zcwpw1 |
| 0.27 | ENPP3 | Enpp3 |
| 0.275 | PTGS1 | Ptgs1 |
| 0.278 | RAMP1 | Ramp1 |
| 0.281 | DHRS3 | Dhrs3 |
| 0.282 | FAM117A | Fam117a |
| 0.284 | TUBB2A///TUBB2B | Tubb2b |
| 0.284 | TUBB2B | Tubb2b |
| 0.285 | C10orf10 | LOC500300 |
| 0.289 | SYTL2 | #N/A |
| 0.291 | SLC39A4 | Slc39a4 |
| 0.292 | CHRD | Chrd |
| 0.292 | GIP | Gip |
| 0.293 | CKLF | Cklf |
| 0.294 | PLAU | Plau |
| 0.295 | GUF1 | #N/A |
| 0.307 | CGI-38 | Tppp3 |
| 0.311 | LECT2 | Lect2 |
| 0.318 | NQO2 | #N/A |
| 0.32 | C11orf75 | RGD1309410 |
| 0.324 | DOCK2 | #N/A |
| 0.325 | LGALS2 | #N/A |
| 0.326 | CASP4 | Casp1 |
| 0.326 | LTBP4 | Ltbp4 |
| 0.334 | HSPB1 | Hspb1 |
| 0.335 | ITGB4 | Itgb4 |
| 0.34 | BPHL | Bphl |
| 0.341 | FOXF2 | #N/A |
| 0.345 | MYH1 | #N/A |
| 0.345 | SMAD6 | Smad6 |
| 0.348 | TGFB1 | Tgfb1 |
| 0.351 | MMP10 | #N/A |
| 0.363 | MMP9 | Mmp9 |
| 0.363 | COL18A1 | Col18a1 |

TABLE 3-continued

| x Fold change (AT3-T/AT3-M) | Gene Symbol (Human) | Gene Symbol (Rat) |
|---|---|---|
| 0.366 | HES1 | #N/A |
| 0.369 | SLC35D2 | #N/A |
| 0.377 | ADORA2B | Adora2b |
| 0.377 | COL3A1 | Col3a1 |
| 0.379 | DPEP2 | Dpep2 |
| 0.382 | GPR153 | Gpr153__predicted |
| 0.383 | LOC55908 | #N/A |
| 0.389 | SELPLG | #N/A |
| 0.394 | P2RX1 | Atp2a3 |
| 0.394 | ATP2A3 | Atp2a3 |
| 0.394 | ADD3 | Add3 |
| 0.395 | TSPAN9 | Tspan9 |
| 0.399 | LOC54103 | #N/A |
| 0.4 | BFSP2 | #N/A |
| 0.4 | FLJ14213 | RGD1309969 |
| 0.4 | PGGT1B | Pggt1b |
| 0.401 | HCN2 | Hcn2 |
| 0.403 | C2orf33 | RGD1310230 |
| 0.404 | TMEPAI | #N/A |
| 0.405 | INHA | Inha |
| 0.406 | HPSE | #N/A |
| 0.409 | CRY1 | Cry1 |
| 0.413 | IL3RA | Il3ra |
| 0.413 | CDC42EP1 | #N/A |
| 0.416 | ARG1 | Arg1 |
| 0.417 | MAPK14 | Mapk14 |
| 0.419 | FLJ22028 | #N/A |
| 0.421 | GALR2 | Galr2 |
| 0.422 | TSPAN8 | Tspan8 |
| 0.422 | FAM77C | RGD1561205 |
| 0.422 | USP2 | Usp2 |
| 0.422 | LAMA3 | #N/A |
| 0.424 | CCNE1 | Ccne1 |
| 0.424 | NSF | Nsf |
| 0.428 | ST3GAL5 | St3gal5 |
| 0.429 | SYNJ2 | Synj2 |
| 0.43 | ADA | Ada |
| 0.43 | PCBP3 | Pcbp3 |
| 0.433 | ZNF43 | #N/A |
| 0.433 | C14orf130 | Ubr7 |
| 0.436 | SOS2 | #N/A |
| 0.436 | RASSF3 | #N/A |
| 0.436 | GLMN | Glmn |
| 0.438 | OSR2 | Osr2 |
| 0.44 | AGTPBP1 | Agtpbp1 |
| 0.444 | DBNDD2 | RGD1311642 |
| 0.445 | SGCB | #N/A |
| 0.446 | HBLD2 | Isca1 |
| 0.446 | SCARB1 | Scarb1 |
| 0.448 | EVI2A | Evi2a |
| 0.448 | AP4M1 | #N/A |
| 0.451 | IGF2BP3 | #N/A |
| 0.452 | FLJ10404 | Ddx41 |
| 0.454 | TGFB2 | Tgfb2 |
| 0.459 | PASK | Pask |
| 0.461 | C19orf37 | Zfp428 |
| 0.462 | BMP1 | Bmp1 |
| 0.464 | PTPN13 | Ptpn13 |
| 0.47 | PTPRG | #N/A |
| 0.47 | EFNB1 | Efnb1 |
| 0.472 | PER2 | Per2 |
| 0.472 | IRS3L /// LOC442715 | Irs3 |
| 0.472 | HRBL | Irs3 |
| 0.472 | MAP3K3 | Kcnh6 |
| 0.472 | WDR68 | Kcnh6 |
| 0.472 | KCNH6 | Kcnh6 |
| 0.472 | CCDC44 | Kcnh6 |
| 0.473 | CIB2 | Cib2 |
| 0.475 | MPZL1 | Mpzl1 |
| 0.475 | FADS2 | #N/A |
| 0.48 | ZNF185 | #N/A |
| 0.482 | SLC29A1 | Slc29a1 |
| 0.487 | RUNX3 | Runx3 |
| 0.488 | NINJ1 | Ninj1 |
| 0.489 | RASL11B | Rasl11b |
| 0.49 | ECE2 | Ece2 |
| 0.49 | TNNC2 | Tnnc2 |

TABLE 3-continued

| x Fold change (AT3-T/AT3-M) | Gene Symbol (Human) | Gene Symbol (Rat) |
|---|---|---|
| 0.491 | WASPIP | Wipf1 |
| 0.492 | FN1 | Fn1 |
| 0.494 | NDE1 | Nde1 |
| 0.494 | CAMK2G | Camk2g |
| 0.495 | CUTL1 | Cux1 |
| 0.495 | ABHD6 | Abhd6 |
| 0.495 | PTPN14 | Ptpn14 |
| 0.497 | FLJ13946 | #N/A |
| 0.498 | BAIAP2 | Baiap2 |
| 0.499 | MSL3L1 | Msl3l1 |
| 0.499 | DYNLT1 | Dynlt1 |
| 0.499 | GSTM3 | Gstm5 |
| 2 | CHES1 | Foxn3 |
| 2.004 | AQR | Aqr /// Znf770 |
| 2.006 | EPN1 | Epn1 |
| 2.011 | PPBP | Ppbp |
| 2.019 | SLC35D1 | #N/A |
| 2.022 | PTPRC | #N/A |
| 2.031 | USP47 | Usp47 |
| 2.041 | DHX29 | #N/A |
| 2.047 | HMOX1 | #N/A |
| 2.05 | CAV1 | Cav1 |
| 2.053 | BUB1B | Bub1b |
| 2.069 | KCNIP4 | #N/A |
| 2.072 | — | #N/A |
| 2.072 | ADAM10 | #N/A |
| 2.073 | KIAA1155 | #N/A |
| 2.074 | PSTPIP2 | #N/A |
| 2.083 | MAML1 | #N/A |
| 2.084 | RAB32 | #N/A |
| 2.089 | FAM111A | #N/A |
| 2.095 | ATRNL1 | #N/A |
| 2.101 | PPIC | Ppic |
| 2.101 | CHD4 | Chd4 |
| 2.109 | IDE | Ide |
| 2.117 | PITPNM3 | #N/A |
| 2.121 | NFE2L1 | Nfe2l1 |
| 2.121 | MFSD1 | #N/A |
| 2.133 | KITLG | Kitlg |
| 2.161 | ING3 | Ing3 |
| 2.167 | CD24 | #N/A |
| 2.169 | IDS | #N/A |
| 2.177 | MGC3196 | LOC686289 /// LOC690285 |
| 2.185 | FBXL11 | Fbxl11 |
| 2.185 | — | Fbxl11 |
| 2.191 | ZC3H12A | #N/A |
| 2.195 | RKHD2 | #N/A |
| 2.201 | LAMC2 | Lamc2 |
| 2.217 | KIF11 | Kif11 |
| 2.242 | SNAPC5 | Snapc5 |
| 2.252 | THRAP3 | #N/A |
| 2.261 | HS6ST1 | #N/A |
| 2.264 | OXCT1 | #N/A |
| 2.266 | TEK | #N/A |
| 2.268 | HIST2H4///H4/o/// LOC648164 | #N/A |
| 2.271 | TMF1 | Tmf1 |
| 2.273 | ZBTB7B | Zbtb7b |
| 2.274 | CAMSAP1L1 | RGD1310950 |
| 2.279 | CYP3A5 | Cyp3ai |
| 2.279 | CYP3A7 | Cyp3a9 |
| 2.279 | CYP3A4 | Cyp3a9 |
| 2.282 | PENK | Penk1 |
| 2.283 | KIAA2010 | Smek1 |
| 2.284 | CHRNA1 | #N/A |
| 2.299 | BAT3 | Bat3 |
| 2.302 | ROM1 | Rom1 |
| 2.306 | HOXB8 | #N/A |
| 2.309 | KLK14 | #N/A |
| 2.31 | SUV39H1 | #N/A |
| 2.315 | LOC440354///BOLA2/// LOC595101 | RGD1564579 |
| 2.315 | UBN1 | Ubn1 |
| 2.323 | C1orf103 | #N/A |
| 2.333 | EYA2 | Eya2 |
| 2.347 | MT2A | #N/A |
| 2.353 | KIAA1815 | Ermp1 |
| 2.355 | SETD1B | #N/A |
| 2.369 | MPHOSPH1 | Kif20b |
| 2.38 | EFNA1 | Efna1 |
| 2.392 | ABCF2 | Abcf2 |
| 2.397 | LIMA1 | Lima1 |
| 2.418 | EXTL3 | Extl3 |
| 2.418 | ARL6IP2 | Arl6ip2 |
| 2.442 | GRAMD3 | Gramd3 |
| 2.456 | JARID1A | Jarid1a |
| 2.476 | ARHGEF9 | Arhgef9 |
| 2.485 | CAD | Cad |
| 2.493 | RAI17 | #N/A |
| 2.526 | KIAA0284 | #N/A |
| 2.529 | SGPP1 | Sgpp1 |
| 2.531 | ABCB1 | #N/A |
| 2.531 | ABCB1///ABCB4 | #N/A |
| 2.542 | KIF1C | #N/A |
| 2.553 | KIAA0020 | LOC499339 |
| 2.563 | ADAM15 | Adam15 |
| 2.577 | UBE1 | Uba1 |
| 2.577 | INE1 | Uba1 |
| 2.58 | GRIP2 | Grip2 |
| 2.59 | PPEF1 | #N/A |
| 2.619 | SC65 | Sc65 |
| 2.62 | FER1L3 | #N/A |
| 2.62 | NOC3L | #N/A |
| 2.62 | RBP4 | #N/A |
| 2.645 | SPINK4 | Spink4 |
| 2.653 | ATXN2L | #N/A |
| 2.711 | AHCYL1 | Ahcyl1 |
| 2.723 | TUBB3 | Tubb3 |
| 2.723 | MC1R | Tubb3 |
| 2.729 | AGPAT7 | Lpcat4 |
| 2.749 | HOXC11 | #N/A |
| 2.766 | APH1A | Aph1a |
| 2.785 | CNOT1 | RGD1308009 |
| 2.785 | CSNK2A2 | RGD1308009 |
| 2.794 | STAC | #N/A |
| 2.904 | STAG1 | #N/A |
| 2.942 | MBNL1 | #N/A |
| 2.982 | MNT | Mnt |
| 3.007 | RANBP5 | Ipo5 |
| 3.014 | HERC1 | Herc1 |
| 3.065 | ALDOC | Aldoc |
| 3.122 | KIAA0460 | — |
| 3.174 | FLT3 | #N/A |
| 3.278 | CXCL6 | Cxcl6 |
| 3.366 | GLI3 | #N/A |
| 3.489 | SSR3 | #N/A |
| 3.585 | BCAN | Bcan |
| 3.824 | FKBP10 | Fkbp10 |
| 3.903 | GSTK1 | Gstk1 |
| 3.931 | PSCDBP | #N/A |
| 3.974 | ALCAM | Alcam |
| 4.056 | ADAMTS13 | |
| 4.203 | SPRR2B | #N/A |
| 4.276 | GPR126 | #N/A |
| 5.169 | SULF1 | Sulf1 |
| 5.529 | TFF1 | Tff1 |
| 6.52 | PTN | Ptn |
| 8.591 | MLF1 | Mlf1 |
| 9.012 | THBS2 | Thbs2 |
| 10.79 | HEPH | Heph |
| 12.53 | JAM3 | Jam3 |

TABLE 4

Examples of epithelial or mesenchymal genes in the expression data analysis of clones AT3-T and AT3-M.

| Gene name | x Fold change in AT3-T vs. AT3-M |
|---|---|
| Junctional adhesion molecule C | 12.53 |
| Disintegrin-like and metalloprotease | 4.05 |
| Activated leukocyte cell adhesion molecule | 3.97 |
| Tubulin | 2.73 |
| Epithelial protein lost in neoplasm | 2.39 |
| Laminin | 2.20 |
| TGFβ2 | 0.45 |
| MMP9 | 0.36 |
| Collagen, type XVIII | 0.36 |
| MMP10 | 0.35 |
| Integrin β4 | 0.33 |
| TGFβ1 | 0.31 |
| Urokinase plasminogen activator | 0.29 |
| MMP3 | 0.15 |

Two gene sets were assembled: one composed of gene products upregulated in AT3-T (relative to AT3-M) and the second of those downregulated in AT3-T (relative to AT3-M). The two gene sets were compared for overlap with 5,452 gene sets from the Molecular Signature Database collections (Gene Set Enrichment Analysis (GSEA) http://www.broad.mit.edu/gsea/). Analysis of genes over-expressed in AT3-T relative to AT3-M for overlap with 5,452 gene sets from the Molecular Signature Database collections via Gene Set Enrichment Analysis (GSEA) did not show any significant enrichment of sets associated with EMT or MET. In this regard, both AT3-M and AT3-T resembled the mesenchymal-like, parental AT3 line. Among the 15 most significant overlaps for the genes overexpressed in AT3-T there were three sets of genes activated in hematopoetic stem cells ($p=3.24 \times 10^{-8}$), neural stem cells ($p=3.07 \times 10^{-7}$) and embryonal murine stem cells ($p=5.14 \times 10^{-6}$), (Table 5) while among the 20 most significant overlaps for the genes that are relatively downregulated in AT3-T cells were two gene sets associated with development of mature cell types. Expression of the downstream hedgehog pathway effector GL13 was found to be 3.4-fold overexpressed in AT3-T cells compared to AT3-M cells, indicating that regulation of this developmental/stemness pathway in prostate cancer may be tied to the underlying phenotypic state during EMT/MET, similar to what has been reported in other tumors. These data indicated that AT3-T cells have gene expression profiles similar to stem cells, and, in concordance with the analysis of CD44 and CD133 protein expression, suggested that AT3-T cells exist in a more stem cell-like state than the more mesenchymal AT3-M cells.

TABLE 5

GSEA Collections: C1, C3, C2, C5, C4
overlaps shown: 20
gene sets in collections: 5452
genes in comparison (N) 127
genes in collections (N) 39655

| gene set name | # genes in gene set (k) | Description | # genes in overlap (k) | k/K | p value |
|---|---|---|---|---|---|
| TATAAA_V$TATA_O1 | 1333 | Genes with promoter regions [−2 kb, 2 kb] around transcription start site containing the motif TATAAA which matches annotation for TAF<br> TATA | 20 | 0.015 | 8.07E−09 |
| STEMCELL_HEMATOPOIET IC_UP | 1452 | Enriched in mouse hematopoietic stem cells, compared to differentiated brain and bone marrow cells | 20 | 0.0138 | 3.24E−08 |
| GNF2_RAP1B | 37 | Neighborhood of RAP1B | 5 | 0.1351 | 1.23E−07 |
| STEMCELL_NEURAL_UP | 1838 | Enriched in mouse neural stem cells, compared to differentiated brain and bone marrow cells | 21 | 0.0114 | 3.07E−07 |
| module 2 | 383 | Genes in Module_2 | 10 | 0.0261 | 4.34E−07 |
| CTTTGA_V$LEF1_Q2 | 1270 | Genes with promoter regions [−2 kb, 2 kb] around transcription start site containing the motif CTTTGA which matches annotation for LEF1: lymphoid enhancer-binding factor 1 | 17 | 0.0134 | 5.48E−07 |
| SIGNAL_TRANSDUCTION | 1637 | Genes annotated by the GO term GO:0007165. The cascade of processes by which a signal interacts with a receptor, causing a change in the level or activity of a second messenger or other downstream target, and ultimately effecting a change in the functioning of the cell. | 19 | 0.0116 | 9.33E−07 |
| module_385 | 28 | Genes in module 385 | 4 | 0.1429 | 1.91E06 |
| V$MYCMAX_O1 | 261 | Genes with promoter regions [−2 kb, 2 kb] around transcription start site containing the motif NNACCACGTGGTNN which matches annotation for MYC: v-myc myelocytomatosis viral oncogene homolog (avian)<br> MAX: MYC associated factor X | 8 | 0.0307 | 1.98E06 |

TABLE 5-continued

GSEA Collections: C1, C3, C2, C5, C4
overlaps shown: 20
gene sets in collections: 5452
genes in comparison (N) 127
genes in collections (N) 39655

| gene set name | # genes in gene set (k) | Description | # genes in overlap (k) | k/K | p value |
| --- | --- | --- | --- | --- | --- |
| GGGCGGR_V$SP1_Q6 | 3053 | Genes with promoter regions [−2 kb, 2 kb] around transcription start site containing the motif GGGCGGR which matches annotation for SP1: Sp1 transcription factor | 26 | 0.0085 | 2.59E−06 |
| AACTTT_UNKNOWN | 1963 | Genes with promoter regions [−2 kb, 2 kb] around transcription start site containing motif AACTTT. Motif does not match any known transcription factor | 20 | 0.0102 | 3.29E−06 |
| V$AP1_C | 281 | Genes with promoter regions [−2 kb, 2 kb] around transcription start site containing the motif NTGASTCAG which matches annotation for JUN: jun oncogene | 8 | 0.0285 | 3.38E−06 |
| MEMBRANE_PART | 1673 | Genes annotated by the GO term GO:0044425. Any constituent part of a membrane, a double layer of lipid molecules that encloses all cells, and, in eukaryotes, many organelles; may be a single or double lipid bilayer; also includes associated proteins. | 18 | 0.0108 | 5.09E−06 |
| STEMCELL_EMBRYONIC_UP | 1344 | Enriched in mouse embryonic stem cells, compared to differentiated brain and bone marrow cells | 16 | 0.0119 | 5.14E−06 |
| INTRINSIC_TO_MEMBRANE | 1350 | Genes annotated by the GO term GO:0031224. Located in a membrane such that some covalently attached portion of the gene product, for example part of a peptide sequence or some other covalently attached moiety such as a GPI anchor, spans or is embedded in one or both leaflets of the membrane. | 16 | 0.0119 | 5.43E−06 |
| CELL_SURFACE | 79 | Genes annotated by the GO term GO:0009986. The external part of the cell wall and/or plasma membrane. | 5 | 0.0633 | 5.58E−06 |
| UVC_XPCS_8HR_DN | 408 | Down-regulated at 8 hours following treatment of XPB/CS fibroblasts with 3 J/m^2 UVC | 9 | 0.0221 | 6.35E−06 |
| NOTCH_SIGNALING_PATHWAY | 12 | Genes annotated by the GO term GO:0007219. The series of molecular signals initiated by binding of an extracellular ligand to a Notch receptor on the surface of the target cell. | 3 | 0.25 | 6.86E−06 |
| LEI_MYB_REGULATED_GENES | 325 | Myb-regulated genes | 8 | 0.0246 | 9.62E−06 |
| MORF_DDB1 | 246 | Neighborhood of DDB1 | 7 | 0.0285 | 1.40E−05 |

Epithelial Plasticity and Stem Cell-Like Behavior.

Figure 9:
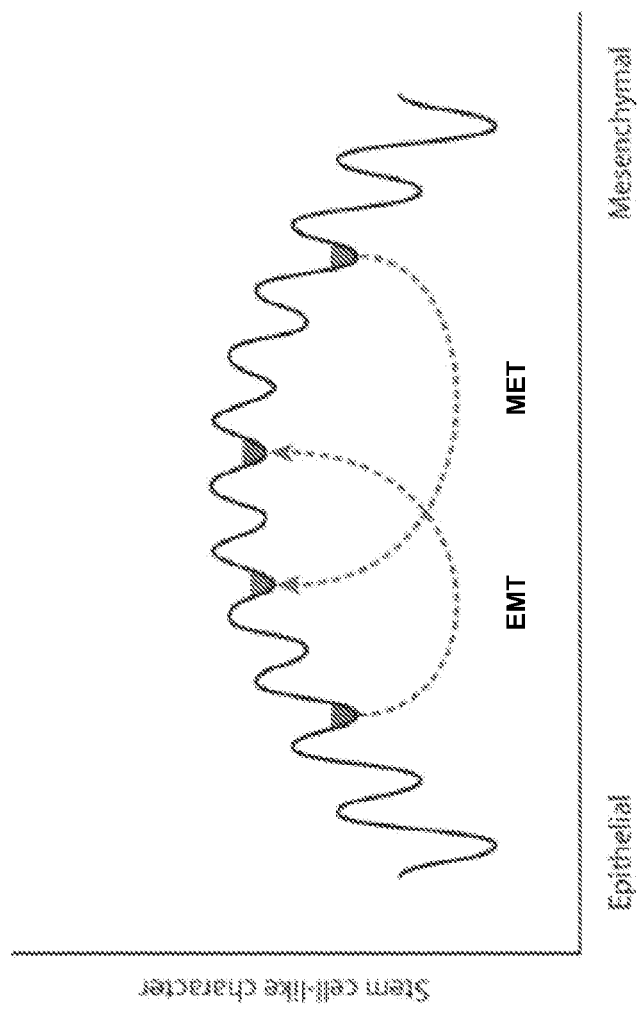
FIG. 9 depicts a model comparing stem cell-like character and epithelial mesenchymal phenotype.

It is well appreciated that cells induced to undergo EMT activate stem cell pathways. Work presented here shows that AT3 cells that transitioned towards a more epithelial state, i.e. were involved in MET, also activated expression of stem cell-like markers. This finding suggested a broader relationship between plasticity and stem cell-like character or stemness, which was modeled using a Gibbs free energy diagram (FIG. 9). FIG. 9 shows a model comparing stem cell-like character and epithelial-mesenchymal phenotype. The x-axis represents the spectrum of epithelial to mesenchymal phenotypes and the y-axis represents the stem cell-like character of the cells. The left arrow represents an EMT and the right arrow represents an MET. The model posits that as cells transition back and forth along the epithelial and mesenchymal x-axis they course through states of varying stemness, and this property peaks at intermediate states between epithelial and mesenchymal phenotypes. The number of different states and the exact height of the barriers between states are speculative and are not meant to be taken as proportional. Two phenotypic transitions are shown, the first is a partial EMT (left arrow) and the second is a partial MET (right arrow). Both of these transitions result in states with higher stem cell-like character. It should be noted that the model also predicts that some EMTs, and equally some METs, will result in a decrease in stemness and indeed this has been observed when the highly aggressive human DKAT basal-type breast cancer cell line is induced to undergo EMT (N. D'Amato and V. Seewaldt, personal communication). The model also suggests a link between stemness, plasticity, and metastatic propensity, perhaps explained by activation of certain oncogenic pathways (e.g., PI3 kinase/Akt) and developmental pathways.

The model also predicts that cells with maximal stem-cell character, which by definition will be highly malignant, should display both epithelial and mesenchymal traits, because they inhabit intermediate states in the epithelialmesenchymal axis. The highly malignant rat adenocarcinoma AT3-T cells are in this type of state. Importantly, in humans with metastatic breast and prostate carcinomas many CTCs also exist in these intermediate states. These cells correlate with disease progression and are believed to be highly aggressive. A population of cells enriched in CTCs expressed RNAs encoding mesenchymal markers; however, the data did not indicate whether or not epithelial and mesenchymal markers were co-expressed in the same cell. Another clinical example of cells in intermediate states is found in sarcomatoid renal cell carcinomas, which have been shown to co-express epithelial markers, such as epithelial membrane antigen, and mesenchymal ones, like vimentin. These tumors, though rare (1-8% of renal tumors) are highly aggressive and difficult to treat. A similar situation may be found in carcinosarcomas of both the prostate and breast, highly aggressive, rare tumors with mixed epithelial and mesenchymal components but of clonal origin. It is not completely clear whether or not single cells in these tumor co-express epithelial and mesenchymal markers and are thus truly in intermediate states.

Finally, the model suggests that as sarcomas undergo MET they will activate stem cell-like pathways and become more aggressive. Indeed, there are many descriptions of sarcomas with mixed epithelial and mesenchymal components in close proximity as seen in some synovial- and osteo-sarcomas. New genetically-defined mouse models of soft tissue sarcoma should shed light on the existence and importance of cells intermediate cell states in progression of these tumors.

Example 7. Phenotypic Plasticity Among Human Circulating Tumor Cells

The experiments described above indicated that Dunning rat prostate adenocarcinoma cells that inhabit an intermediate phenotypic state are tumorogenic, metastatic, and possess stem cell-like antigens and cellular programs. To investigate whether or not similar transitional cells could play a role in human cancer, cancer cells isolated from blood of men with metastatic castrate resistant progressive prostate cancer (CRPC) or women with progressive metastatic breast cancer (mBC) were examined Circulating tumor cells (CTCs) represent an ideal source of tissue to investigate evidence of this plasticity in vivo, given that these cells are likely to be in circulation prior to and during metastatic colonization. CTCs have both independent prognostic and predictive significance in multiple epithelial malignancies, including breast and prostate cancer. These cells can be collected, isolated, and analyzed for a variety of biomarkers relevant to cancer biology.

Figure 10:
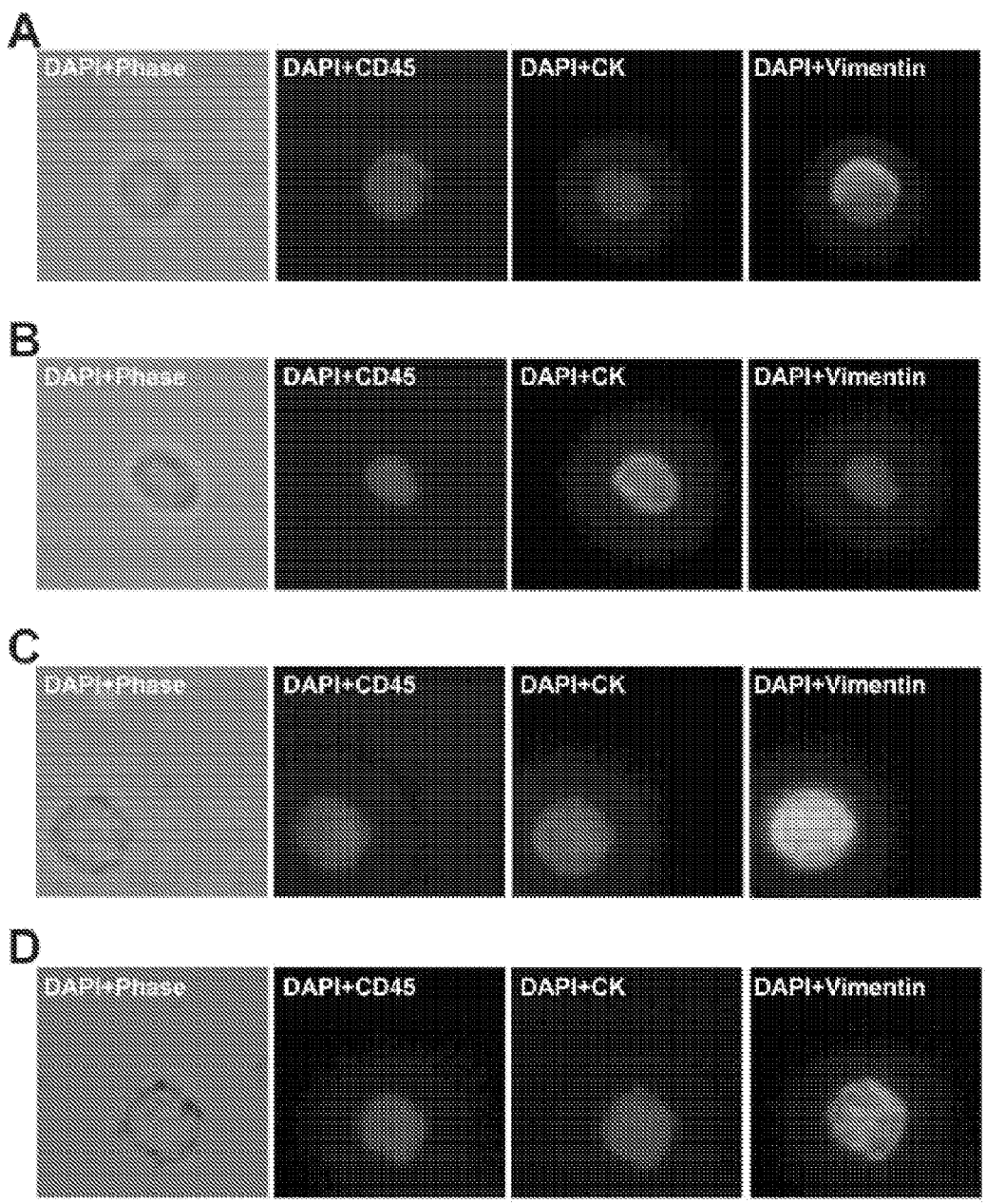
FIG. 10 depicts CTCs from patients with prostate adenocarcinoma. (A) illustrates an example of a leukocyte from a human peripheral blood mononuclear cell (PMBC) sample: CD45 (+), CK (−), and vimentin (+). (B) illustrates an example of a CD45 (−), CK (+), and vimentin (−) cell from a patient with metastatic breast cancer. (C) illustrates an example of a CD45 (−), CK (+), vimentin (+) from a patient with metastatic breast cancer (mBC). (D) illustrates an example of a CD45 (−), CK (+), vimentin (+) from a patient with metastatic progressive castrate-resistant prostate cancer (mCRPC).

It was tested whether there was a high likelihood of finding transitional cells within a population of CTCs captured by FDA-approved EpCAM (Epithelial Cell Adhesion Molecule)-targeted ferromagnetic antibodies. These cells were interrogated for expression of CD45 (expressed in many leukocytes; FIG. 10A), cytokeratin (CK; an epithelial marker), and vimentin (a mesenchymal marker) by immunofluorescence. CTCs were defined as CD45-negative and CK-positive nucleated intact cells (FIG. 10B) and transitional CTCs were so defined if they additionally co-expressed vimentin (FIG. 10C-D). FIG. 10 shows that CTCs from patients with prostate adenocarcinoma stained positive for epithelial and mesenchymal markers. Triple staining was performed using anti-CD45 antibody labeled with Alexa 647, anti-cytokeratin (CK) antibody labeled with Alexa 555, and anti-vimentin antibody labeled with Alexa 488. Nuclei were labeled with DAPI. FIG. 10A shows an example of a leukocyte from a human peripheral blood mononuclear cell sample: CD45 (+), CK (−), and vimentin (+). Additionally, CD45 (+), CK (−), and vimentin (−) cells were observed. FIG. 10B shows an example of a CD45 (−), CK (+), and vimentin (−) cell from a patient with metastatic breast cancer. Such cells were counted as vimentin (−) CTCs in Table 6. FIG. 10C shows an example of a CD45 (−), CK (+), vimentin (+) from a patient with metastatic breast cancer. Such cells were counted as vimentin (+) CTCs in Table 6. FIG. 10D shows an example of a CD45 (−), CK (+), vimentin (+) from a patient with metastatic progressive castrate-resistant prostate cancer. Such cells were counted as vimentin (+) CTCs in Table 6.

Transitional CTCs co-expressed vimentin and CK in many of the patients with elevated CTC counts (≥5 CTCs/7.5 mL by standard testing) (Table 6, FIG. 10). In fact, among nine patients with progressive metastatic CRPC and eight patients with progressive mBC, it was found that approximately 75% (range 0-100%, 85.5% in CRPC, 54% in mBC) of the CTCs stained for both CK and vimentin (FIG. 10C-D), indicating a transitional phenotype. These data indicated that circulating tumor cells in patients with metastatic breast and prostate cancer co-express epithelial (EpCAM and cytokeratin) and mesenchymal (vimentin) markers, and thus exist in a transitional phenotypic state, similar to that observed in our preclinical models.

TABLE 6

Circulating tumor cell (CTC) counts and vimentin expression in patients with metastatic castration resistant prostate or metastatic breast cancer.

| Subject Number | CTC Count (Cellsearch)* | Ratio: vimentin (+) CTCs/ Total CTC Count |
|---|---|---|
| Castrate-Resistance Metastatic Prostates Cancer | | |
| 1 | 5 | 4/6 |
| 2 | 41 | 11/11 |
| 3 | 45 | 6/10 |
| 4 | 626 | 5/8 |
| 5 | 110 | 17/21 |
| 6 | 182 | 5/6 |
| 7 | 17 | 13/16 |
| 8 | 19 | 33/34 |
| 9 | 34 | 12/12 |
| Total | | 106/124 (85.5%) |
| Metastatic Breast Cancer | | |
| 1 | 21 | 0/6 |
| 2 | 7 | 2/2 |
| 3 | 8 | 4/4 |
| 4 | 21 | 1/2 |
| 5 | 12 | 2/2 |
| 6 | 188 | 21/22 |
| 7 | 138 | 8/20 |
| 8 | 377 | 6/23 |
| Total | | 44/81 (54.3%) |
| Overall Total | — | 150/205 (73.1%) |

*Column 2 represents the CTC count as determined by the standard Cellsearch EpCAM based method for each subject, while column 3 represents the number and proportion of CTCs counted manually that were found to express cytokeratin and co-express vimentin, expressed as a ratio and percentage.

Plasticity and CTCs.

The identification of plasticity among CTCs in a significant subset of patient samples offers several important clinical opportunities. Expression of plasticity may have prognostic or predictive value in patients with metastatic cancers, especially mBC where a significant range of values were shown for plasticity. Thus, the subset of patients with very high plasticity may have a more aggressive natural history and exhibit greater resistance to systemic treatments. In terms of diagnosis and utility as predictive biomarkers the data suggested that in addition to cells expressing both epithelial and mesenchymal markers there may be an unknown number of CTCs that have moved further towards the mesenchymal pole and are EpCAM negative. These cells will be missed by the FDA approved CELLSEARCH® System and also by the Adna Test (AdnaGen AG) system and current microfluidic technologies, which enrich for CTCs by immunoabsorbtion of cells expressing MUC1 or EpCAM. Indeed, recent studies in breast cancer have suggested that "normal" type breast cancer cell lines that overexpress both EMT and stem cell antigens (CD44+, CD24-) may lack EpCAM and are thus not detectable by currently approved CTC detection systems. Therefore it is possible that the number of CTCs in patients with metastatic cancer is much higher than currently appreciated. Identification of this additional subset of CTC can provide greater prognostic value than CTC counts as currently determined, as well as earlier detection of CTCs and the metastatic potential in patients with earlier stage disease.

Furthermore, CTCs in intermediate states, which comprise the 50-75% of cells isolated herein from patients with metastatic breast and prostate cancer as well as those cells that may go undetected because they have undergone a more complete EMT, represent a therapeutic problem. It has been well documented that EMT alters drug sensitivity of lung cancer cells and it has been challenging to direct therapy to cancer cells with stem cell-like properties, perhaps because of their recalcitrance to undergo apoptosis.

While recent studies suggest both a screening method and actual compounds (e.g., salinomycin) that can selectively target cancer stem cells, these aggressive cells still represent a formidable therapeutic challenge. Thus, molecules comprising a binding agent that has binding specificity to an EMT biomarker described herein and linked to an anti-cancer agent provide additional therapeutic options.

Example 8. CTCs from Patients with Metastatic Breast and Prostate Cancer Express Vimentin and N-Cadherin Eligible men had progressive metastatic CRPC (progression despite testosterone <50 ng/dL) and were about to begin a new systemic therapy. Eligible women had progressive metastatic breast cancer (mBC) and were about to begin a new systemic therapy. Baseline characteristics of patients (n=29) are presented in Table 7.

TABLE 7

Baseline characteristics of patients (n = 29)

| | Metastatic Prostate (n = 17) | Metastatic Breast (n = 12) |
|---|---|---|
| DEMOGRAPHICS | | |
| Age, median | 69 (59-82) | 61.5 (48-81) |
| Race, Ethnicity | | |
| White, non-hispanic | 76% | 58% |
| Other, non-hispanic | 23% | 42% |

TABLE 7-continued

Baseline characteristics of patients (n = 29)

| | Metastatic Prostate (n = 17) | Metastatic Breast (n = 12) |
|---|---|---|
| BASELINE DISEASE HISTORY | | |
| Gleason Score, median | 7 (7-9) | — |
| ER/PR, % | — | 75%/67% |
| Baseline median PSA, Range | 396.4 (14-13, 419.5) | — |
| Baseline Pain Score (0-10), median | 1 (0-7) | 0 (0-6) |
| Karnofsky Performance Status, median | 90 (70-100) | 90 (70-100) (n = 6) |
| # of Prior Hormonal Therapies | 2 (0-5) | 2 (0-4) |
| Prior Chemotherapy | 47% | 83% |
| Baseline CTC Count, median | 40 (4-828) | 13 (0-1062) |
| METASTATIC SITES | | |
| Lymph Node | 65% | 50% |
| Liver | 24% | 50% |
| Lung | 47% | 42% |
| Bone | 94% | 75% |

CTCs were drawn into standard FDA-approved Cellsave tubes and processed within 48 hours using the CELLSEARCH® methodology using EpCAM-based ferromagnetic capture. A CTC was defined as an intact nucleated (DAPI+) cell that expressed pan-CK and lacked expression of the leukocyte antigen CD45, and was enumerated using standard methods. A second CELLSEARCH® tube was collected and processed using EpCAM capture, and isolated cells were stained for CK (IgG1, AbD Serotec) labeled with Alexa 555, CD45 (IgG1, AbCam) labeled with Alexa 647, and either vimentin (IgG1, BD Biosciences) or N-Cadherin (IgG1, DAKO) using immunofluorescent labeling with Alexa 488. The proportion of CTCs staining positive for an EMT antigen was calculated from the total number of CTCs manually scored from the second tube. Positive controls using American Red Cross-derived PBMCs (CD45), PC3 prostate cancer cells (vimentin, N-cadherin), and T47D breast cancer cells (CK) were used for each marker. Negative controls using mock antibody were used to optimize the staining/scoring of each antigen.

Figure 11:
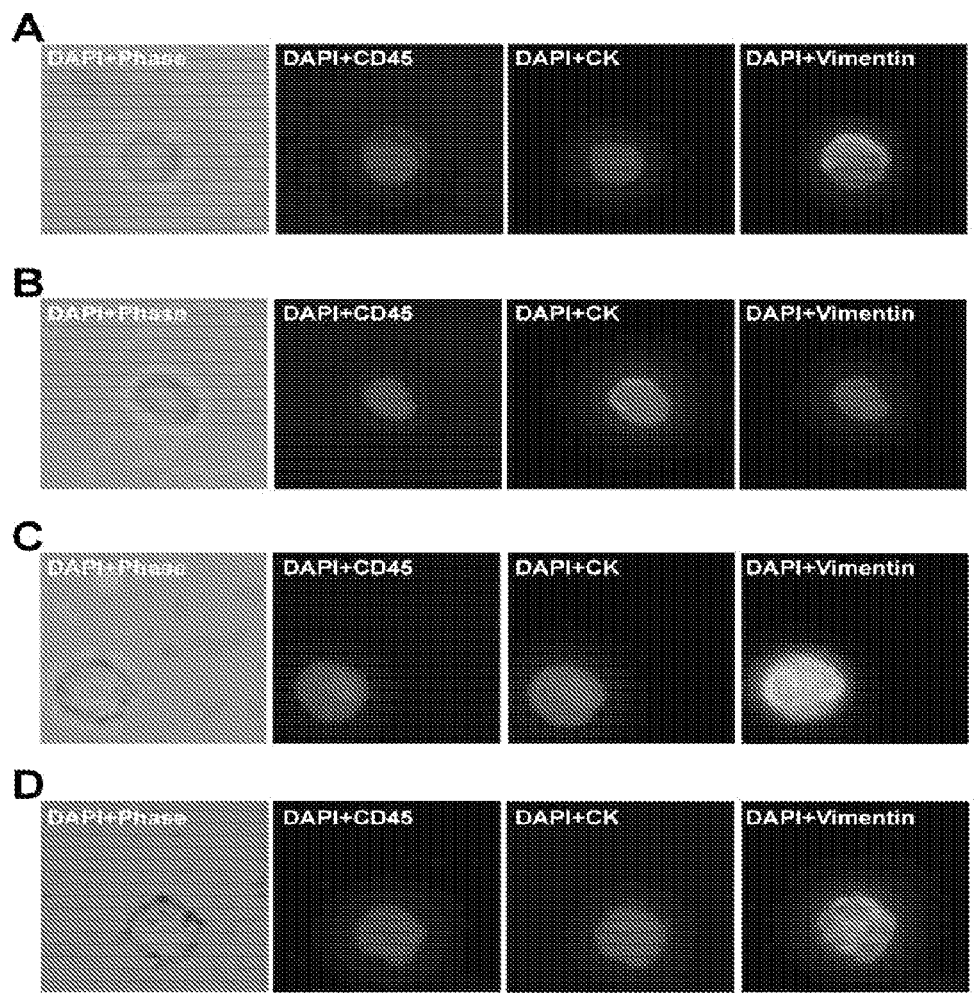
FIG. 11 depicts immunofluorescent images of CTCs from patients with mCRPC and mBC.
Figure 12:
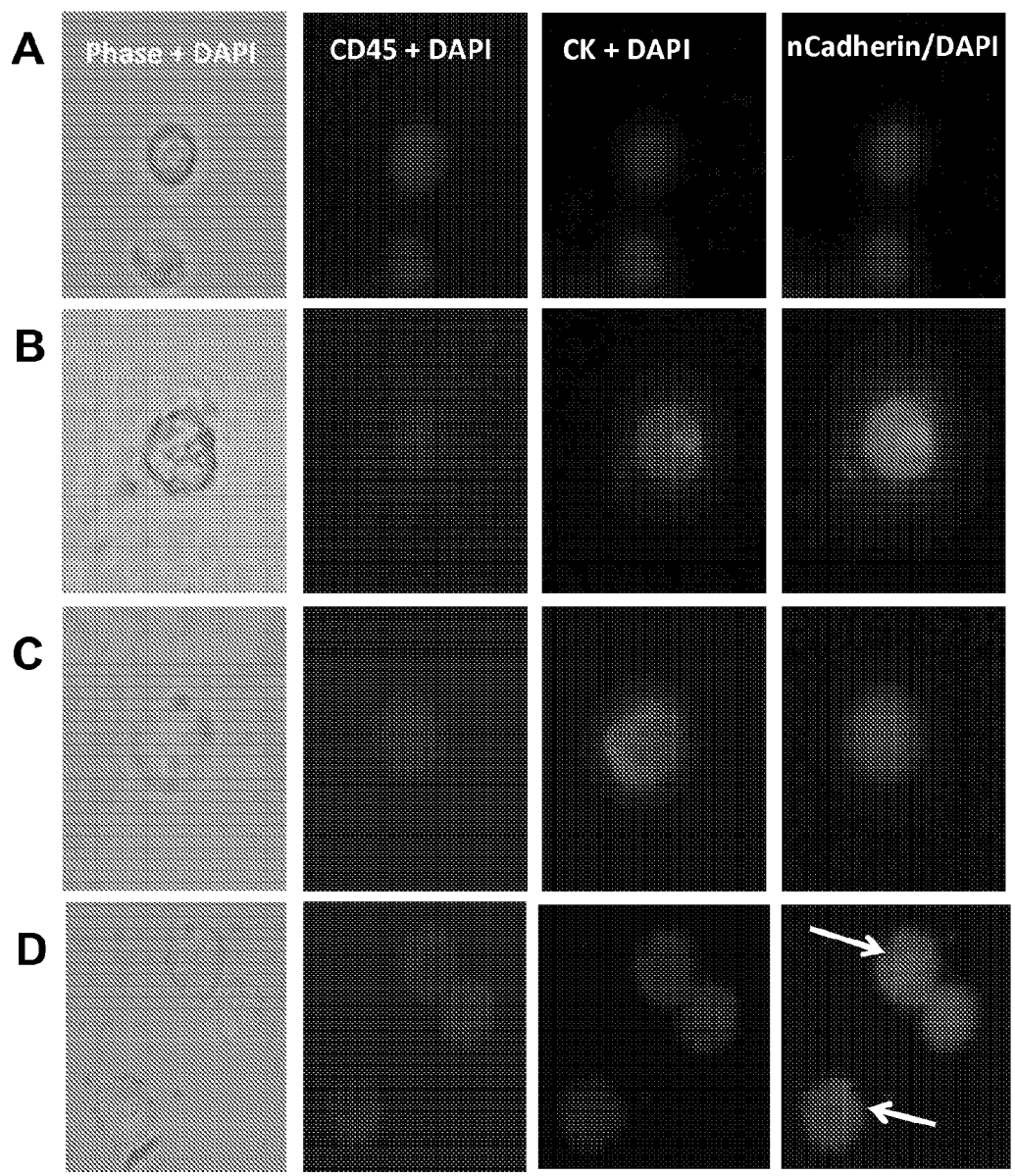
FIG. 12 depicts immunofluorescent images of CTCs from patients with mCRPC and mBC.
Figure 13:
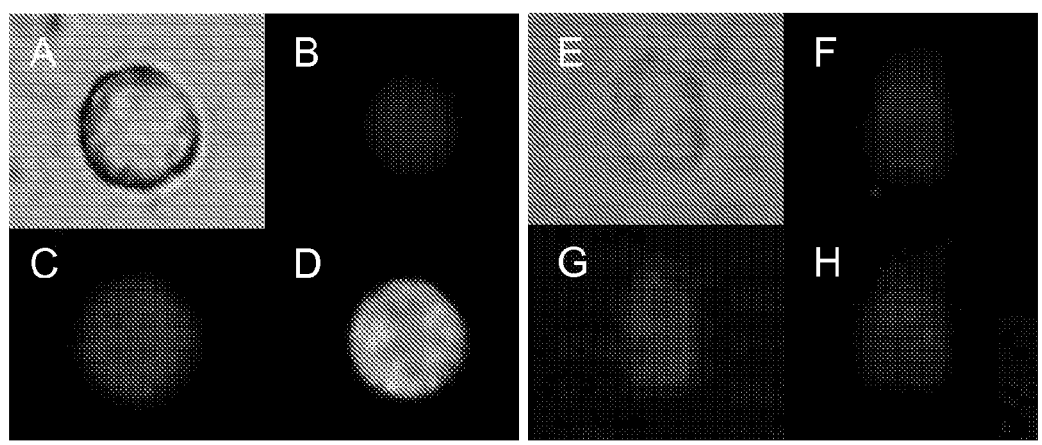
FIG. 13 depicts immunofluorescent images of CTCs from patients with mCRPC and mBC.

Prevalence of vimentin and CK co-expression in CTCs, and prevalence of N-cadherin and CK co-expression in CTCs are presented in Tables 8 and 9, respectively. Vimentin co-expression was detected in 17/20 (85%) patients with mCRPC or mBC and 78% of all CTCs. N-Cadherin co-expression was detected in 8/9 (89%) patients and 81% of CTCs. Immunofluorescent images of CTCs from patients with mCRPC and mBC are shown in FIG. 11 (A, a leukocyte; B, vimentin negative CTC (CRPC); C, vimentin positive CTC (BC); and D) vimentin positive CTC (CRPC)). Immunofluorescent images of CTCs from patients with mCRPC and mBC are shown in FIG. 12 (A, leukocyte; B, Ncad positive CTC (BC); C, Ncad negative CTC (BC); and D, two NCad positive CTCs (arrows) and 1 Ncad negative CTC (CRPC)). Immunofluorescent images of CTCs from patients with mCRPC and mBC are shown in FIG. 13 (A, Phase/DAPI; B, CD45/DAPI; C, CK/DAPI; D, Vimentin/DAPI positivity in a man with mCRPC; E, Phase/DAPI; F, CD45/DAPI; G, CK/DAPI; and H, Vimentin/DAPI negativity in a second man with mCRPC).

The data showed the co-expression of cytokeratin with the EMT antigens vimentin and N-cadherin in CTCs from men with metastatic CRPC and women with metastatic breast cancer. A majority of CTCs examined co-expressed CK and EMT proteins by immunofluorescent labeling. The majority of patients in this study had CTCs that co-expressed vimentin or N-cadherin suggesting potential epithelial plasticity during metastasis. The data suggests that CTCs can lack epithelial markers and provide methods for assessing patients with breast and prostate cancer as well as for the optimal detection of circulating tumor cells in other common malignancies.

TABLE 8

| Subject Number | | CTC Count (Cellsearch) | Ratio of: Vimentin (+) CTCs/ Total Manual CTC Count |
|---|---|---|---|
| castrate-resistant metastatic prostate cancer | 1 | 5 | 4/6 |
| | 2 | 4 | 2/2 |
| | 3 | 54 | 11/11 |
| | 4 | 45 | 6/10 |
| | 5 | 626 | 5/8 |
| | 6 | 110 | 17/21 |
| | 7 | 182 | 5/6 |
| | 8 | 17* | 13/16 |
| | 9 | 19 | 33/34 |
| | 10 | 34 | 12/12 |
| Total | | 1127 | 108/126 (86%) |
| metastatic breast cancer | 1 | 13 | 0/6 |
| | 2 | 85 | 2/2 |
| | 3 | 8 | 4/4 |
| | 4 | 21 | 1/2 |
| | 5 | 12 | 2/2 |
| | 6 | 188 | 21/22 |
| | 7 | 324** | 29/33 |
| | 8 | 377 | 6/23 |
| | 9 | 0 | 0/0 |
| | 10 | 3 | 0/3 |
| Total | | 884 | 65/97 (67%) |
| Overall Total | | — | 173/223 (78%) |

TABLE 9

| Subject Number | | CTC Count (Cellsearch) | Ratio of: N-Cadherin (+) CTCs/ Total Manual CTC Count |
|---|---|---|---|
| castrate-resistant metastatic prostate cancer | 1 | 45 | 13/19 |
| | 2 | 12 | 5/7 |
| | 3 | 10 | 8/8 |
| | 4 | 5 | 8/9 |
| | 5 | 12 | 4/4 |
| | 6 | 221 | 11/13 |
| | 7 | 828 | 81/96 |
| Total | | 1132 | 130/156 (83%) |
| metastatic breast cancer | 1 | 1062 | 9/13 |
| | 2 | 2 | 0/3 |
| Total | | 1064 | 9/16 (56%) |
| Overall Total | | — | 139/172 (81%) |

*Count from 3 months prior to baseline (no intervening therapy)
**Count from time point #2

In a second trial to test for the existence of transitional CTCs, blood was collected from 31 men with mCRPC and 16 women with mBC (see baseline characteristics for the patients in Table 10 and Table 11). CTCs were processed using the CELLSEARCH® EpCAM-based immunocapture method and profiled for expression of CD45 (PTPRC) (a leukocyte marker), cytokeratins (CK) (epithelial markers), vimentin (VIM) and N-cadherin (CDH2) (mesenchymal markers), and CD133 (a stem cell marker) by immunofluorescence (IF) (Table 2). Leukocytes were defined as nucleated (DAPI positive), CD45-positive and CK-negative cells, whereas CTCs were defined as nucleated (DAPI positive), CD45-negative and CK-positive cells. Among CTCs we identified transitional cells as those that additionally expressed vimentin or N-cadherin.

TABLE 10

Baseline demographic and clinical characteristics of the men with metastatic CPRC.

| | n = 31 |
|---|---|
| DEMOGRAPHICS | |
| Age, years (range) | 71 (59-89) |
| Race, Ethnicity | |
| White, non-Hispanic | 71% |
| Black, non-Hispanic | 29% |
| BASELINE DISEASE HISTORY | |
| Median Gleason Score (range) | 8 (5-10) |
| Median Baseline PSA[1] (ng/dl, range) | 267.5 (14.0-13,419.5) |
| Median Baseline Pain (range)[2] | 1 (0-7) |
| Median Karnofsky Performance Status (range) | 90 (60-100) |
| Median Number of Prior Hormonal Therapies (range) | 3 (0-5) |
| Prior Chemotherapy | 65% |
| Prior Bisphosphonates | 71% |
| SITES OF METASTATIC DISEASE | |
| Visceral (lung + liver) | 35% |
| Lymph Node Only | 0% |
| Bone metastatic: | |
| Bone Metastatic With Lymph Nodes (no visceral metastases) | 39% |
| Bone Metastatic Without Lymph Nodes (no visceral metastases) | 26% |

[1]PSA: prostate specific antigen.
[2]Pain is scored as a linear analog scale (0-10 range).

TABLE 11

Baseline characteristics of mBC patients.

| | n = 16 |
|---|---|
| DEMOGRAPHICS | |
| Median age (range) | 61 (48-81) |
| Race, Ethnicity | |
| White, non-Hispanic | 44% |
| Black, non-Hispanic | 50% |
| Asian, non-hispanic | 6% |
| BASELINE DISEASE HISTORY | |
| ER and/or PR positive disease | 56% |
| HER2 positive disease (HER2 3+) | 0% |
| Median Karnofsky Performance Status (range) | 90 (70-90) |
| Median Number of Prior EndocrineTherapies (range) | 1 (0-4) |
| Median Number of Prior Chemotherapies (range) | 2 (0-7) |
| SITES OF METASTATIC DISEASE | |
| Visceral (lung or liver) | 75% |
| Lymph Node Only | 0% |
| Lymph Node, soft tissue, or contralateral breast only | 13% |

TABLE 11-continued

Baseline characteristics of mBC patients.

|  | n = 16 |
| --- | --- |
| Bone metastases only: | |
| Bone Metastatic With Lymph Nodes (no visceral metastases) | 0% |
| Bone Metastatic Without Lymph Nodes (no visceral metastases) | 13% |

Figure 14:
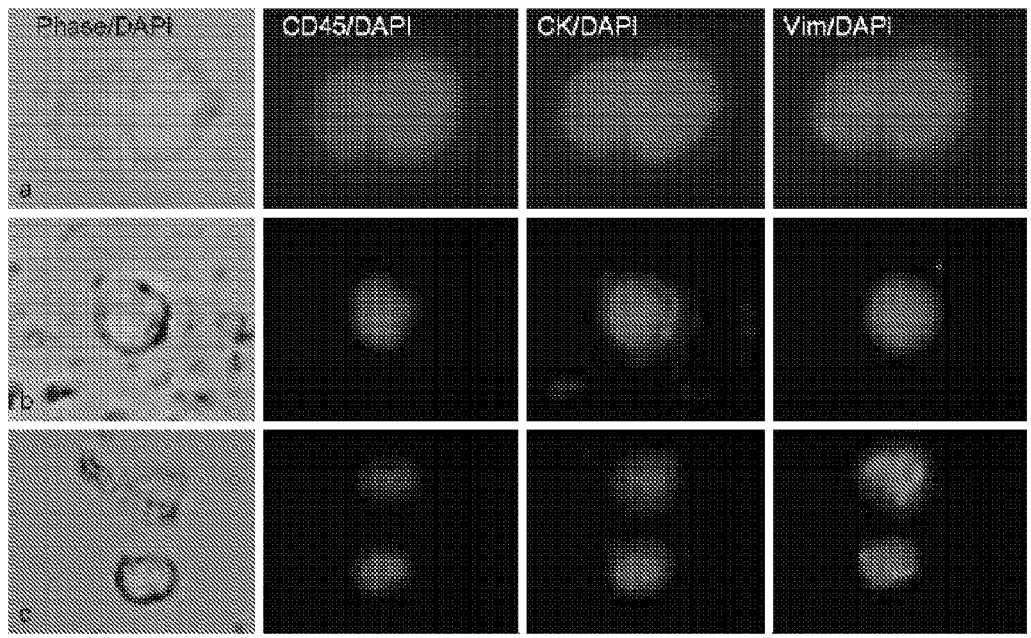
FIG. 14 depicts immunofluorescent images of CTCs from patients with mCRPC and mBC.
Figure 14:
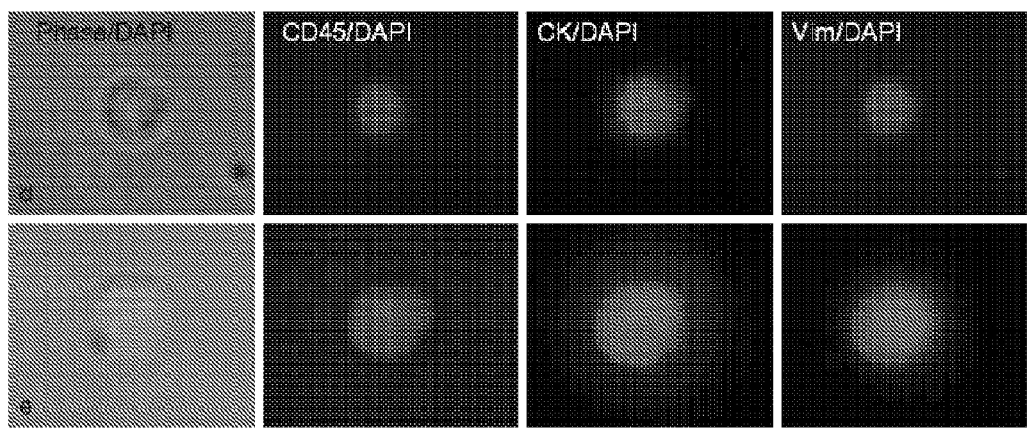

Among ten men with mCRPC, CTCs co-expressed vimentin and CK in 10/10 (100%) patients, and by this criterion 108/126 (86%) of enumerated CTCs were transitional (Table 12, FIG. 14). Biopsies of bony metastases performed within one week of CTC collection in two of these patients revealed no vimentin expression in the CK positive tumor foci, but strong vimentin expression in the surrounding bone stroma, which lacks CK expression. These same patients had CTCs taken at the same time as the CT-guided tumor biopsy that commonly expressed co-expressed CK and vimentin. These findings are consistent with invasion and metastasis by transitional CTCs that subsequently undergo MET; alternatively, vimentin expression may be heterogeneously expressed in metastases, similar to CTC expression.

TABLE 12

Circulating tumor cell (CTC) and transitional CTCs in patients with metastatic CRPC.

| Subject Number | CTC Count (Cellsearch)[i] | Ratio: Vimentin (+) CTCs/ Total Manual CTC Count[ii] |
| --- | --- | --- |
| 1 | 5 | 4/6 |
| 2 | 4 | 2/2 |
| 3 | 54 | 11/11 |
| 4 | 45 | 6/10 |
| 5 | 626 | 5/8 |
| 6 | 110 | 17/21 |
| 7 | 182 | 5/6 |
| 8 | 17 | 13/16 |
| 9 | 19 | 33/34 |
| 10 | 34 | 12/12 |
| Total | 1127 | 108/126 (86%) |

| Subject Number | CTC Count (Cellsearch) | Ratio: N-Cadherin (+) CTCs/ Total Manual CTC Count |
| --- | --- | --- |
| 11 | 45 | 13/19 |
| 12 | 12 | 5/7 |
| 13 | 10 | 8/8 |
| 14 | 5 | 7/8 |
| 15 | 12 | 3/4 |
| 16 | 220 | 11/13 |
| 17 | 828 | 81/96 |
| 18 | 26 | 6/11 |
| 19 | 12 | 18/22 |
| 20 | 42 | 15/18 |
| Total | 1224 | 167/206 (81%) |

| Subject Number | CTC Count (Cellsearch) | Ratio: CD133 (+) CTCs/ Total Manual CTC Count |
| --- | --- | --- |
| 21 | 485 | 38/38 |
| 22 | 16 | 6/11 |
| 23 | 91 | 15/21 |
| 24 | 6 | 0/0 |
| 25 | 36 | 29/29 |

TABLE 12-continued

Circulating tumor cell (CTC) and transitional CTCs in patients with metastatic CRPC.

| 26 | 27 | 9/9 |
| --- | --- | --- |
| 27 | 43 | 10/15 |
| 28 | 2 | 0/0 |
| 29 | 23 | 12/14 |
| 30 | 38 | 23/26 |
| 31 | 30 | 12/17 |
| Total | 797 | 154/180 (86%) |

[i]The middle column represents the CTC Count from the FDA-approved Cellsearch® enumeration of CTCs for each subject.
[ii]Right column represents the ratio of vimentin (co-expression of vimentin ranged from 60-100% of cells in a given individual and did not correlate with CTC count ($R^2 = 0.11$)), N-cadherin (Co-expression of N-cadherin ranged from 55-100% of cells in a given individual, and did not correlate with CTC count ($R^2 = -0.09$)), or CD133 (CD133 co-expression ranged from 55-100% of evaluable cells in a given individual and did not correlate with CTC number ($R^2 = 0.04$)) expressing CTCs among the total number of CTCs that were manually enumerated. A CTC was defined as an intact DAPI positive (nucleated) cell that lacked CD45 expression and expressed cytokeratin.

TABLE 13

CTCs and transitional CTCs in patients with mBC.

| Subject Number | CTC Count (Cellsearch)[i] | Ratio: Vimentin (+) CTCs/ Total Manual CTC Count[ii] |
| --- | --- | --- |
| 1 | 21 | 0/6 |
| 2 | 7 | 2/2 |
| 3 | 8 | 4/4 |
| 4 | 21 | 1/2 |
| 5 | 12 | 2/2 |
| 6 | 188 | 21/22 |
| 7 | 324 | 29/33 |
| 8 | 377 | 6/23 |
| 9 | 0 | 0/0 |
| 10 | 3 | 0/3 |
| Total | 961 | 65/97 (67%) |

| Subject Number | CTC Count (Cellsearch) | Ratio: N-Cadherin (+) CTCs/ Total Manual CTC Count |
| --- | --- | --- |
| 11 | 1062 | 9/13 |
| 12 | 2 | 0/3 |
| 13 | 147 | 52/59 |
| 14 | 6 | 2/5 |
| 15 | 33 | 15/15 |
| 16 | 2 | 0/0 |
| Total | 1252 | 78/95 (82%) |

Figure 15:
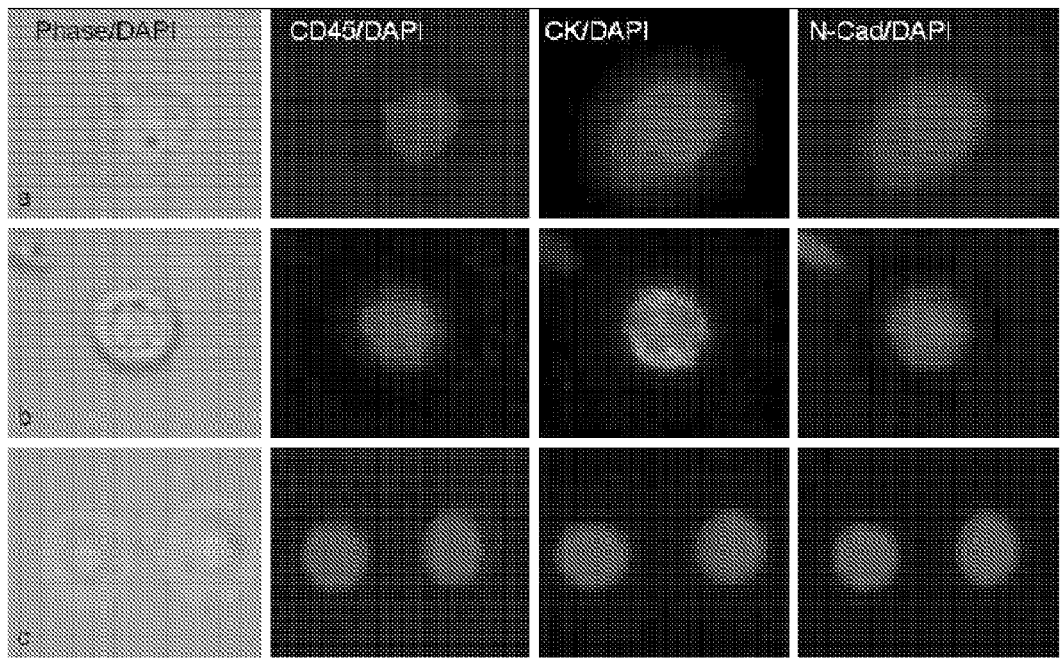
FIG. 15 depicts immunofluorescent images of CTCs from patients with mCRPC and mBC.
Figure 15:
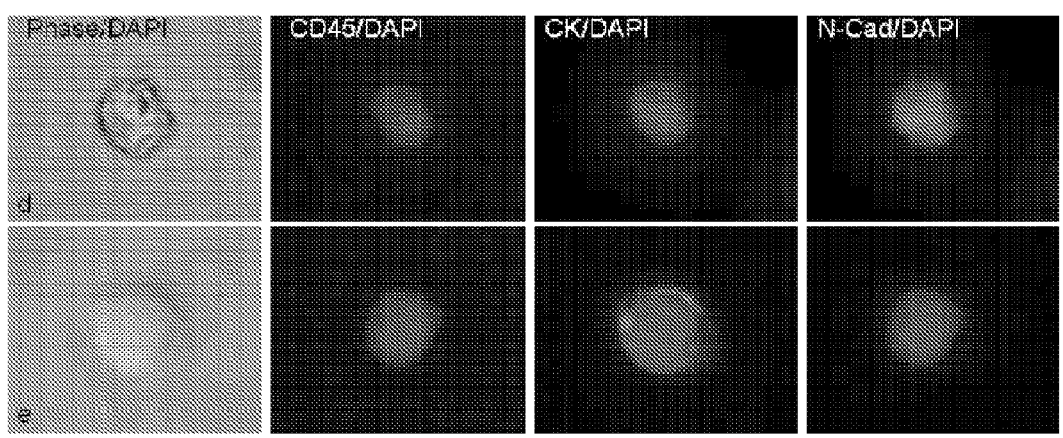

Among the next cohort of 10 men with mCRPC, CTCs co-expressed N-cadherin and CK in 10/10 (100%) patients, and by this criterion 167/206 (81%) of CTCs were identified as transitional (Table 12, FIG. 15). Among 10 women with mBC, nine had detectable CTCs and of these, we found evidence of vimentin co-expression in seven (78%) patients, and 55/88 CTCs overall (63%) co-expressed vimentin (Table 13, FIG. 14). Among another six women with detectable CTCs and mBC, four had evidence of CK and N-cadherin co-expression, and overall 78/95 CTCs (82%) had N-cadherin expression, with significant heterogeneity in expression in a given individual (Table 13, FIG. 15). These data indicate that many CTCs in patients with mBC and mCRPC co-express epithelial (EpCAM and cytokeratin) and mesenchymal (vimentin, N-cadherin) markers, and thus exist in a transitional phenotypic state, similar to that observed in our preclinical models.

Figure 16:
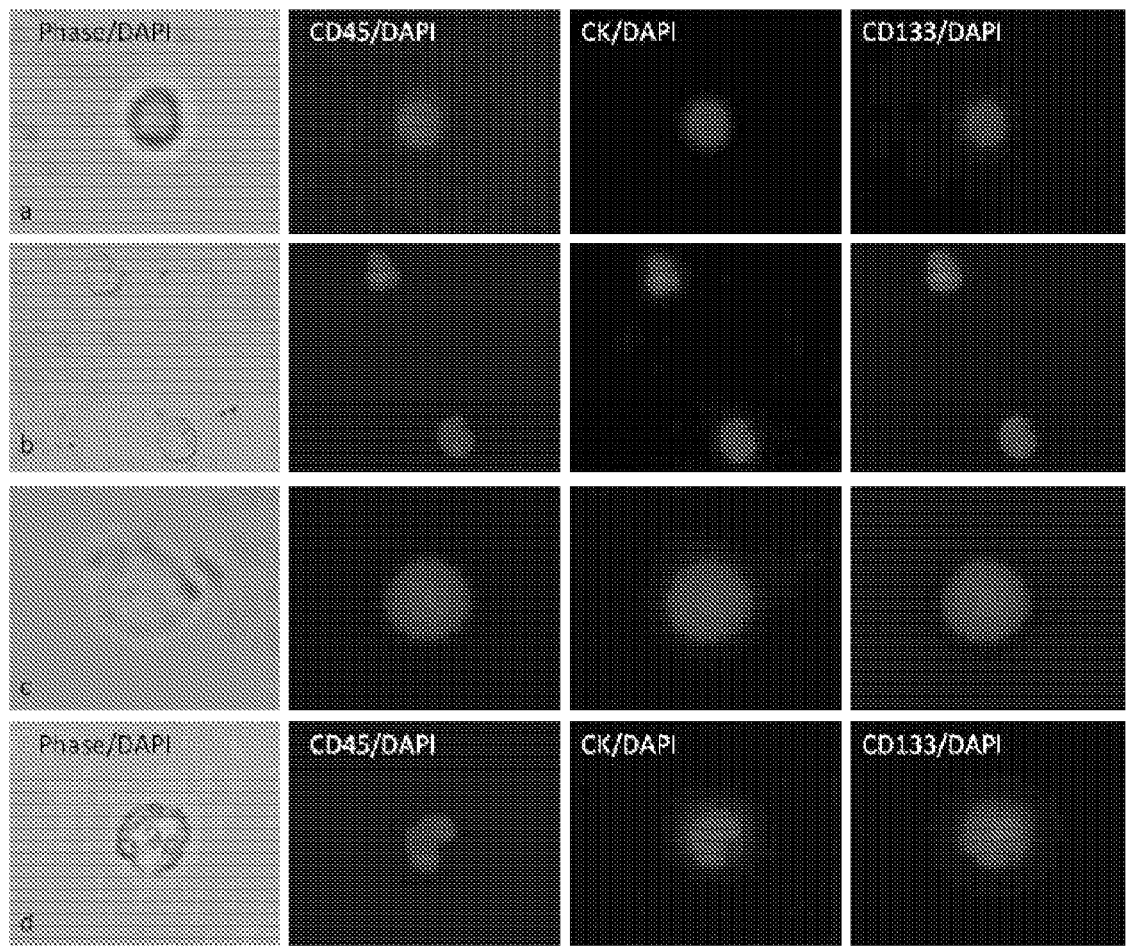
FIG. 16 depicts immunofluorescent images of CTCs from patients with mCRPC and mBC.

Given the expression of the stem cell associated antigen CD133 in transitional AT3-T cells, CD133 expression in CTCs from men with mCRPC was evaluated. CD133 was expressed in 11/11 (100%) men with CTCs, and in 154/180 (86%) of CTCs from these men (Table 12, FIG. 16). These data suggest that CTCs from patients with common epithelial malignancies inhabit transitional states characterized by co-expression of epithelial and mesenchymal markers as well as CD133, biomarkers that have been associated with stem-like properties, invasiveness, and chemoresistance.

Example 9. CTC Isolation

Antibody Selection.

For cell capture, several antibodies against the extracellular domain of OB-cadherin or N-cadherin were tested using positive control (PC3) and negative control (LNCaP) cell lines and analyzed by flow cytometry. The antibodies with the highest signal in the PC3 cells and minimum background with LNCaP cells were selected for conjugation to magnetic particles. The anti-OB-cadherin antibody (R&D Systems, clone 283416) and anti-N-cadherin antibody (Santa Cruz Biotechnology, D-4) were conjugated to magnetic particles using procedures similar to previously described methods (Allard et al. (2004) Clin Cancer Res 10:6897-6904; see also U.S. Pat. No. 6,645,731).

Mesenchymal Capture Assay.

A mesenchymal capture assay was used with the CELL-SEARCH® platform (Veridex LLC), including the CELL-TRACKS® AUTOPREP® for sample preparation and the CELLTRACKS ANALYZER II® for analysis of the captured cells (Allard et al. (2004) Clin Cancer Res 10:6897-6904). The mesenchymal capture assay included ferrofluid coated with anti-OB-cadherin antibodies or anti-N-cadherin antibodies to produce a capture reagent, which would immunomagnetically enrich mesenchymal cells, and staining reagents, such as a phycoerythrin (PE)-conjugated antibody that binds to β-catenin (clone L54E2 from Cell Signaling Technology, Inc.); an antibody to CD45 conjugated to allophycocyanin (APC); and nuclear dye 4',6-diamidino-2-phenylindole (DAPI) to fluorescently label the cells. The assay included buffers to wash, permeabilize, and resuspend the cells such as the following components from the CELL-SEARCH® kit: capture enhancement reagent, permeabilization reagent, cell fixative, and dilution buffer.

Sample Preparation.

7.5 mL of blood was transferred to 15 mL CELL-TRACKS® AUTOPREP® sample tubes and mixed with 6.5 mL of dilution buffer, centrifuged at 800 g for 10 min, and then placed on the CELLTRACKS® AUTOPREP® (Veridex LLC) for automated sample preparation using the mesenchymal capture assay. After aspiration of the plasma and buffer layer by the instrument, ferrofluid was added. After the incubation period and subsequent magnetic separation, unbound cells and remaining plasma were aspirated. The target cells were enriched, fluorescently labeled, and resuspended using the CELLTRACKS® AUTOPREP® in the MAGNEST® Cell Presentation Device (Veridex LLC). The magnetic field generated by the MAGNEST® device caused the magnetically labeled cells to distribute uniformly over the analysis surface of the cartridge for analysis using the CELLTRACKS ANALYZER II®.

Sample Analysis.

After ferromagnetic antibody capture, the staining reagents were added, along with a permeabilization buffer, to fluorescently label the immunomagnetically enriched cells. The cells were stained with labeled anti-β-catenin antibodies, labeled anti-CD45 antibodies, and DAPI for visualization. The anti-β-catenin antibodies was used to identify mesenchymal CTCs. After incubation on the system, the magnetic separation was repeated, and excess staining reagents were aspirated. In the final processing step, the cells were resuspended in the MAGNEST® device, which included a chamber and two magnets that oriented the immunomagnetically labeled cells for analysis using the CELLTRACKS ANALYZER II®.

Figure 17:
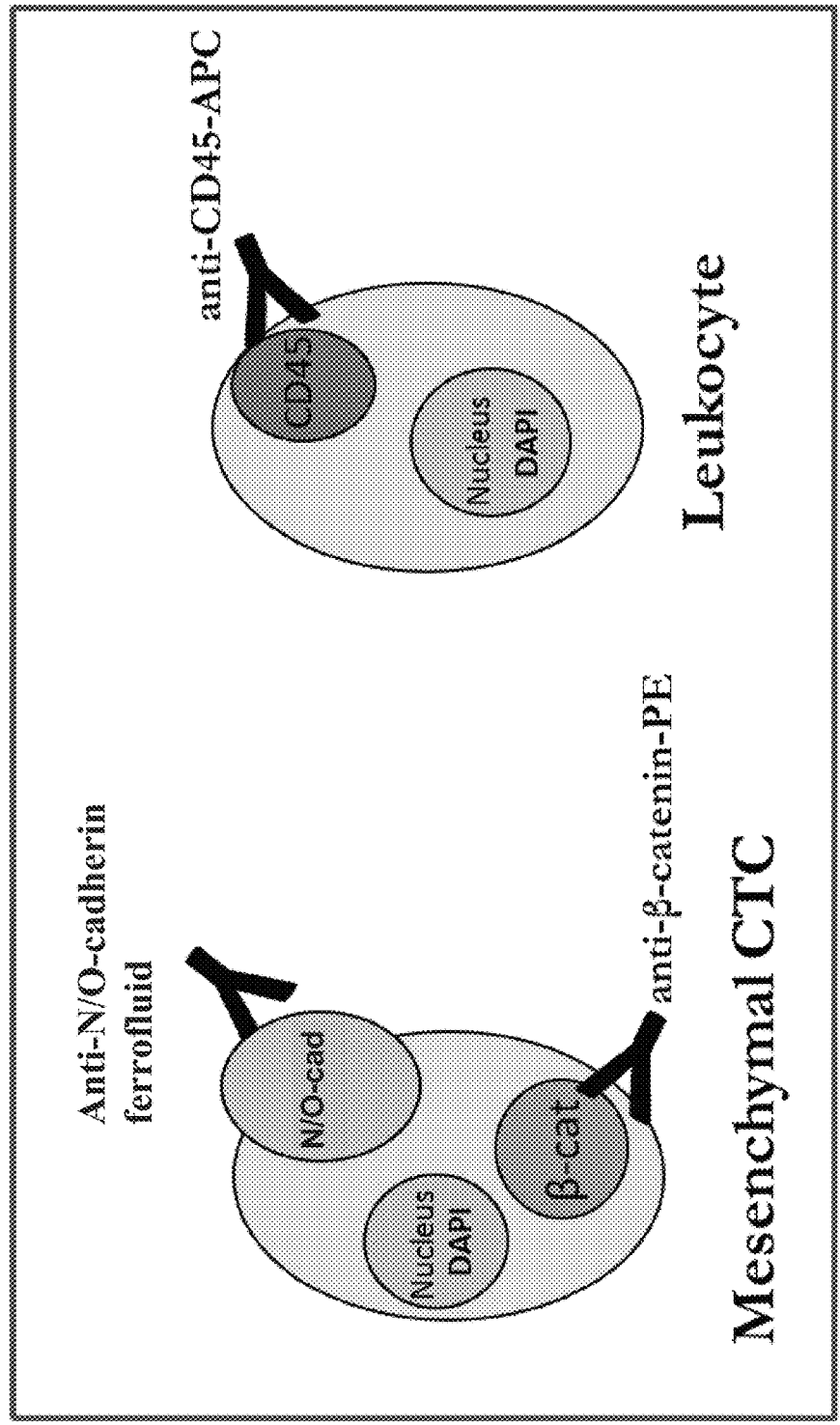
FIG. 17 depicts after enrichment using anti-N-cadherin or anti-OB-cadherin ferrofluid, mesenchymal CTCs were differentiated from leukocytes by the presence of β-catenin expression and the lack of CD45 expression.

The MAGNEST® was placed on the CELLTRACKS ANALYZER II®, a four-color semi-automated fluorescence microscope. Image frames covering the entire surface of the cartridge for each of the four fluorescent filter cubes were captured. The captured images that contained PE as well as DAPI positive events in the same frame were presented in a web-enabled browser gallery for classification of the events based on cell fluorescence and morphology. The final selection of the cells was made by the operator. The criteria to classify the object as a mesenchymal cell (designated as "events") included round to oval morphology, an intact cell greater than 4 μm with a visible nucleus (DAPI positive), positive staining for anti-β-catenin-PE, and negative staining for anti-CD45-APC, as depicted in FIG. 17. Results of cell enumeration were expressed as the number of cells per 7.5 mL of blood.

Figure 18:
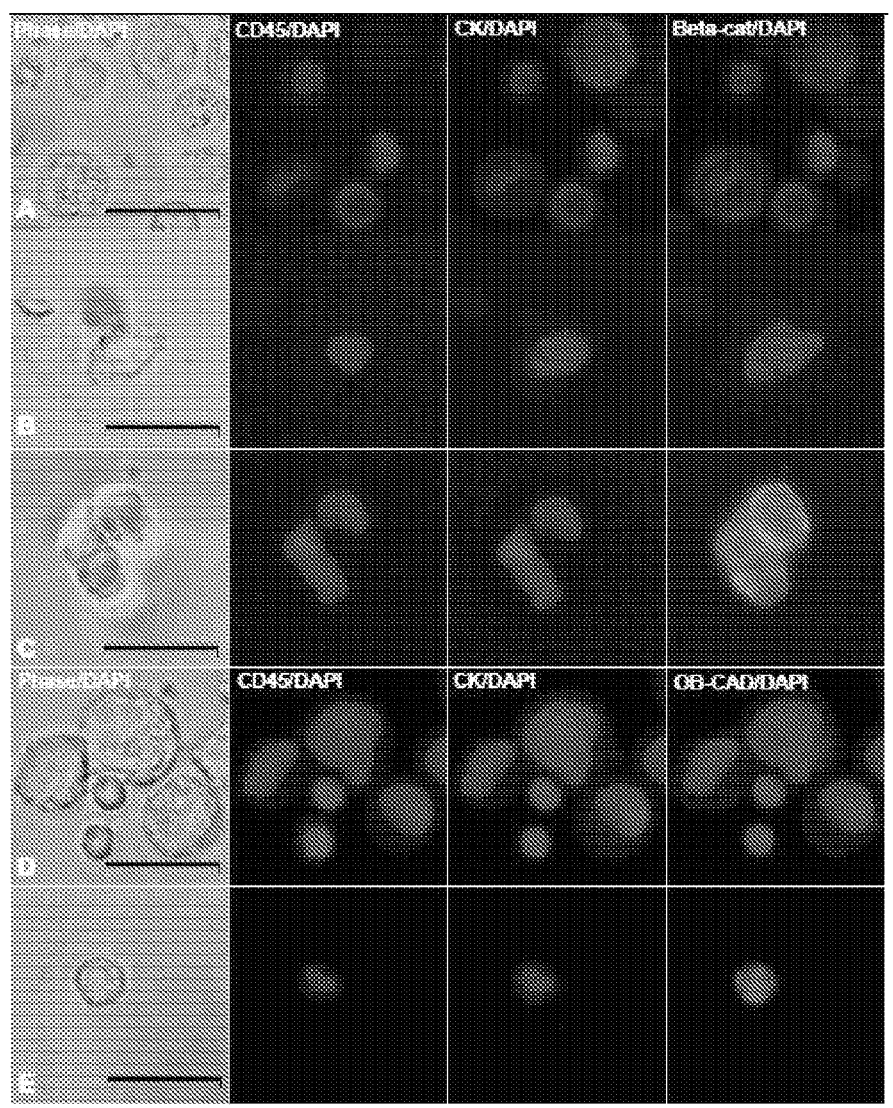
FIG. 18 depicts immunofluorescent images of control cells (PC-3 cells mixed with peripheral blood mononuclear cells) in rows A and D and patient-derived EpCAM-captured cells in rows B, C, and E. Cells are stained for CD45 and cytokeratin and further characterized by either β-catenin or OB-cadherin expression. Columns represent phase microscopy with 4',6-diamidino-2-phenylindole (DAPI), CD45 with DAPI, Cytokeratin (CK) with DAPI, and either β-catenin (beta-cat) or OB-cadherin (OB-CAD) with DAPI. Row A shows CD45-positive control cells lacking β-catenin and CK-positive control cells expressing β-catenin. Row B shows a CTC from a man with prostate cancer with both CK and β-catenin expression, while row C shows a CD45-negative, CK-negative patient cell with β-catenin expression. Row D illustrates CD45-positive control cells lacking OB-cadherin and CK-positive control cells expressing OB-cadherin, and row E shows a CTC with both CK and OB-cadherin expression.
Figure 19:
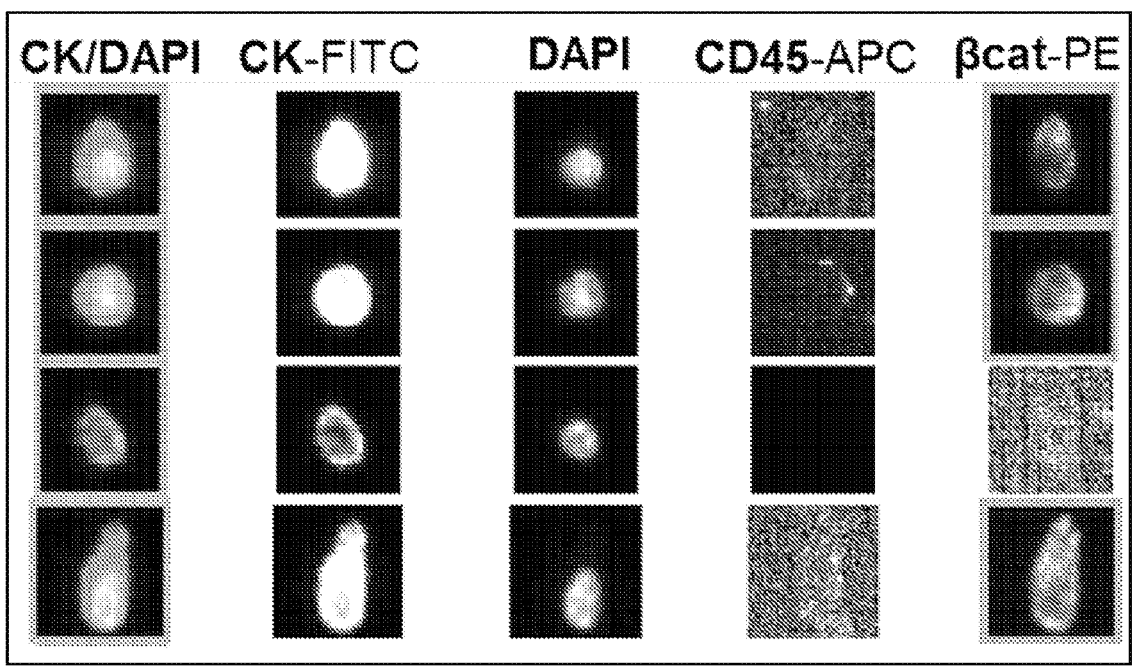
FIG. 19 depicts examples of β-catenin expression in EpCAM-captured CTCs from a man with castration-resistant prostate cancer.

An isolated "CTC" using this assay was defined as a β-catenin positive, CD45 negative, nucleated intact cell, based on our preliminary data that beta-catenin was visualized in tumor cells but not in leukocytes, as illustrated in FIG. 18. In comparison, 50-75% of EpCAM-captured CTCs stained for β-catenin, as shown in FIG. 19 (Bitting et al. (2012) J Clin Oncol 30S:abstr 10533). A mesenchymal CTC phenotype was identified using the OB-cadherin antibody or N-cadherin antibody ferrofluid to capture CTCs with positive β-catenin expression, lack of CD45 expression, and positive nuclear DAPI staining to characterize the cells.

Figure 20:
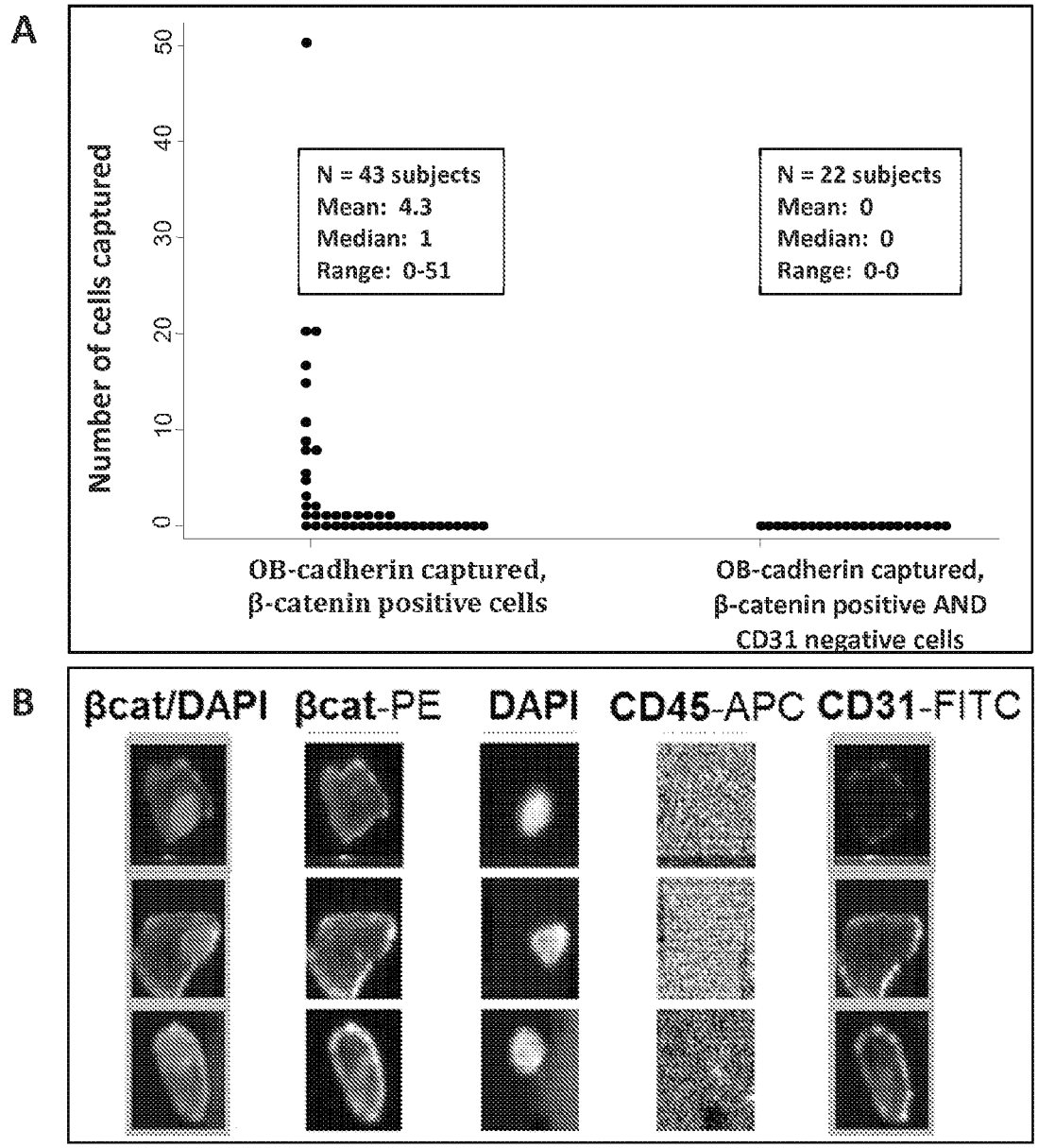
FIG. 20 depicts (A) the distribution of OB-cadherin-captured, β-catenin-positive events from healthy volunteers based on CD31 status. All samples in which CD31 was assessed are CD31 positive; and (B) examples of CD31+ cellular events detected in healthy volunteers.
Figure 21:
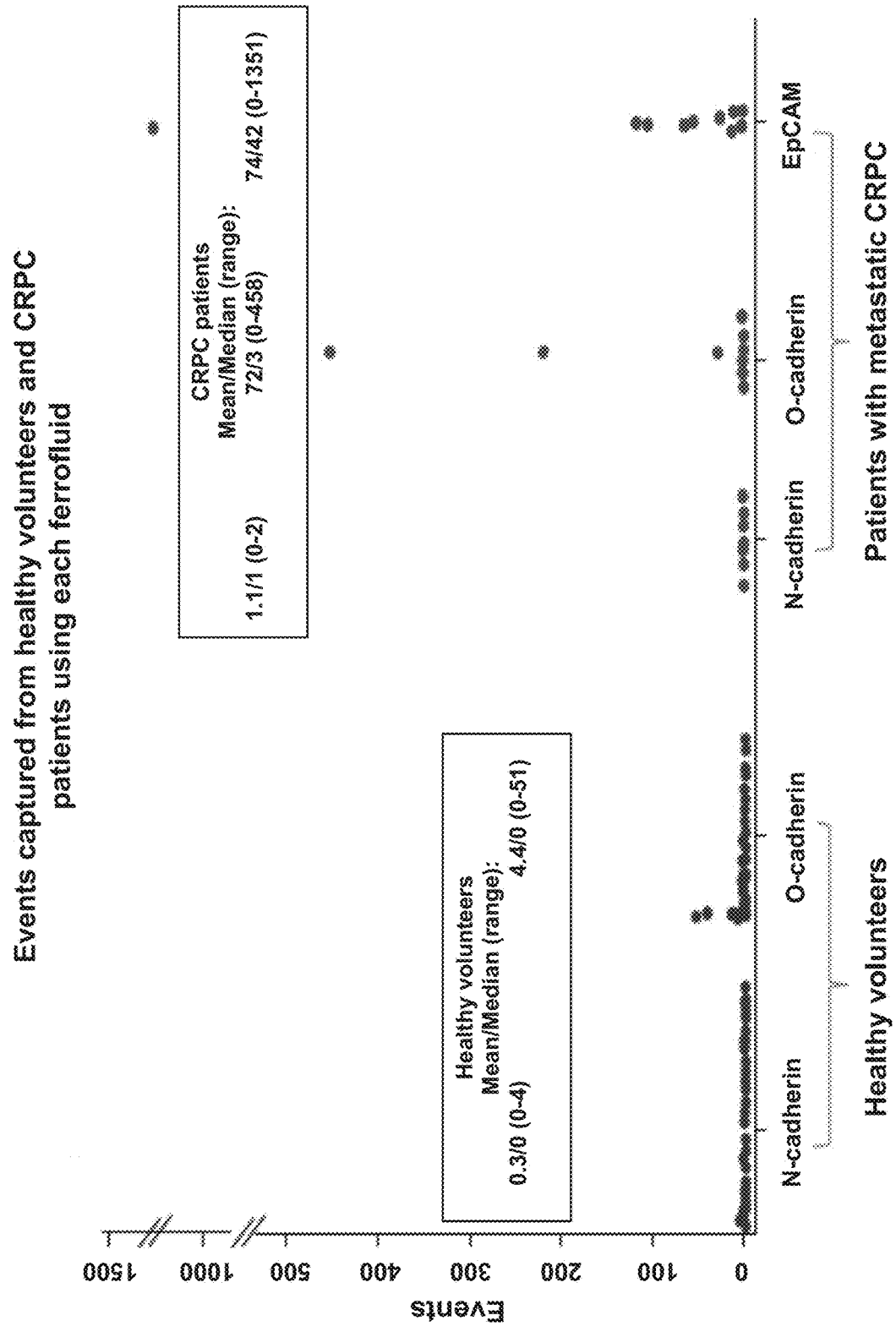
FIG. 21 depicts events captured from healthy volunteers and CRPC patients using N-cadherin, OB-cadherin, or EpCAM ferrofluid.

To determine if circulating mesenchymal-like tumor cells meeting the above criteria were present in healthy individuals, blood was drawn from healthy adults age over 18 years of age into 10 mL EDTA tubes. Subjects were not eligible if they had any chronic medical condition requiring medication or a history of cancer. Samples were processed as described above within 8 hours of blood collection. All subjects were enrolled using an institutional review board-approved protocol and provided informed consent. The OB-cadherin-captured, β-catenin-positive events ("rare events") were detected in healthy volunteers. The rare events detected in healthy volunteers were stained with the endothelial marker CD31 (BD Biosciences, clone WM59) for further characterization as previously described (Pusztaszeri et al. (2006) J Histochem Cytochem 54:385-395). All detected events in healthy volunteers were CD31 positive, which indicates that these cells may represent endothelial cells. Examples of the OB-cadherin captured, β-catenin-positive and CD31-positive events in healthy individuals are shown in FIG. 20.

After establishing a threshold for detection in healthy volunteers (zero OB-cadherin, β-catenin-positive cells if CD31 was included as an additional characterization marker), the prevalence of these cellular events was determined in men with progressive, metastatic CRPC that were enrolled in a correlative clinical blood-drawing study prior to initiating a new systemic therapy. See Table 14. This population largely was composed of men with bone metastases (>90%) and would thus theoretically be enriched for OB-cadherin positive cells, if present.

TABLE 14

| Baseline characteristics of CRPC patients | Results (n = 10) |
|---|---|
| Median age, years (range) | 68 (57-74) |
| Race | |
| Caucasian, n (%) | 7 (70) |
| Black, n (%) | 3 (30) |
| Karnofsky performance status, median (range) | 90 (80-100) |
| Gleason score, median (range) | 8 (7-10) |
| Pain score >4, n (%) | 4 (40) |
| Initial local therapy | |
| Prostatectomy, n (%) | 3 (30) |
| External beam radiation, n (%) | 3 (30) |
| None, n (%) | 4 (40) |
| Laboratory values | |
| PSA ng/mL, median (range) | 408 (7-4377) |
| LDH U/L, median (range) | 220 (206-291) |
| Hemoglobin g/dL, median (range) | 9.8 (8.8-12.1) |
| Alkaline phosphate U/L, median (range) | 197 (57-463) |
| CTC count, median (range) | 34 (1-1000) |
| Sites of metastasis | |
| Bone, n (%) | 10 (100) |
| Liver, n (%) | 2 (20) |
| Lung, n (%) | 4 (40) |
| Lymph nodes only | 0 |
| Prior therapies | |
| Number of hormonal therapies, median (range) | 4 (1-5) |
| Abiraterone, MDV3100, or TAK700, n (%) | 7 (70) |
| Siputeucel-T, n (%) | 3 (30) |
| Docetaxel, n (%) | 8 (80) |
| Cabazitaxel, n (%) | 2 (20) |
| >1 chemotherapy, n (%) | 2 (20) |
| Bone targeted therapy, n (%) | 9 (90) |
| Palliative radiation, n (%) | 3 (30) |
| Type of Progression prior to study enrollment | |
| Imaging | 8 (80) |
| Clinical (symptoms, PSA increase) | 2 (20) |

One CELLSAVE® and two EDTA 10 mL tubes of blood were collected at baseline, at treatment cycle 3, and at progression. Blood obtained in EDTA tubes was used for OB-cadherin capture in duplicate and was processed as soon as possible, with no more than 8 hrs elapsing from the time of collection. Blood obtained in the CELLSAVE® tubes was used for the standard EpCAM capture only and was processed within 72 hours, per the established protocol (Allard et al. (2004) Clin Cancer Res 10:6897-6904). Using the CELLSEARCH® system, circulating mesenchymal cells were captured with the anti-OB-cadherin ferrofluid, then permeabilized and stained for further characterization, as described above. Cells were enumerated per 7.5 mL of blood, and the mesenchymal CTC enumeration was compared with the standard EpCAM-based capture method. Any discrepancy in the scoring of events was resolved with discussion between two independent reviewers.

The EpCAM-based capture assay detected more tumor cells in the majority of patients, however there were exceptions in which more mesenchymal events were seen. Also, OB-cadherin capture resulted in more sheets or clumps of cells and multiple cells per field than EpCAM capture, as illustrated in FIG. 22.

As shown in Table 15, rare events were detected in healthy volunteers using the mesenchymal capture methods. In CRPC patients, OB-cadherin capture ("O-cad capture") detected more events in 3 of 5 subjects than EpCAM-based capture, and the majority of captured cells were cytokeratin negative.

TABLE 15

| | O-cad capture, beta-catenin+ | N-cad capture, beta-catenin+ | EpCAM capture, cytokeratin+ |
|---|---|---|---|
| Healthy Volunteers | 0-51 events (mean 5.95) n = 21 | 0-4 events (mean 0.28) n = 25 | NA |
| CRPC patients | 0-465 events (mean 138.4) n = 5 | 0-2 events (mean 1.2) n = 5 | 1-123 CTCs (mean 50.8) n = 5 |

Table 16 shows events captured of cells in the blood from CRPC patients using the N-cadherin ("N-cad") and OB-cadherin ("O-cad") ferrofluid. The number of cells captured from the CRPC patients appeared to be higher in some patients as compared with the EpCAM-based technology, and the rate of detection appeared higher than that in healthy volunteers for at least OB-cadherin capture.

TABLE 16

| | N-cad Capture | | O-cad capture | | EpCAM Capture | | CELLSEARCH® |
|---|---|---|---|---|---|---|---|
| Subject | #events | CD31+ | #events | CD31+ | #events | CD31+ | standard-of-care |
| 1 | 2 | na | 4 | na | 102 | na | 46 |
| 2 | 1 | na | 458 | na | 71 | na | 45 |
| 3 | 2 | na | 3 | na | 2 | na | 7 |
| 4 | 0 | — | 0 | — | 31 | na | 50 |
| 5 | 1 | na | 220 | na | 17 | na | 23 |
| 6 | 1 | 1 | 3 | 0 | 1351 | na | >1000 |
| 7 | na | na | 1 | 0 | 0 | — | 1 |
| 8 | 2 | 0 | 0 | — | 53 | 1 | 22 |
| 9 | 0 | — | 29 | 29 | 9 | 0 | 12 |
| 10 | na | na | 2 | 1 | 111 | 1 | 69 |

Example 10

To verify that the mesenchymal capture assay using anti-OB-cadherin antibodies could isolate and detect the cells of interest, spiking studies of positive and negative control cells were performed. Preliminary data investigating OB-cadherin expression on the prostate cancer PC-3 cell line revealed OB-cadherin expression on approximately 40-50% of PC3 cells by both immunofluorescence and flow cytometry, as shown in FIG. 23.

The prostate cancer cell line PC-3 was cultured in flasks containing DMEM high-glucose supplemented with 10% fetal calf serum and subsequently harvested using cell dissociation buffer (Gibco Cat. No. 13150-016) per package insert. Cells were counted on a hemocytometer and either 500 or 1,000 cells were spiked into 7.5 mL of blood obtained from healthy volunteers as described above. A median of 31.4% (range 16.1-103.4, n=13) of spiked cells were recovered using OB-cadherin capture and characterization as beta-catenin positive, CD45 negative cells as above.

The collection of the mesenchymal phenotypic CTC left open the possibility that cellular events were not cancer cells, but rather host cells. For example, in healthy volunteers, the OB-cadherin positive cells were most likely endothelial cells derived from phlebotomy as they were CD31 positive. In men with metastatic CRPC (mCRPC), these OB-cadherin positive cells could be endothelial or circulating osteoblasts, bone marrow derived mesenchymal cells, or other circulating mesenchymal-like cells expressing OB-cadherin. To determine the significance of OB-cadherin captured events from patients and whether these cellular events represented host cells or prostate cancer cells, DNA fluorescence in situ hybridization (FISH) was performed for prostate cancer-specific genomic events. Cellular events were identified using the CELLTRACKS ANALYZER II® as described above and then fixed and dried on the cartridge for DNA FISH. Using a 4-color FISH assay for androgen receptor (AR) amplification, PTEN loss, and gene fusion involving the TMPRSS2-ERG locus (ERG break-apart assay), as previously described (Attard et al. (2009) Cancer Res 69:2912-2918), the captured mesenchymal cells were evaluated for these prostate-cancer specific changes. As shown in FIG. 24, AR amplification and the TMPRSS2-ERG fusion were present in both EpCAM and OB-cadherin captured cells, indicating that these cellular events were tumor-derived.

As these genomic amplification or deletion events were unlikely to be found in normal tissues, and were found in the EpCAM positive cells, these findings suggest that at least some of the OB-cadherin, beta-catenin positive cells were prostate cancer derived and not derived from the tumor microenvironment or normal host cells. Further analysis of the prevalence of these mesenchymal phenotypic CTCs in a broader population of men with mCRPC and other tumor types indicate the usefulness of this assay to complement existing CTC assays. These analyses may include comparison with EpCAM based approaches, particularly in men with low CTC counts despite progressive metastatic disease, to define the clinical utility of OB-cadherin positive events. In addition, correlations of OB-cadherin positive cellular events with clinical and pathologic characteristics and patient outcomes with systemic therapies further define the independent role of this assay in the context of other prognostic biomarkers. These methods and data suggested that these cells were detectable in men with mCRPC, were absent in healthy volunteers, and that the disclosed methods detected OB-cadherin positive human prostate cancer cells in blood.

The common expression of OB-cadherin in CTCs suggested osteomimicry, and provided some insight into the mechanism of prostate cancer homing to bone and the development of osteoblastic bone metastases. OB-cadherin events in healthy volunteers uniformly expressed the endothelial marker CD31, whereas the CD31 status in patients with cancer was more variable. Additional markers may be used to confirm that these mesenchymal-like cells were tumor cells (e.g., FISH, cytokeratin, PSA).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for isolating, capturing, or enriching a circulating tumor cell from a patient, the method comprising:
   a) obtaining a biological sample from a patient;
   b) obtaining at least one capture binding protein, wherein the capture binding protein is linked to a solid phase to form a solid phase-capture binding protein complex, and wherein the capture binding protein is an epithelial-mesenchymal transition (EMT) biomarker capture antibody;
   c) contacting the biological sample with the solid phase-capture binding protein complex for a time sufficient to allow the solid phase-capture binding protein complex to bind at least one EMT biomarker on the circulating tumor cell to form a solid phase-capture binding protein-circulating tumor cell complex, wherein the EMT biomarker is at least one of OB-cadherin, N-cadherin, vimentin, E-cadherin, FGFR2 splice variant isoforms, or CD133;
   d) separating the solid phase-capture binding protein-circulating tumor cell complex from the sample and unbound magnetic particle-capture binding protein complexes by application of an external magnetic field on the sample, thereby isolating, capturing, or enriching the circulating tumor cell; and
   e) confirming the circulating tumor cell, wherein confirming comprises β-catenin expression detection and CD31 expression detection, wherein the circulating tumor cell is confirmed if β-catenin expression is positive and CD31 expression is negative.

2. The method of claim 1, wherein confirming the circulating tumor cell further comprises at least one of DAPI staining and CD45 detection.

3. The method of claim 2, wherein the circulating tumor cell is further confirmed if DAPI staining is positive and CD45 expression is negative.

4. The method of claim 1, wherein the circulating tumor cell has a mesenchymal phenotype.

5. The method of claim 1, wherein the patient has cancer.

6. The method of claim 1, further comprising determining the presence or absence of at least one prostate cancer-specific genomic event.

7. The method of claim 6, wherein the at least one prostate cancer-specific genomic event is selected from the group consisting of androgen receptor amplification, phosphatase and tensin homolog (PTEN) loss, gene fusion of transmembrane protease, serine 2 (TMPRSS2) gene and ETS related (ERG) gene, and combinations thereof.

8. The method of claim 1, wherein the biological sample comprises a tissue sample or a fluid sample from an organism.

9. The method of claim 1, wherein the β-catenin expression detection comprises contacting the solid phase-capture binding protein-circulating tumor cell complex with a first staining reagent that binds β-catenin, and wherein the CD31 expression detection comprises contacting the solid phase-capture binding protein-circulating tumor cell complex with a second staining reagent that binds CD31.

10. The method of claim 9, wherein the first staining reagent comprises an antibody that binds β-catenin.

11. The method of claim 9, wherein the second staining reagent comprises an antibody that binds CD31.

* * * * *